(12) United States Patent
Labib et al.

(10) Patent No.: US 12,064,495 B2
(45) Date of Patent: Aug. 20, 2024

(54) ORAL CAVITY CLEANING COMPOSITION, METHOD, AND APPARATUS

(71) Applicant: Protegera, Inc., Madison, WI (US)

(72) Inventors: Mohamed Emam Labib, West Palm Beach, FL (US); Antonio Perazzo, Princeton, NJ (US); Anthony E. Winston, East Brunswick, NJ (US); Yacoob Tabani, Basking Ridge, NJ (US); James L. Manganaro, Princeton, NJ (US); Lucas Lawrence Franz, Mount Laurel, NJ (US); Seo Yean Sohn, Princeton, NJ (US); Christopher Kuchar, Hopewell, NJ (US)

(73) Assignee: Protegera, Inc., Madison, WI (US)

( * ) Notice: Subject to any disclaimer, the term of this patent is extended or adjusted under 35 U.S.C. 154(b) by 499 days.

(21) Appl. No.: 17/225,049

(22) Filed: Apr. 7, 2021

(65) Prior Publication Data

US 2021/0330557 A1 Oct. 28, 2021

Related U.S. Application Data

(63) Continuation-in-part of application No. 17/062,424, filed on Oct. 2, 2020.

(60) Provisional application No. 63/169,585, filed on Apr. 1, 2021, provisional application No. 62/913,565, filed on Oct. 10, 2019, provisional application No. 62/910,049, filed on Oct. 3, 2019.

(51) Int. Cl.

| | |
|---|---|
| *A61Q 11/00* | (2006.01) |
| *A61K 8/02* | (2006.01) |
| *A61K 8/04* | (2006.01) |
| *A61K 8/73* | (2006.01) |
| *D01D 5/42* | (2006.01) |
| *B82Y 5/00* | (2011.01) |
| *B82Y 40/00* | (2011.01) |

(52) U.S. Cl.
CPC ............ *A61K 8/027* (2013.01); *A61K 8/042* (2013.01); *A61K 8/731* (2013.01); *A61Q 11/00* (2013.01); *D01D 5/423* (2013.01); *A61K 2800/28* (2013.01); *A61K 2800/805* (2013.01); *A61K 2800/92* (2013.01); *B82Y 5/00* (2013.01); *B82Y 40/00* (2013.01); *D10B 2201/00* (2013.01); *D10B 2401/02* (2013.01); *D10B 2509/00* (2013.01)

(58) Field of Classification Search
CPC ........ A61Q 11/00; A61K 8/731; A61K 8/027; A61K 47/38; A61K 2800/28
See application file for complete search history.

(56) References Cited

U.S. PATENT DOCUMENTS

| | | |
|---|---|---|
| 3,209,771 A | 10/1965 | Gogarty et al. |
| 3,225,787 A | 12/1965 | Gogarty et al. |
| 3,852,200 A | 12/1974 | Meyer |
| 4,003,393 A | 1/1977 | Jaggard et al. |
| 4,075,316 A * | 2/1978 | Cordon .................... A61K 8/26 424/57 |
| 4,216,026 A | 8/1980 | Scott |
| 4,254,559 A | 3/1981 | Purinton, Jr. |
| 4,270,914 A | 6/1981 | Dahl |
| 4,304,050 A | 12/1981 | Morud et al. |
| 4,341,807 A | 7/1982 | Turbak et al. |
| 4,362,713 A | 12/1982 | Buck |
| 4,374,702 A | 2/1983 | Turbak et al. |
| 4,378,381 A | 3/1983 | Turbak et al. |
| 4,406,030 A | 9/1983 | Platts |
| 4,416,703 A | 11/1983 | Scott |
| 4,473,408 A | 9/1984 | Purinton, Jr. |
| 4,481,077 A | 11/1984 | Herrick |
| 4,500,546 A | 2/1985 | Turbak et al. |
| 4,525,220 A | 6/1985 | Sasa et al. |
| 4,543,131 A | 9/1985 | Purinton, Jr. |
| 4,629,575 A | 12/1986 | Weibel |
| 4,693,840 A | 9/1987 | Trinh et al. |
| 4,775,525 A | 10/1988 | Pera |
| 4,805,598 A | 2/1989 | Ueda |
| 4,855,128 A | 8/1989 | Lynch et al. |

(Continued)

FOREIGN PATENT DOCUMENTS

| | | |
|---|---|---|
| CA | 2 013 120 A1 | 10/1990 |
| CA | 2 921 174 A1 | 2/2015 |

(Continued)

OTHER PUBLICATIONS

Cheng et al., "Water Retention Value Measurements of Cellulosic Materials Using a Centrifuge Technique," BioResources, vol. 5, No. 3, pp. 1945-1954 (2010).
Homma et al., "Effects of carboxyl-group counter-ions on biodegradation behaviors of TEMPO-oxidized cellulose fibers and nanofibril films," Cellulose, vol. 20, pp. 2505-2515 (2013).
Turbak, "Birth of Nanocellulose," www.naylornetwork.com/ppi-otw/articles/?aid=150993&issue1 0=22333, TAPPI, 4 pages (2011).
Exhibit A—the pending claims U.S. Appl. No. 17/737,654.
Exhibit B—the pending claims U.S. Appl. No. 17/751,186.
Exhibit C—the pending claims U.S. Appl. No. 17/062,424.
Adamcik et al., "Proteins Fibrils from a Polymer Physics Perspective," Macromolecules, vol. 45, pp. 1137-1150 (2012).

(Continued)

*Primary Examiner* — Tracy Liu
(74) *Attorney, Agent, or Firm* — Merchant & Gould P.C

(57) ABSTRACT

An oral hygiene composition includes a mixture of: (i) a carrier liquid; and (ii) a water-insoluble hydratable polymer fibers forming an entangled three-dimensional network of said water-insoluble hydratable polymer fibers in said carrier; wherein: said carrier liquid comprises one or more humectant in a concentration of total humectant in excess of 5 wt. % based on the weight of the composition; said composition has an elastic modulus G' and a loss modulus G", and said elastic modulus G' is larger that said loss modulus G"; and said water-insoluble hydratable polymer fibers have a diameter of about 10 to about 20,000 nm and a length of at least 100 nm.

34 Claims, 20 Drawing Sheets

(56) References Cited

U.S. PATENT DOCUMENTS

| | | |
|---|---|---|
| 4,860,821 A | 8/1989 | Hagewood |
| 4,914,170 A | 4/1990 | Chang et al. |
| 5,075,104 A | 12/1991 | Gressel et al. |
| 5,202,112 A | 4/1993 | Prencipe et al. |
| 5,260,021 A | 11/1993 | Zeleznick |
| 5,346,339 A | 9/1994 | Himes et al. |
| 5,362,480 A | 11/1994 | Au et al. |
| 5,443,801 A | 8/1995 | Langford |
| 5,512,199 A | 4/1996 | Khan et al. |
| 5,527,204 A | 6/1996 | Rhoades |
| 5,681,399 A | 10/1997 | Okano |
| 5,703,026 A | 12/1997 | Setser et al. |
| 5,731,080 A | 3/1998 | Cousin et al. |
| 5,763,335 A | 6/1998 | Hermann |
| 5,885,133 A | 3/1999 | Williams, Jr. |
| 5,998,349 A | 12/1999 | Guillou |
| 6,027,572 A | 2/2000 | Labib et al. |
| 6,037,380 A | 3/2000 | Venables et al. |
| 6,045,623 A | 4/2000 | Cannon |
| 6,272,713 B1 | 8/2001 | Lotwin |
| 6,288,154 B1 | 9/2001 | Rhoades |
| 6,447,990 B1 | 9/2002 | Alfa |
| 6,506,435 B1 | 1/2003 | Lundberg et al. |
| 6,541,627 B1 | 4/2003 | Ono et al. |
| 6,602,994 B1 | 8/2003 | Cash et al. |
| 6,683,036 B2 | 1/2004 | Foley et al. |
| 6,699,331 B1 | 3/2004 | Kritzler |
| 6,797,245 B2 | 9/2004 | Nakanishi et al. |
| 6,803,107 B2 | 10/2004 | Mitchell et al. |
| 6,849,581 B1 | 2/2005 | Thompson et al. |
| 6,889,400 B2 | 5/2005 | Kawazoe et al. |
| 6,903,057 B1 | 6/2005 | Tsaur |
| 6,905,986 B2 | 6/2005 | Ranganathan et al. |
| 6,967,027 B1 | 11/2005 | Heux et al. |
| 7,037,405 B2 | 5/2006 | Nguyen et al. |
| 7,135,163 B2 | 11/2006 | Winston et al. |
| 7,306,846 B2 | 12/2007 | Dezutter et al. |
| 7,341,623 B2 | 3/2008 | Holl et al. |
| 7,343,972 B2 | 3/2008 | Willingham et al. |
| 7,393,820 B2 | 7/2008 | Soldanski et al. |
| 7,459,028 B2 | 12/2008 | Kral et al. |
| 7,776,807 B2 | 8/2010 | Canto et al. |
| 7,820,873 B2 | 10/2010 | Sun et al. |
| 7,824,608 B2 | 11/2010 | Kuroshima et al. |
| 7,879,289 B2 | 2/2011 | Williams |
| 7,883,726 B2 | 2/2011 | Crutchfield, III |
| 7,888,308 B2 | 2/2011 | Swazey |
| 7,994,111 B2 | 8/2011 | Caggioni et al. |
| 8,097,574 B2 | 1/2012 | Heath et al. |
| 8,187,056 B2 | 5/2012 | Hashish et al. |
| 8,206,349 B2 | 6/2012 | Slenker et al. |
| 8,211,411 B2 | 7/2012 | Deckner et al. |
| 8,357,378 B2 | 1/2013 | Wallace et al. |
| 8,445,422 B2 | 5/2013 | Gonzales et al. |
| 8,466,097 B2 | 6/2013 | Allef et al. |
| 8,546,316 B2 | 10/2013 | Perez-Prat Vinuesa et al. |
| 8,546,558 B2 | 10/2013 | Ankerfors et al. |
| 8,642,529 B2 | 2/2014 | Palla-Venkata et al. |
| 8,703,691 B2 | 4/2014 | Caggioni et al. |
| 8,716,213 B2 | 5/2014 | Caggioni et al. |
| 8,741,855 B2 | 6/2014 | Quave et al. |
| 8,772,359 B2 | 7/2014 | Swazey |
| 8,785,621 B2 | 7/2014 | Flury et al. |
| 8,790,301 B2 | 7/2014 | Slenker et al. |
| 8,795,637 B2 | 8/2014 | Deckner et al. |
| 8,852,643 B2 | 10/2014 | Gonzales et al. |
| 8,920,574 B2 | 12/2014 | Bhaumik et al. |
| 8,980,011 B2 | 3/2015 | Sumnicht et al. |
| 9,045,716 B2 | 6/2015 | Swazey et al. |
| 9,149,274 B2 | 10/2015 | Spivey et al. |
| 9,162,007 B2 | 10/2015 | Bitis et al. |
| 9,163,201 B2 | 10/2015 | Gonzales et al. |
| 9,193,982 B2 | 11/2015 | Sjoede et al. |
| 9,289,449 B2 | 3/2016 | Sershen et al. |
| 9,339,172 B2 | 5/2016 | Slenker et al. |
| 9,370,478 B2 | 6/2016 | Bonner et al. |
| 9,453,156 B2 | 9/2016 | Wu |
| 9,457,453 B2 | 10/2016 | Seth et al. |
| 9,492,373 B2 | 11/2016 | Canova et al. |
| 9,534,191 B2 | 1/2017 | Fernandez-Prieto et al. |
| 9,549,890 B2 | 1/2017 | Bonner et al. |
| 9,616,002 B2 | 4/2017 | Gonzales et al. |
| 9,616,008 B2 | 4/2017 | Bhushan et al. |
| 9,617,459 B2 | 4/2017 | Van Engelen et al. |
| 9,550,597 B2 | 5/2017 | Konya et al. |
| 9,677,030 B2 | 6/2017 | Napolitano |
| 9,693,675 B2 | 7/2017 | Matta et al. |
| 9,796,914 B2 | 10/2017 | Shen et al. |
| 9,826,877 B2 | 11/2017 | DeMarco et al. |
| 9,840,660 B2 | 12/2017 | Chopade et al. |
| 9,862,916 B2 | 1/2018 | Van Engelen et al. |
| 9,884,137 B2 | 2/2018 | Kettlewell et al. |
| 10,100,269 B2 | 10/2018 | Fernandez-Prieto et al. |
| 10,199,269 B2 | 2/2019 | Chen et al. |
| 10,253,457 B2 | 4/2019 | Husband et al. |
| 10,266,792 B2 | 4/2019 | Sivik et al. |
| 10,266,793 B2 | 4/2019 | Labib et al. |
| 10,337,146 B2 | 7/2019 | Holtan et al. |
| 10,337,147 B2 | 7/2019 | Rouse et al. |
| 10,617,791 B2 | 4/2020 | Nunes et al. |
| 10,925,773 B2 | 2/2021 | Riesinger |
| 11,326,128 B2 | 5/2022 | Labib et al. |
| 11,345,878 B2 | 5/2022 | Labib et al. |
| 11,680,226 B2 | 6/2023 | Labib et al. |
| 2001/0011516 A1 | 8/2001 | Cantiani et al. |
| 2003/0121532 A1 | 7/2003 | Coughlin et al. |
| 2003/0191204 A1 | 10/2003 | Hermann et al. |
| 2003/0213501 A1 | 11/2003 | Thomson et al. |
| 2004/0000012 A1 | 1/2004 | Scarpello et al. |
| 2005/0137274 A1 | 6/2005 | Ko et al. |
| 2005/0201965 A1 | 9/2005 | Kuhlman et al. |
| 2005/0220727 A1 | 10/2005 | Lupia et al. |
| 2006/0020126 A1 | 1/2006 | Kopesky et al. |
| 2006/0032633 A1 | 2/2006 | Nguyen |
| 2006/0034782 A1 | 2/2006 | Brown et al. |
| 2006/0171913 A1 | 8/2006 | Schroder |
| 2006/0249265 A1 | 11/2006 | Scarpello et al. |
| 2007/0106013 A1 | 5/2007 | Adachhi et al. |
| 2007/0141095 A1 | 6/2007 | Simonnet |
| 2007/0151680 A1 | 7/2007 | Scarpello et al. |
| 2007/0199668 A1 | 8/2007 | Scarpello et al. |
| 2008/0082065 A1 | 4/2008 | Weerawarna et al. |
| 2008/0082067 A1 | 4/2008 | Weerawarna et al. |
| 2008/0108534 A1 | 5/2008 | Bernard et al. |
| 2008/0147026 A1 | 6/2008 | Qin et al. |
| 2009/0095324 A1 | 4/2009 | Crowther et al. |
| 2009/0269376 A1 | 10/2009 | Lundberg et al. |
| 2009/0306223 A1 | 12/2009 | Cai et al. |
| 2009/0324514 A1 | 12/2009 | Awad |
| 2010/0009891 A1 | 1/2010 | Canto et al. |
| 2010/0210501 A1 | 8/2010 | Caggioni et al. |
| 2010/0221294 A1 | 9/2010 | Kurek et al. |
| 2010/0247615 A1* | 9/2010 | Toreki ............ A61K 33/40 602/41 |
| 2010/0264364 A1* | 10/2010 | Wagner ............ B82Y 30/00 252/182.12 |
| 2011/0262504 A1 | 10/2011 | Deleersnyder et al. |
| 2012/0090192 A1 | 4/2012 | Oevreboe et al. |
| 2012/0100193 A1* | 4/2012 | Nowak ............ A61Q 11/00 424/56 |
| 2012/0100367 A1 | 4/2012 | Holtan et al. |
| 2012/0237576 A1 | 9/2012 | Gordon et al. |
| 2012/0267570 A1 | 10/2012 | Shi et al. |
| 2013/0029895 A1 | 1/2013 | Bettiol et al. |
| 2013/0072417 A1 | 3/2013 | Perez-Prat Vinuesa et al. |
| 2013/0098407 A1 | 4/2013 | Perlman et al. |
| 2013/0180679 A1 | 7/2013 | Laine et al. |
| 2013/0230609 A1* | 9/2013 | Modak ............ A61P 17/10 424/769 |
| 2013/0261208 A1 | 10/2013 | Borges De Couraca et al. |
| 2014/0000891 A1 | 1/2014 | Mahoney et al. |
| 2014/0128480 A1 | 5/2014 | Swazey et al. |
| 2014/0221948 A1* | 8/2014 | Riesinger ............ A61L 15/46 424/490 |

(56) References Cited

U.S. PATENT DOCUMENTS

| | | |
|---|---|---|
| 2014/0238444 A1 | 8/2014 | Arai |
| 2015/0031592 A1 | 1/2015 | Barreleiro et al. |
| 2015/0191681 A1 | 7/2015 | Gonzales et al. |
| 2015/0210957 A1 | 7/2015 | Napolitano |
| 2015/0210967 A1 | 7/2015 | Van Engelen et al. |
| 2015/0305819 A1 | 10/2015 | Krause |
| 2016/0222275 A1 | 8/2016 | Galindo et al. |
| 2016/0312298 A1 | 10/2016 | Ting et al. |
| 2016/0325318 A1 | 11/2016 | Tyrrell et al. |
| 2016/0331703 A1 | 11/2016 | Myntti |
| 2016/0332141 A1 | 11/2016 | Machida et al. |
| 2016/0346427 A1 | 12/2016 | Nunes et al. |
| 2016/0367102 A1 | 12/2016 | DeMarco et al. |
| 2017/0044468 A1 | 2/2017 | Gori et al. |
| 2017/0121908 A1 | 5/2017 | Holtan et al. |
| 2017/0183555 A1 | 6/2017 | Lillandt et al. |
| 2017/0191003 A1 | 7/2017 | Fernandez-Prieto et al. |
| 2017/0197071 A1 | 7/2017 | Gottenbos |
| 2018/0078484 A1 | 3/2018 | Blell et al. |
| 2018/0094214 A1* | 4/2018 | Labib ............... C11D 11/0023 |
| 2019/0249115 A1 | 8/2019 | Labib et al. |
| 2020/0270551 A1 | 8/2020 | Labib et al. |
| 2021/0121386 A1 | 4/2021 | Labib et al. |
| 2022/0396752 A1 | 12/2022 | Labib et al. |

FOREIGN PATENT DOCUMENTS

| | | |
|---|---|---|
| CN | 1163748 A | 11/1997 |
| CN | 1994268 A | 7/2007 |
| CN | 103599000 B | 1/2016 |
| CN | 106691886 B | 4/2020 |
| EP | 0 198 094 A1 | 10/1986 |
| EP | 0 392 248 A1 | 10/1990 |
| EP | 0 845 495 A2 | 6/1998 |
| EP | 2 100 590 A1 | 9/2009 |
| EP | 3 081 209 A1 | 10/2016 |
| EP | 3 033 116 B1 | 4/2021 |
| JP | 2010-509462 A | 3/2010 |
| JP | 2011-505340 A | 2/2011 |
| JP | 2011-513507 A | 4/2011 |
| JP | 2014-521769 A | 8/2014 |
| JP | 2014-181247 A | 9/2014 |
| JP | 2015-508300 A | 3/2015 |
| JP | WO2013092633 | 3/2015 |
| JP | 2015-522014 A | 8/2015 |
| JP | 2016-527065 A | 9/2016 |
| KR | 10-0555300 B1 | 3/2006 |
| KR | 10-2009-0071717 A | 7/2009 |
| KR | 10-1035140 B1 | 5/2011 |
| TW | I419708 B | 12/2013 |
| WO | WO 92/18151 A1 | 10/1992 |
| WO | WO 95/34275 A1 | 12/1995 |
| WO | WO 00/47628 A1 | 8/2000 |
| WO | WO 03/040284 A1 | 5/2003 |
| WO | WO 2006/008645 A2 | 1/2006 |
| WO | WO 2007/091942 A1 | 8/2007 |
| WO | WO 2008/109270 A1 | 9/2008 |
| WO | WO 2009/068841 A2 | 6/2009 |
| WO | WO 2009/101545 A1 | 8/2009 |
| WO | WO 2010/070354 A1 | 6/2010 |
| WO | WO 2012/040314 A1 | 3/2012 |
| WO | WO 2012/052306 A1 | 4/2012 |
| WO | WO 2012/065924 A1 | 5/2012 |
| WO | WO 2012/107648 A1 | 8/2012 |
| WO | WO 2013/009225 A1 | 1/2013 |
| WO | WO 2014/003776 A1 | 1/2014 |
| WO | WO 2014/075845 A1 | 5/2014 |
| WO | WO 2014/082951 A2 | 6/2014 |
| WO | WO 2014/088072 A1 | 6/2014 |
| WO | WO 2014/154348 A1 | 10/2014 |
| WO | WO 2015/022340 A1 | 2/2015 |
| WO | WO 2015/180844 A1 | 12/2015 |
| WO | WO 2016/086951 A1 | 6/2016 |
| WO | WO 2016/100822 A1 | 6/2016 |
| WO | WO 2016/166179 A1 | 10/2016 |
| WO | WO 2018/064284 A1 | 4/2018 |
| WO | WO 2019/195403 A1 | 10/2019 |

OTHER PUBLICATIONS

Alfa et al., "A novel polytetrafluoroethylene-channel model, which simulates low levels of culturable bacteria in buildup biofilm after repeated endoscope reprocessing," Gastrointestinal Endoscopy, vol. 86, No. 3, pp. 442-451 (2017).

Au et al., "Behaviour of LAPONITE® gels: rheology, ageing, pH effect and phase state in the presence of dispersant," Chemical Engineering Research and Design, vol. 101, pp. 65-73 (Sep. 2015).

Bolden et al., "The Clinical Effect of a Dentifrice Containing Triclosan and a Copolymer in a Sodium Fluoride/Silica Base on Plaque Formation And Gingivitis: A Six-Month Clinical Study," *J Clin Dent*, vol. 3, No. 4, pp. 125-131 (1992).

Bonfil et al., "The influence of gingival stimulation on recovery from human experimental gingivitis," Journal of Clinical Periodontology, vol. 12, pp. 828-836 (1985).

Bowen et al., Biology of *Streptococcus mutans*-Derived Glucosyltransferases: Role in Extracellular Matrix Formation of Cariogenic Biofilms, Caries Res, vol. 45, pp. 69-86 (2011).

Chen et al., "Role of electrostatic interactions in cohesion of bacterial biofilms," Applied Microbiology and Biotechnology, vol. 59, pp. 718-720 (2002).

Chu et al., "Smart wormlike micelles," Chemical Society Reviews, vol. 42, pp. 7174-7203 (2013).

Cipriano et al., "Superabsorbent Hydrogels That Are Robust and Highly Stretchable," Macromolecules, vol. 47, pp. 4445-4452 (2014).

Cubells et al., "The Effect of a Triclosan/Copolymer/Fluoride Dentifrice on Plaque Formation and Gingivitis: A Six-Month Clinical Study," *J Clin Dent*, vol. 2, No. 3, pp. 63-69 (1991).

De Oliveira et al., "Toothbrushing, inflammation and risk of cardiovascular disease: results from Scottish Health Survey," BMJ, doi: 10.1136/bmj.c2451, 340:c2451 (2010).

Dreiss, "Wormlike micelles: where do we stand? Recent developments, linear rheology and scattering techniques," Soft Matter, vol. 3, pp. 956-970 (2007).

Gallob et al., "Comparative Efficacy of a Soft Toothbrush with Tapered-tip Bristles and an ADA Reference Toothbrush on Established Gingivitis and Supragingival Plaque over a 12-Week Period," The Journal of Clinical Dentistry, vol. 27, No. 2, pp. 39-47 (2016).

Gaudino et al., "Adding salt to a surfactant solution: Linear rheological response of the resulting morphologies," Journal of Rheology, vol. 59, No. 6, pp. 1363-1375 (Nov./Dec. 2015).

George et al., Cellulose Nanocrystals: synthesis, functional properties, and applications. Nanotechnology, Science and Applications, vol. 8, pp. 47-54 (2015).

Gloag et al., "Viscoelastic properties of *Pseudomonas aeruginosa* variant biofilms," Scientific Reports, 8:9691 DOI: 10.1038/s41598-018-28009-5 (2018).

Grabenstetter et al., "The measurement of the abrasion of human teeth by dentifrice abrasives: A test utilizing radioactive teeth," J Dent Res, vol. 37, No. 6, pp. 1060-1068 (Nov.-Dec. 1958).

Gusnaniar et al., "Transmission of Monospecies and Dual-Species Biofilms from Smooth to Nanopillared Surfaces," Appl. Environ. Microbiol., vol. 84, Issue 15, e01035-18, 11 pages (Aug. 2018).

Hammer et al., "Cross-Linked Conjugated Polymer Fibrils: Robust Nanowires from Functional Polythiophene Diblock Copolymers," Chemistry of Materials, vol. 23, pp. 4250-4256 (2011).

Heydorn et al., "Quantification of biofilm structures by the novel computer program COMSTAT," Microbiology, vol. 146, pp. 2395-2407 (2000).

International Search Report and Written Opinion for Application No. PCT/US2020/054149 mailed Jan. 19, 2021.

Jayakumar et al, "Role of Dentifrice in plaque removal: A clinical trial," Indian Journal of Dental Research, vol. 21, Issue 2, pp. 213-217 (Apr.-Jun. 2010).

Kerr et al., "Chemical Composition and In-vitro Digestibility of Thermochemically Treated Peanut Hulls," J. Sci. Food Agric., vol. 37, pp. 632-636 (1986).

(56) References Cited

OTHER PUBLICATIONS

Khosravi et al., "Use of an oxygen planar optode to assess the effect of high velocity microsprays on oxygen penetration in a human dental biofilms in-vitro," BMC Oral Health 20:230 https://doi.org/10.1186/s12903-020-01217-0 (2020).

Kolenbrander et al., "Adhere Today, Here Tomorrow: Oral Bacterial Adherence," Journal of Bacteriology, vol. 175, No. 11, pp. 3247-3252 (Jun. 1993).

Koo et al., "Exopolysaccharides Produced by *Streptococcus mutans* Glucosyltransferases Modulate the Establishment of Microcolonies within Multispecies Biofilms," Journal of Bacteriology, vol. 192, No. 12, pp. 3024-3032 (Jun. 2010).

Lewis et al., "Interaction between toothbrushes and toothpaste abrasive particles in simulated tooth cleaning," Wear, vol. 257, No. 3-4, pp. 368-376 (2004).

Mateu et al., "A Clinical Investigation of the Efficacy of Two Dentifrices for Controlling Established Supragingival Plaque and Gingivitis," *J Clin Dent*, vol. 19, No. 3, pp. 85-94 (2008).

Mignon et al, "Superabsorbent polymers: A review on the characteristics and applications of synthetic, polysaccharide-based semi-synthetic and 'smart' derivatives," European Polymer Journal, vol. 117, pp. 165-178 (2019).

Morozova, "Methylcellulose fibrils: a mini review," Polymer International, vol. 69, No. 2, pp. 125-130 (2020).

Palmer et al., "*Streptococcus mutans* yidC1 and yidC2 Impact Cell Envelope Biogenesis, the Biofilm Matrix, and Biofilm Biophysical Properties," Journal of Bacteriology, vol. 201, Issue 1, e00396-18, https://doi.org/10.1128/JB.00396-18, (Jan. 2019).

Paraskevas et al., Additional Effect of Dentifrices on the Instant Efficacy of Toothbrushing, J Periodontology, vol. 77, No. 9, pp. 1522-1527 (2006).

Perazzo et al., "Flow-induced gelation of microfiber suspensions," Proceedings of the National Academy of Sciences, 114(41):201710927, DOI: 10.1073/pnas.1710927114, E8557-E8564 (2017).

Perazzo et al, "Emulsions in porous media: From single droplet behavior to applications for oil recovery," Advances in Colloid and Interface Sciences, vol. 256, pp. 305-325 (2018).

Pointner et al., "Composition of corncobs as a substrate for fermentations of biofuels," Agronomy Research, vol. 12, No. 2, pp. 391-396 (2014).

Rizvi et al., "Dispersed polypropylene fibrils improve the foaming ability of a polyethylene matrix," Polymer, vol. 55, No. 16, pp. 4199-4205 (2014).

Rmaile et al., "Microbial tribology and disruption of dental plaque bacterial biofilms," Wear, vol. 306, Issues 1-2, pp. 276-284 (Aug. 30, 2013).

Schemehorn et al., "Abrasion, Polishing, and Stain Removal Characteristics of Various Commercial Dentifrices In Vitro," J Clin Dent, vol. 22, No. 11, pp. 11-18 (2011).

Sharma et al., "The Clinical Effects on Plaque and Gingivitis Over Three-Months Use of Four Complex-Design Manual Toothbrushes," *J Clin Dent*, vol. 5, No. 4, pp. 114-118 (1994).

Stoodley et al., "Structural Deformation of Bacterial Biofilms Caused by Short-Term Fluctuations in Fluid Shear: An In Situ Investigation of Biofilm Rheology," Biotechnology and Bioengineering, vol. 65, No. 1, pp. 83-92 (Oct. 5, 1999).

Tavakolian, et al., "A Review on Surface-Functionalized Cellulosic Nanostructures as Biocompatible Antibacterial Materials," Nano-Micro Lett. 12, 73 (2020). https://doi.org/10.1007/s40820-020-0408-4.

Valkenburg et al., "Does Dentifrice Use Help to Remove Plaque? A Systematic Review," Journal of Clinical Periodontology, vol. 43, pp. 1050-1058, doi: 10.1111/jcpe.12615 (2016).

Van der Rijt et al., "Micromechanical Testing of Individual Collagen Fibrils," Macromolecular Bioscience, vol. 6, pp. 697-702 (2006).

Verkaik et al., "Oral biofilm models for mechanical plaque removal," Clin. Oral. Invest., vol. 14, pp. 403-409 (2010).

Vinogradov et al., "Rheology of biofilms formed from the dental plaque pathogen *Streptococcus mutans*," Biofilms, vol. 1, pp. 49-56 (2004).

Volpatti et al., "Polymer Physics Inspired Approaches for the Study of the Mechanical Properties of Amyloid Fibrils," Journal of Polymer Science, Part B: Polymer Physics, vol. 52, pp. 281-292 (2014).

Walsh et al., "Fluoride toothpastes of Different Concentrations for Preventing Dental Caries (Review)," Cochrane Database of Systematic Reviews, Issue 3. Art. No. CD007868 DOI: 10.1002/14651858.CD007868.pub3 (2019).

Yang et al., "Structural and Ecofriendly Holocellulose Materials from Wood: Microscale Fibers and Nanoscale Fibrils," Advanced Materials, Jan. 18, 2001 (2020).

Yu et al., "Scalable manufacturing of biomimetic moldable hydrogels for industrial applications," PNAS, vol. 113, No. 50, pp. 14255-14260 (Dec. 13, 2016).

Yumoto et al., "The Pathogenic Factors from Oral Streptococci for Systemic Diseases," Int. J. Mol. Sci., 2019, 20, 4571; doi:10.3390/ijms20184571, pp. 1-18.

Zanatta et al., "Supragingival Plaque Removal with and without Dentifrice: A Randomized Controlled Clinical Trial," Braz. Dent J., vol. 23, No. 3, pp. 235-240 (2012).

Exhibit A—the allowed claims U.S. Appl. No. 16/279,443.

Exhibit B—the allowed claims U.S. Appl. No. 16/461,536.

International Search Report and Written Opinion for Application No. PCT/US2022/023160 mailed Aug. 4, 2022.

\* cited by examiner

Composition made with glycerol-water mixture

Composition made with water

TP 60

Embodiment composition is made with surface crosslinked SAP

MCC (PH200) alone

MCC (PH200) in the presence of MFC

Silicified MCC (SMCC50) alone 3_ch00

Silicified MCC (SMCC50) in the presence of MFC

Control

Rank 4

Rank 3

Rank 2

Rank 1

Sample images at low and high magnification.

Sample images at low and high magnification.

ORAL CAVITY CLEANING COMPOSITION, METHOD, AND APPARATUS

CLAIM OF PRIORITY AND CROSS-REFERENCE TO RELATED APPLICATIONS

This patent disclosure claims the benefit, to the extent appropriate, of U.S. Provisional patent application Ser. No. 63/169,585 filed Apr. 1, 2021, and of U.S. patent application Ser. No. 17/062,424 filed Oct. 2, 2020, which claims priority to U.S. Provisional patent application Ser. No. 62/910,049, filed Oct. 3, 2019, and U.S. Provisional patent application Ser. No. 62/913,565, filed Oct. 10, 2019. U.S. Provisional patent application Ser. Nos. 63/169,585, 62/910,049, and 62/913,565, and U.S. patent application Ser. No. 17/062,424 are incorporated herein by reference in their entireties.

The following additional patent application disclosures are incorporated herein by reference: Provisional Patent Application U.S. Ser. No. 62/402,394, filed Sep. 30, 2016, including its appendix; Provisional Patent Application U.S. Ser. No. 62/563,975, filed Sep. 27, 2017, including its appendices; Nonprovisional patent application U.S. Ser. No. 15/718,325, filed Sep. 28, 2017, which published as US20180094214A1 and issued as U.S. Ser. No. 10/266,793; PCT patent application PCT/US17/53925, filed Sep. 28, 2017, which published as WO2018064284A1; Provisional Patent Application U.S. Ser. No. 62/652,079, filed Apr. 3, 2018; Provisional Patent Application U.S. Ser. No. 62/692,082 filed Jun. 29, 2018; Provisional Patent Application U.S. Ser. No. 62/822,432 filed Mar. 22, 2019; Provisional Patent Application U.S. Serial No. U.S. Ser. No. 62/828,134 filed Apr. 2, 2019; PCT/US2019/025558, filed Apr. 3, 2019; patent application U.S. Ser. No. 16/461,536 filed May 16, 2019.

FIELD OF THE INVENTION

Embodiments of the invention include compositions and methods suitable for use in removing plaque biofilm from surfaces on and between teeth, and for providing other oral health benefits. The composition can be referred to as an oral hygiene composition.

BACKGROUND OF THE INVENTION

In the mouth, bacteria synthesize polysaccharides and proteins and create a scaffold matrix structure, in which they become embedded, thus creating what is known as oral biofilm, plaque-biofilm or dental plaque, which forms on teeth between brushings. Black, G. V., a researcher and a founder of modem dentistry (1836-1916), characterized dental plaque as a soft, mucinous, sticky, water insoluble material, which forms on teeth. Plaque remains soft and sticky for about a week or so, after which it gradually mineralizes, hardens (presumably as tartar) and becomes firmly affixed to the tooth surface and is normally referred to as tartar or calculus. Thereafter, it can only be removed with difficulty using instrumentation (Pader, M: Oral Hygiene Products and Practice (Marcel Dekker, Inc. NY), Chapter 4, Dental Plaque, pages 45-46).

Although one might think that the consistency of plaque biofilm would make it easy to remove completely from teeth, the physical removal of biofilm from tooth surfaces is actually not as easy as one might expect. Much of the difficulty is associated with getting access to the plaque, which builds up in difficult-to-reach areas, for example in fissures, at the gum-line where the tooth emerges from the gums and in areas between adjacent teeth (interproximal spaces). Another difficulty is in overcoming the surface tension forces between the water-insoluble biofilm and the tooth surface. Additional hindrance to removal, results from the binding of bacterial adhesins in biofilm to the lectins on the tooth surfaces and tooth pellicle. (Kolenbrander P & London J: Adherence Today, Here Tomorrow: Oral Bacterial Adherence. Journal of Bacteriology 1993; 175 (11):3247-3252).

Other than eventually transforming into an unsightly mineral deposit (i.e., tartar, also known as calculus), on teeth, the presence of plaque-biofilm on teeth is undesirable because the bacteria that grow in plaque biofilm are often pathogenic and responsible for various oral diseases, such as dental caries, gingivitis and periodontitis. There is also growing evidence that various human systemic diseases, such as infective endocarditis, cardiovascular disease, arteriosclerosis, cerebrovascular diseases (i.e., diseases relating to the brain including Alzheimer's disease and dementia), diabetes, as well as many others, are associated with the presence of certain bacteria in oral plaque (Hiromichi Y et al. The Pathogenic Factors from Oral Streptococci for Systemic Diseases, Int J Mol Sci, 2919:20, 4571: 1-18). In addition, gram negative bacteria in biofilm produce endotoxins that induce clinical manifestations of infection, i.e., local and systemic inflammation. Hence, control of plaque biofilm in the mouth is important for maintaining both good oral health and satisfactory overall human systemic well-being.

While many dentifrices are claimed to reduce the amount of plaque-biofilm left on teeth, clinical analyses have shown that toothbrushing with a dentifrice generally does not actually increase the amount of plaque physically removed compared with brushing without a dentifrice. (See, for example: (1) Valkenburg C et al. Does Dentifrice Use Help to Remove Plaque? A Systematic Review. *J Clin Periodontol* 2016; (2) Jayakumar A et al: Indian J Dent Res 2010; 21(2): 213-217; (3) Zanata F B et al: Supragingival Plaque *Removal with and without Dentifrice*: A Randomized Controlled Clinical Trial Braz. Dent J 2012; 23(3): 235-240. (4) Paraskevas S et al: Additional Effect of Dentifrices on the Instant Efficacy of Toothbrushing, J of Periodontology, 2006; 77(9):1522-1572. There are several reasons for this ineffectiveness, including the lack of ingredients to penetrate, entrap and displace biofilm from difficult-to-access areas on and between teeth and at the gumline. Furthermore, the ingredients in conventional toothpastes are not specifically designed to bind to bacteria or biofilm to facilitate detachment from the tooth surface, and thereby to eliminate them from the mouth with the expectorant after brushing is completed.

One trend in oral care research has been advancements in the incorporation of antimicrobials into mouthwashes and dentifrices. It has been shown that appropriately designed antimicrobial formulations can reduce plaque-biofilm regrowth between brushings. In contrast, little if any, research seems to have been performed to make dentifrices more effective in physically displacing or removing plaque-biofilm from teeth during brushing or as a result of using oral rinses. As a result, 40% or 50% of the plaque present before brushing, usually remains on teeth immediately after brushing. Rinsing alone, as with a mouth rinse, is even less effective, because the forces applied during rinsing with a mouth rinse are relatively small and rinses are not designed to promote physical removal of plaque.

One problem for anti-microbial agents is that oral bacteria do not generally live as individual planktonic cells that would be highly vulnerable to removal. Instead, these organisms join with organisms of many other strains to build complex multispecies biofilm-sheltered communities. Within the biofilm, nourished by ingested human food, bacteria rapidly synthesize high molecular weight polysaccharides and glycoproteins, which form protective matrices around the bacteria. These structures severely limit the access of antimicrobials to the organisms embedded within the protective biofilm matrices, and hence a large proportion of the microbes on tooth surfaces survive toothbrushing and remain viable after toothbrushing even when an anti-microbial dentifrice is used. Furthermore, over time, bacteria at the exposed surface of biofilm become increasingly resistant to antimicrobial agents. As a result, the resistant organisms in biofilms can become less susceptible to antimicrobials than planktonic bacteria are, by a factor of as much as 1000. Therefore, the human health benefits of antimicrobial agents tend to be quite limited.

Furthermore, the increasing use of antimicrobial substances in personal care and health care products has become a major evolving concern, because of its potential to promote the development and proliferation of antibiotic and antimicrobial resistant strains of bacteria. As a result, there is significant anxiety that this could result in the spread of more difficult to treat human diseases. Indeed, for this reason, triclosan, a widely used antimicrobial in personal care products, was relatively recently removed from toothpastes in the USA. Stannous fluoride, a fluoridating agent, which has been used for many years, also has significant antimicrobial activity and is still employed in a number of toothpastes. Perhaps, this is because up to now, there has been no evidence demonstrating that stannous fluoride produces genotypic changes in bacteria leading to resistance development.

In contrast to the use of antimicrobials, physically removing more plaque biofilm during brushing would not only have an immediate effect on lessening the number of pathogens present, but also would reduce biofilm regrowth, because less plaque bacteria would be present for reseeding new growth in the mouth.

In general, it is desirable that a toothpaste have as many as possible of the following attributes: remove dental biofilm effectively whether diluted or not; avoids damaging teeth; provides fluoride ions; and has pleasant esthetic properties (taste, mouth feel, etc.).

Accordingly, the availability of a toothpaste, oral rinse or other oral care compositions in various dosage forms, which promotes physical removal of plaque biofilm, would be highly desirable. Also desirable would be a showing that a product is more effective in reducing the net amount of plaque left on teeth between brushings.

SUMMARY OF THE INVENTION

The oral care compositions disclosed herein are intended to administer effective amounts of plaque-dislodging components to promote the physical displacement and removal of plaque biofilm from teeth when applied together with kinetic physical forces, such as tooth brushing. The oral care compositions can be referred to as oral hygiene compositions. The reference to hygiene indicates that the composition is conducive to maintaining health and, if possible, avoiding disease and decay, by enhancing cleanliness.

Compositions with these embodiments, comprise at least some of the following: (1) An oral plaque-biofilm-removing, water-insoluble, hydratable or partially hydratable, natural or synthetic, fibrillated, micro-fibrillated or nanofibrillated, essentially non-abrasive, polymer or network forming polymer, which swells and thickens in a carrier liquid, optionally together with one or more of the following additional plaque removing components; (2) A particulate, water-insoluble, micro-crystalline cellulose (MCC), silicified micro-crystalline cellulose (SMCC) or other organic or inorganic particles; (3) A synthetic particulate cross-linked Super Absorbent Polymer (SAP), or a Natural, particulate, non-cross-linked Superabsorbent Polymer, which swells and thickens in an aqueous medium; (4) A water-insoluble, nano-crystalline cellulose polymer (CNC) derived, for example, by acidification or oxidation of a natural or synthetic cellulose; (5) A water-soluble, organic, polymeric, thickener (PT), selected from one or more of the following: an alkali metal or ammonium salt of a polyacrylic acid, an alkali metal or ammonium alginate salt, xanthan gum, guar gum, carrageenan gum, sodium carboxymethyl cellulose, hydroxymethyl cellulose, hydroxypropyl methyl cellulose, hydroxyethyl cellulose, hydroxypropyl cellulose; (6) A natural or synthetic water-insoluble powdered cellulose (CP); and where the polymers form a 3D, entangled viscoelastic structure in an aqueous medium containing at least 10% of a humectant and which dislodges and removes plaque-biofilm from teeth. The composition's ingredients are mixed, dispersed, suspended or dissolved in carrier ingredients, which will vary depending on the type of oral composition and its desired characteristics or dosage forms. The components of these embodiments may be mixed, dispersed, suspended, emulsified or dissolved in a liquid carrier, or more generally any of various forms of carrier. The carrier liquid may include a humectant or a mixture of humectants.

Other embodiments can include, in any combination, any of various performance-broadening ingredients, which can address specific oral care needs of some users, as described elsewhere herein.

It has been found that when these compositions are brushed across the tooth surface, they increase the removal of biofilms by the toothbrush. In contrast, conventional toothpastes are generally ineffective in improving biofilm removal by the toothbrush when applied under similar conditions. Increased plaque-biofilm removal results in greatly improved oral health with less disease. Removal of plaque biofilm from teeth by regularly brushing with compositions of the invention will reduce gingival inflammation, prevent sub-gingival pocket formation, render the gum to be tightly adhering to teeth, decrease or eliminate bleeding gums and counteract bacterial challenges leading to tooth demineralization, tooth decay and tooth loss due to dental caries. Importantly, antimicrobial agents are not needed in these dentifrices, although they can also be used in some compositions.

The incorporated-by reference include Nonprovisional patent application U.S. Ser. No. 17/062,424 filed Oct. 2, 2020, discloses various useful oral care compositions. However, that disclosure does not appreciate the benefit of using a significantly greater amount of humectant, such as greater than about 5 wt. % humectant concentrations based on the weight of the composition. In regard to the presence of significant concentrations of humectant, it has been found that fibrils occupy a configuration or morphology that is different from what is seen with a water-dominated carrier liquid. It is observed that in the presence of a high humectant concentration, the fibrils become well-distributed, whereas in a mainly-water carrier liquid, there is some tendency for the fibrils to clump together It is found that the humectant changes the structure of composition (compared to compositions having a mostly-water carrier liquid), promotes "fluffiness," of the fibrillated material and promotes uniformity of distribution of the fibrils, and aids entanglement. It is believed that, in embodiments of the invention, the spread-out nature of fibrils in a high-humectant carrier liquid is conducive to entanglement of fibrils with other fibrils and to trapping of various kinds of particles in the entangled network formed by the fibrils. This entanglement and trapping is believed to help achieve better removal of plaque biofilm and other undesirable matter.

Also disclosed herein are embodiments in which SuperAbsorbent Polymer is present in the composition, and the amount of water present in the as-manufactured composition is such that the SuperAbsorbent Polymer retains further ability to absorb water such as saliva, which, if not absorbed by the SAP particles, might cause dilution of the network during toothbrushing.

BRIEF DESCRIPTION OF THE DRAWINGS

Aspects of embodiments of the invention may be further understood, but in no way are limited, by the illustrations herein.

DETAILED DESCRIPTION OF THE INVENTION

General Concepts and Definitions

Figure 1B:
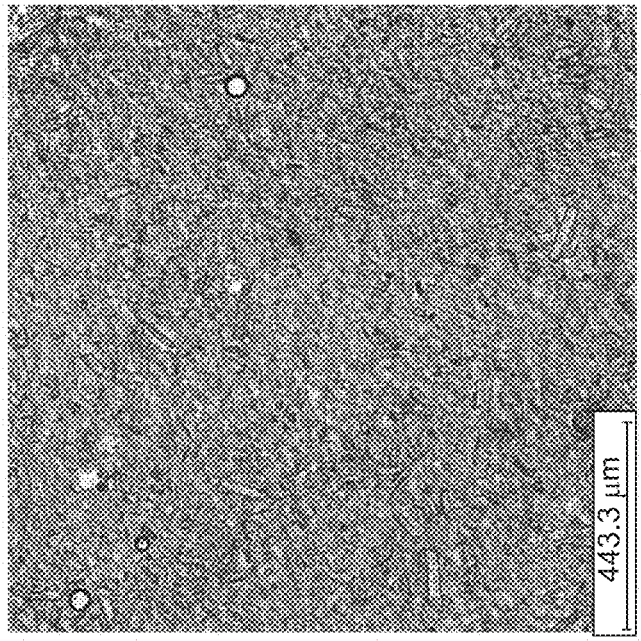
FIG. 1B is a micrograph showing a composition similar to an embodiment of the invention, in which microfibrillated material is dispersed in a water-glycerol mixture, showing a dispersal that is quite uniform.

The term concentration as used herein refers to concentration by weight % of ingredient in the composition. Water concentration in the composition includes all water present in the composition, whether it was introduced as water or as part of a sorbitol 70 solution (a condition in which sorbitol is often supplied) or as part of microfibrillated cellulose (which is often supplied in the form of a paste or suspension rather than completely dry). Fractional dilution refers to an amount of commercial toothpaste or an intended formulation, combined with an amount of water. For example, herein, 25% dilution means that the final diluted toothpaste contains 25% the original composition and 75% additional water.

In embodiments of the invention, the composition may comprise a plurality of fibers that form an entangled network. When the composition flows or moves or is caused to flow or move, the entangled fibers of the network move so as to bring along other fibers of the network or even other parts of the same fiber. Other solids that are contained within the network similarly may be brought along. It is believed that as a toothbrush moves over the surface the toothbrush applies normal force that promotes contact of the fibers and solids with biofilm or other surface-contacting substances, so as to facilitate the removal of such substances from the tooth or other surface. Also, motion of the toothbrush creates a shear stress during flow. In embodiments, the fibers may be either non-fibrillated or fibrillated.

In embodiments of the invention, compositions may comprise fibers or fibrils that are fibrillated, in which smaller fibrils branch off from larger fibers. Such fibers based on natural or synthetic microfibrillated or fibrillated cellulose or other forms of polysaccharides or other cellulosic or non-cellulosic polymers which form an entangled, interconnected or joined three-dimensional network structure. The joined entities forming the network can be fibers and fibrils and can be a network-forming material as provided elsewhere herein.

Other solids may also be present. Also, there may be a liquid vehicle having ingredients and properties as described herein.

Compositions of embodiments of the invention are intended to provide a viscoelastic oral care composition, such as a toothpaste that helps deliver the plaque dislodging and removing ingredients to the biofilm being removed. Compositions of embodiments of the invention have a yield stress and have an elastic modulus or storage modulus and a loss modulus even when diluted as described herein. It has been found that when these compositions are caused to flow over a surface, they remove biofilms. In contrast, prior art oral care compositions, such as commercial toothpastes, were found to be ineffective when used under similar conditions. Embodiments of the compositions are expected to significantly improve oral hygiene and reduce gingivitis, tooth decay and tooth loss. It is believed that the operating mechanism of a network of fibrillated material in removing biofilms is not present in conventional toothpastes.

In connection with work described herein, it has been found that measurements of rheology and tribology of candidate compositions are useful in the development of formulations and compositions of the invention. However, compositions having identical rheology and tribology do not necessarily clean identically. In particular, compositions of embodiments of the invention clean better than conventional toothpastes having the same or closely similar rheological and tribological properties. In other words, satisfying the requirements of rheology and tribology of the composition before and after dilution may be considered necessary but not sufficient to remove plaque biofilm, and certain ingredients in the composition are required to make effective compositions according to the invention.

In general, compositions of embodiments of the invention may comprise ingredients of various different categories. In the following, description is given of categories of ingredients that are sometimes found in prior art toothpastes or that may be present in embodiments of the invention.

Fibrillated Material

Embodiments of the invention comprise material that may form an entangled network. The network is believed to be effective to contribute to the rheological properties described herein, and is believed to contribute to effectiveness in removing dental plaque, even in diluted form such as during brushing where a significant dilution by saliva takes place. In embodiments, the network may contain fibers that are entangled with each other.

In embodiments, the Minute Fibrils may be fibrillated, meaning that they comprise thicker fibrils, from which branch thinner fibrils. In embodiments, the thinner fibrils, by being entangled, may be part of the entangled network. The thinner fibrils may remain attached to the thicker fibrils, such as attached at one end while the other end of the fibril is unattached. Other configurations are also possible. Unattached discrete fibers or fibrils may also be present.

The terms MicroFibrillated Cellulose and NanoFibrillated Cellulose are sometimes used interchangeably, and herein both terms are intended to be interchangeable and to be included in the meaning of the term Minute Fibrils.

In embodiments, the Minute Fibrils may comprise a polysaccharide. In embodiments, the Minute Fibrils may comprise cellulose. Cellulose is a polysaccharide that is created by plants, and also is created by bacteria or other organisms including fungi. Chemically, cellulose comprises polymeric chains of cellobiose dimers, which each comprise two glucose units. The cellobiose units are connected through beta-(1-4) linkages to form long chain polymeric molecules containing up to several thousand cellobiose units. The long polymeric chains form a three-dimensional macro-network of cellulose fiber chains, which have a mixture of amorphous and crystalline regions. By amorphous, we mean that the polymer constituents are highly disordered. In contrast "crystalline cellulose refers to cellulose chains, which are highly regular and ordered. With reference to crystalline cellulose, its crystallinity should not be confused with the type of crystallinity found, for example, in a crystalline inorganic salt. Crystalline salts are rigidly held together by strong attractive ionic forces. As a result, ionic crystalline salts are formed into hard, highly ordered, essentially immobile, ionic crystal matrices. While crystalline cellulose is quite well ordered, its structure is not ionic and the polymeric cells, i.e., individual cellobiose units, are held together by somewhat elastic hydrogen or covalent bonds. As a result, while "crystalline" organic polymers, are more "rigid" than amorphous organic polymers, they are still more flexible than inorganic crystalline salts and they remain somewhat mobile. From a macroscopic standpoint, crystalline salts appear as hard solid particles, while microcrystalline cellulose is softer and more fabric-like. Of importance to the performance of microfibrillated cellulose for plaque-biofilm removal, the flexible fibrils and microfibrils on cellulose fibers, absorb water, expand and form an entangled flexible, network structure when added to an aqueous medium. In addition to trapping plaque and removing it from surfaces, the structure is believed to importantly contribute to the mechanical properties of the composition, which ensures that the applied forces of brushing or rinsing, reach and dislodge the plaque-biofilm from surface of teeth and elsewhere in the oral cavity.

While the vast majority of cellulose used in the world is derived from plants, it is worthwhile mentioning that some cellulose is obtained from or is excreted by bacteria, and is referred to as bacterial cellulose. Such cellulose typically has dimensions smaller than the dimensions of other types of cellulose described herein. Bacterial cellulose may be used in embodiments of the invention.

Fibrillated cellulose as described here can be made from any of various types of wood or plants. MFC can be of plant origin such as that made by Borregaard (Sarpsborg, Norway), Weidmann Fiber Technology (Rapperswil-Jona, Switzerland) and many other manufacturers in many countries. The Borregaard material, which is sold under the tradename "Exilva," is made from Norwegian Spruce. The Weidmann material, which is marketed under the tradename "Celova," is made from Swiss Birch. Cellulose products are also available from Sappi (Boston, MA, USA). The Sappi microfibrillated cellulose is made from wood pulp and other natural sources. In general, the material is not limited by species of tree or plant. Dimensions of the fibrillated cellulose that can be used in the present composition are provided in Tables 1 and 2 in U.S. Pat. No. 10,266,793. Tables 1 and 2 from U.S. Pat. No. 10,266,792 are reproduced below as Tables 1A and 1B.

Materials made by Borregaard have subclassifications including:

TABLE 1A

| Sub-Grade | Mean Elydrodynamic size | Size Range |
|---|---|---|
| Exilva Forte | ~20 micron | ~1 to ~1000 micron |
| Exilva Piano (various grades) | ~36 to ~60 micron | ~1 to ~1000 micron |
| Exilva Piano Light | ~70 micron | ~1 to ~1000 micron |
| Sensifi (in admixture with CMC) | ~100 micron | ~1 to ~1000 micron |

As analyzed by numerous SEMs at several magnifications, some illustrative cellulosic Minute Fibrils have the following features:

TABLE 1B

| Microfibrillated | Fibers (Type B) | | Fibrils (Type A) | |
|---|---|---|---|---|
| Cellulose | Diameter | Length | Diameter | Length |
| Exilva Forte | 0.5-3 µm | 10-100 µm | 30-60 nm | >2 µm |
| Exilva Piano | 0.1-20 µm | 5-150 µm | 50-70 nm | 2-3 µm |
| Exilva Piano Light | 0.3-20 µm | 20-200 µm | 20-75 nm | 1-5 µm |
| Sensefi | 0.25-15 µm | 5-60 µm | 30-60 nm | 0.4-1.0 µm |

It may be preferable to process the wood or other plant-based source of cellulose to form MFC using processes that are purely mechanical, without the use of chemicals. Alternatively, some other acceptable processes for making MFC may include exposing the material to enzymes or other chemical compounds that can be washed out after processing. Both types of processing can be used in combination.

A particularly preferred fibrillated polysaccharide component is micro-fibrillated cellulose (MFC), which can be prepared from wood cellulose pulp fibers by opening and separating its fibers and microfibrils. It should be noted that the terms micro-fibrillated cellulose and nano-fibrillated cellulose are sometimes used interchangeably. When we refer to micro-fibrillated cellulose or Minute Fibrils, we also mean to include nano-fibrillated cellulose. Other cellulose sources and mechanical, chemical, bacterial, biological or enzymatic processes can also be used in making the composition of embodiments.

Fibrillated and micro-fibrillated polysaccharides other than cellulosic polymers, and other non-cellulosic polymers (irrespective of their size) can also be used as the micro-fibrillated plaque-dislodging polymer, providing they are essentially water-insoluble. In addition to wood/plant sources of MFC, other suitable natural polysaccharides include ground peanut shells, corn cobs, and ground hay or straw, which may contain mixtures of water-insoluble polysaccharides such as cellulose, hemicellulose and lignin. Also, it is possible to use chitosan or its derivatives, which is another form of polysaccharide. U.S. Pat. No. 6,602,994 (EP 845495 and JP 59-84938) refers to the formation of an insoluble micro-fibrillated polymer made by the homogenization of chitosan flakes. Such a microfibrillated polysaccharide would be suitable for preparing embodiments of the composition. In still other embodiments of the invention, the fibrillated material could comprise still other polysaccharides other than cellulose. Other fibrillated material may also include those made from polyethylene, polypropylene, polyester, nylons, amides or any synthetic polymer. These may be used either alone or in combination with other Minute Fibril materials. At least one version of the wood-sourced material is approved by the United States FDA as a food or being GRAS (i.e., Generally Recognized as Safe).

For example, suitable starting materials can include a broad range of polysaccharides. The resulting fibrous materials are similar in structure and size to the fibrillated and micro-fibrillated cellulosic materials described above and hence are effective in plaque biofilm-removing embodiments described herein. The water-insolubility of micro-fibrillated polysaccharides can be confirmed by suspending the ingredient at a concentration of 1-5% in distilled water or other solvents such as glycols or the like, and examining the suspension under a microscope as described in U.S. Pat. No. 6,602,994, or by measuring the rheology and tribology of the resulting materials and its response to dilution as described elsewhere herein.

Yet another possibility for embodiments of the invention is that the Minute Fibrils may be or may comprise cellulose that is of bacterial or microorganism origin. Such cellulose may provide biocompatible fibrillated material that may be used alone or mixed with other fiber-based materials to form the network of the present invention. Typically, fibers of such cellulose typically have smaller cross-sectional dimensions and other detailed microstructural features than the fibers that are fibrillated from plant-based starting materials.

As yet another alternative, the fibrillated material can be also non-cellulosic such as material made from synthetic or man-made polymers such as flocked nylon or polyester, polyolefins, acrylic or other polymers. The fibrillated materials may be made by the Viscose or Lyocell process, in which fibers are spun from cellulose-based polymers or other synthetic polymer materials dissolved in special solvents. Such fibers are produced, for example, by Engineered Fibers Technology (Shelton, CT, USA).

Still other possible microstructural network forming materials that can be used to make the inventive compositions include the following:

i) Polypropylene fibrils see article by Rizvi et al. (2014) Dispersed polypropylene fibrils improve the foaming ability of a polyethylene matrix. Polymer, 55 (16), 4199-4205.

ii) Proteins Fibrils, see for example Adamcik, J., & Mezzenga, R. (2012). Proteins fibrils from a polymer physics perspective. Macromolecules, 45(3), 1137-1150. In their specific example/protein, to be used at 5% wt and beyond iii) Amyloid fibrils, see Volpatti, L. R., & Knowles, T. P. (2014). Polymer physics inspired approaches for the study of the mechanical properties of amyloid fibrils. Journal of Polymer Science Part B: Polymer Physics, 52(4), 281-292.

iv) Fibrillated holocellulose see Yang, X., & Berglund, L. A. (2020). Structural and Ecofriendly Holocellulose Materials from Wood: Microscale Fibers and Nanoscale Fibrils. Advanced Materials, 2001118.

v) Fibrillated block copolymers, see Hammer, B. A., Bokel, F. A., Hayward, R. C., & Emrick, T. (2011). Cross-linked conjugated polymer fibrils: robust nanowires from functional polythiophene diblock copolymers. Chemistry of Materials, 23(18), 4250-4256.

vi) Collagen fibrils, see Van Der Rijt, J. A., Van Der Werf, K. O., Bennink, M. L., Dijkstra, P. J., & Feijen, J. (2006). Micromechanical testing of individual collagen fibrils. Macromolecular bioscience, 6(9), 697-702.

vii) methylcellulose fibrils, see Morozova, S. (2020). Methylcellulose fibrils: a mini review. Polymer International, 69(2), 125-130.
viii) Fibers made from alginates by crosslinking with multivalent ions as is known in polymer chemistry.
ix) Fibers and networks made mixing polymers such as methyl cellulose and hydroxyethyl cellulose using nanoparticles as a crosslinking agent by either ionic or hydrogen bonding.
x) Fibers and networks that are made by ionic, acid-base, or hydrogen bonding or by crosslinking of polymer molecules.
xi) Fibers and networks made by mixing polymers and ions to form coacervates; ions may include borates or other ions as is known in polymer chemistry.
xii) Any combination of the above alternate routes for making fiber and networks.

Still other possible microstructural network forming materials that can be used to make the inventive compositions include the following:

i) Chitosan (concentration between 0.1% to 10%, preferably between 0.3 and 8%) and particles like MCC or abrasive silica.
ii) Chitosan (concentration between 0.1% to 10%). Mechanical properties changing depending on the pH.
iii) Synthetic micro-sized biocompatible flexible fibers, fibrillated or not, made of PEG or PEG-DA through chemical/UV-photo-activated cross-linking. See article by Perazzo et al. (2017). Flow-induced gelation of microfiber suspensions. Proceedings of the National Academy of Sciences, 114(41), E8557-E8564.
iv) Dual networks of polymer hydrogels. See examples of polymers from JP Gong papers. Though concentrations must be modified because they produced stiff gels, while here we want to use smaller elastic modulus.
v) Interpenetrated polymer networks. See examples provided by JP Gong
vi) Interpenetrated polymer networks made of chemically linked by colloidal silica nanoparticles: example hydroxyethylcellulose (Mv ~1,300 or 720 kDa;) and/or methylcellulose (Mv ~90 or 60 kDa; Sigma) in water (1-20 mg/mL) with stirring and mild heating. Colloidal silica nanoparticles at about 1-30% wt [Ludox TM-50; D~15 nm] then (150 mL) of the HEC and MC solution is mixed with the colloidal nanosilica solution (300 mL). See paper by Anthony, C. Yu, et al. "Scalable manufacturing of biomimetic moldable hydrogels for industrial applications." *Proceedings of the National Academy of Sciences* 113.50 (2016): 14255-14260.
vii) Cellulose nanocrystal suspensions and related pH effects see Tony examples
viii) Laponite based gels and other clay systems see Au, P. I., Hassan, S., Liu, J., & Leong, Y. K. (2015). Behaviour of LAPONITE® gels: rheology, ageing, pH effect and phase state in the presence of dispersant. *Chemical Engineering Research and Design*, 101, 65-73.
ix) Polyelectrolyte coacervates/complexes, i.e., mixture of positively charged and negatively charged polyelectrolytes
x) PVA acrylic acids cross-linked by borates or Zr. See examples on paper by Perazzo et al, *Advances in Colloid and Interface Sciences*, 2018
xi) Polyelectrolyte plus salts/multivalent salts such as Y or Al
xii) Surfactant plus polyelectrolyte complexes.
xiii) Surfactant worm-like micelles such as combination of CpyCl surfactant and NaCl or CTAB surfactant and NaCl or NaSal, see examples by Gaudino et al., Journal of Rheology, 2015
xiv) Emulsions, i.e., oil-water mixtures where on phase is present in forms of droplet dispersed into the other phase. Stabilized by surfactants or mixture of them, as the ones mentioned in the surfactant list for toothpaste.
xv) Bicontinuous emulsions, i.e., oil-water mixtures where on phase is compenetrated/percolated into/though the other phase. Stabilized by surfactants or mixture of them, as the ones mentioned in the surfactant list for toothpaste.
xvi) Nanoemulsions, i.e., emulsions with droplet size smaller than 200 nm.
xvii) Microemulsions, i.e., thermodynamically stable emulsions where the interfacial tension is close to zero
xviii) Pickering emulsions, i.e., emulsions stabilized by colloidal particles or fibers.
xix) Bijels. Compenetrated immiscible gel phases mostly stabilized by colloidal particles.

Linear or branched worm-like surfactant micelles ranging from about 0.1 nm in to 100 nm in diameter and having an aspect ratio of more than 2, such as for example those made with: a) combinations of cetylpyridinium chloride surfactant and an electrolyte/salt such sodium chloride (e.g. NaCl); b) cetyltrimethylammonium bromide (CTAB) surfactant and NaCl, or c) activated by a pH change and/or electrolyte can be used as network-forming compositions according to the present invention. Examples for making worm-like micelle (WLM) structure is described by Dreiss, *Soft Matter* 2007; Chu et al. (2013). Smart wormlike micelles. *Chemical Society Reviews*, 42(17), 7174-7203; Dreiss, C. A., & Feng, Y. (Eds.). (2017). *Wormlike Micelles: Advances in Systems, Characterisation and Applications. Royal Society of Chemistry*; Gaudino et al., Journal of Rheology, 2015

While there are several effective ways to fibrillate cellulose, a preferred method involves passing the cellulose pulp fiber source material several times through a special high-shear or impact generating homogenizer or microfluidizer (see, for example methods of Turbak et al. in U.S. Pat. Nos. 4,341,807; 4,374,702; 4,378,381; and 4,500,546).

In embodiments, the fibrillated materials can be surface modified by physical means such as adsorption of a surfactant, an ion, a polyelectrolyte, a molecule or a polymer or can be chemically modified to introduce special functional groups to the surface of the fibers and fibrils. The MFC may be functionalized such as by oxidation as by the TEMPO manufacturing process or by other chemical reactions including amidation, amination, hydrophobization or the like, if desired. (A Review on Surface-Functionalized Cellulosic Nanostructures as Biocompatible Antibacterial Materials; Tavakolian, et al., Nano-Micro Lett. (2020) 12:73) The modification processes maybe through physical adsorption, or through a chemical reaction to introduce special functional groups into the surfaces of the fibers and fibrils. Some cellulosic materials may be material having amine cationic groupings, which makes them likely to provide anti-microbial activity to dentifrice compositions containing this ingredient. Cellulose polysaccharides can be "derivatized" and micro-fibrillated, as described in the same US Patent (U.S. Pat. No. 6,602,994 to Cash). By "derivatized" we mean imparted with functionality either before or after being micro-fibrillated to produce the desired forms similar to microfibrillated cellulose. Non-cellulosic polymers capable of becoming fibrillated are also available, although they are less commonly available from natural sources than cellulose.

In regard to dimensions, the thicker fibrils of MFC may have a diameter between about 0.1 µm to about 25 µm and preferably from about 0.25 µm to about 20 µm or larger. The thinner fibrils may have a diameter between about 250 nanometers to about 20 microns. As described in US20180078484, in particular embodiments, the average MFC fibril length may be from 100 nm to 50 µm, preferably from 500 nm to 25 µm, more preferably from 1 µm to 10 µm, most preferably from 3 µm to 10 µm. In particular embodiments, the average MFC fibril diameter may be from 1 nm to 500 nm, preferably from 5 nm to 100 nm, more preferably from 10 nm to 50 nm, most preferably from 10 nm to 30 nm. For dentifrices of this embodiment, an average mean particle size (which may be determined by laser diffraction) should be between about 10 µm and about 150 µm, more preferably between about 20 µm and 100 µm. These dimensions can be modified as required by varying the production process parameters such as the number of passes of the cellulose pulp fibers through the refiner and the microfluidizer/grinder/milling devices or similar equipment. The dimensions of the resulting fibrils may be tailored depending on the degree of fibrillation as dictated by the amount of mechanical energy used to fibrillate the source fibers, for example the number of passes through the microfluidizer machine, as is known in the art of making micro- and nanofibrillated cellulose.

The desirable MFC may have a high degree of fibrillation, which is a function of the number of passes through the microfluidizer, the gap size used and the pressure of fluidization. A number of passes of about 5 passes or more than 5 passes may be recommended, more preferably from 5 to 15 passes. The degree of fibrillation can be assessed by: a) number and size fibrils made from source fiber; b) hydrodynamic size as determined in a dilute state by laser diffraction; c) the viscosity and rheology of the resulting structure in water or in ethylene glycol; d) water holding capacity as determined by centrifugation at, for example, 3,000 to 10,000 g; e) specific surface area expressed in m2/g as measured by the BET (Brunauer-Emmett-Teller) method. The average hydrodynamic size as determined by laser diffraction may be from 5 µm to 100 µm depending on the degree filtration and preferably from 20 to 70 µm. The size distribution as determined by laser diffraction may include particles up to 100 µm or 200 µm or even close to 1 mm. It should be noted that the hydrodynamic size may be that of flocs formed by aggregation of a number of fibrillated entities. The specific surface area, as measured according to the BET method, may be from 50 m2/g to 300 m2/g or even 500 m2/g. The viscosity of a 2% by weight concentration of MFC in water may be from 10,000 to 50,000 mPa-s when measured with a Brookfield viscometer using the V73 spindle at 10 rpm after 5 minutes.

It can be noted that materials such as fibrillated cellulose have a property of being able to hold or retain water among the fibrils. The desirable MFCs or polysaccharides for dentifrices have a high degree of fibrillation and a water holding capacity, such as from about 20 g/g to about 300 g/g (grams of distilled water per gram of dry MFC), preferably from about 50 g/g to about 150 g/g (available from Borregaard). Measurement of water holding capacity is described in US20180078484. Commercially, micro-fibrillated cellulose is typically shipped in the form of a stable paste containing from about 9% to about 11% micro-fibrillated cellulose in water; some other suppliers can provide MFC concentrations pastes of up to 30% to 35% concentration. This is because if water was removed from MFC until the product was completely dry, the drying would decrease the ability of the MFC ability to re-disperse in water. Related to this, if MFC that has been fully dried and then redispersed in water, the viscosity and other rheological parameters of that MFC in liquid are much lower or inferior, compared to the properties that existed before the MFC was dried. We note that the use of humectants prevents irreversible aggregation or hornification of cellulose fiber and fibrils upon drying, and this could be used to allow the creation of microfibrillated cellulose having little or no water content, without causing break-up or damage of the fibers or fibrils. This could be used in making compositions for oral use such as for chewing gum or other applications. U.S. Pat. No. 4,481,077 describes drying and redispersion of fibrillated material.

The specific surface area of MFC, may be characterized by the BET (Brunauer-Emmett-Teller) method. The specific surface area of the MFC may be chosen to be in the range from between about 10 $m^2/g$ to about 500 $m^2/g$, preferably from about 50 $m^2/g$ to about 350 $m^2/g$. In general, MFC with a larger specific surface area will provide a higher aqueous solution viscosity, higher G', higher yield stress, greater absorption, increased binding of biofilm, and hence better plaque and soil removal. Furthermore, a larger specific surface area indicates that the MFC will be more resistant to loss of viscosity due aqueous dilution such as due to incoming saliva during brushing. Hence, one disadvantage of this increase of solution viscosity with increasing specific surface area can be the inability to formulate compositions containing very high concentrations of MFC, which would result in compositions that are extremely thick (viscous) and difficult to dispense.

It is known that materials such as MFC experience a process called activation upon being subjected to high shear or torque, which can be obtained with a homogenizer. Activation causes entanglement of the Minute Fibrils to form the inventive entangled networks present in compositions of embodiments of the invention. For small batches, we used an Ultra Turrax T25 homogenizer (available from IKA Works, Inc., Wilmington, NC) With this homogenizer we used the following dispersing head model numbers: S25N-18G; S25N-25F; and S25 KV-25F. Typical rotational speeds and durations of homogenization were 10,000 to 20,000 rpm and 10 to 30 minutes or until equilibrium rheological properties are obtained. For larger batches, we used a Ross homogenizer (Charles Ross & Son Company, Hauppauge, NY) or other equivalent equipment.

As discussed elsewhere herein, it may be advantageous for there to be a considerable degree of entanglement of the Minute Fibrils with each other, which may produce a better cleaning interaction when applied to surfaces. It is believed that the mechanical shearing or homogenization during activation of the inventive composition encourages and increases entanglement of the fibrils. Thus, in order to describe a composition of an embodiment of the invention, one may describe not just chemical composition and dimensions or dimensional distribution of the fibrils, but also the extent of entanglement as a result of manufacturing processes. During manufacture of the described composition of embodiments of the invention, the entangled network of the inventive composition may be formed by homogenizing MFC and possibly other ingredients in the presence of water, water-humectant mixtures or more generally liquid, under shear so as to form physical entanglements.

Such activation process may be a process that is distinct and separate from the process used in fibrillating the material. The activation process may be performed after the fibrillation process. Other manufacturing, mixing or processing steps may be performed in between.

It is believed that, due to its interconnected entangled microstructure, MFC does not shed fibers, fibrils or particles when diluted in water as can occur during brushing, rinsing or cleaning. Such physical entanglements resist being unraveled by dilution when the composition is later used in the mouth. Resisting being unraveled by dilution is a property of compositions of embodiments of the invention, in contrast with the behavior of commercial toothpastes that are made with polymeric thickener (mainly macromolecules and particles). Such commercial toothpastes readily fall apart and disassemble into slurries when they experience even slight dilution by water or saliva.

Other Fibrous Material

It is also possible, in embodiments of the invention, that the fibrils may be simple fibers that are non-fibrillated. In such case, the fibers may be sufficiently long, as described by an aspect ratio, and appropriately processed, to form an entangled network.

Non-Fibrous Solid Material

In an embodiment of the invention, the composition may include non-fibrous solids or non-fibrillated solids. Such ingredients, which may be particles or particulates, may modify rheology, tribology, and microstructure and can impact physical, mechanical or chemical properties of the composition so that it can remove biofilm, stain, residues or other substances from teeth and the oral cavity. Such ingredients also may produce effects such as whitening or lowering sensitivity or other desirable attributes as described elsewhere herein. Materials that can be in the category of non-fibrillated solid material includes MicroCrystalline Cellulose and abrasives, and other types of solids. In general, they can be used in any combination and in any concentration.

Frictional interaction with the surface being cleaned can be created by either or both of, the fibers and fibrils of the fibrillated material, and other solids that may be present in the composition. If these other solids resemble fibers, such fibers may be unbranched in contrast to the fibrillated material described elsewhere herein, or they may be less branched than the fibrillated material. It is believed that these solids may contribute to plaque and stain removal by the composition. Such solids have been shown to synergize with the network of polymeric fibers in displacing plaque biofilm during brushing. These particulate solids may be one or more natural or synthetic, non-scratching, water-insoluble, particles, fibers or fibrils, which may for example be polysaccharide.

Microcrystalline Cellulose

A useful type of additional solid is a non-fibrillated, particulate, water-insoluble micro-crystalline cellulose (MCC). Chemically, MCC is similar to MFC or cellulose in general, in that it consists of polymeric chains of dimeric cellobiose. The primary chemical difference between MCC and MFC is the significantly higher content of cellulose in crystalline form in MCC. Also, from a physical standpoint, in contrast to MFC, the cellulose strands or macrofibrils in MCC are not fibrillated. As a result, although the MCC particles do not have high hardness, they are more rigid or more stiff (with respect to bending) than is fibrillated forms of cellulose, and are suitable for enhancing rheology and applying mild frictional forces to wipe or mop the plaque biofilm from tooth surfaces. The long, highly flexible fibrils of MFC may be suited to reaching into inaccessible areas and entrapping plaque biofilm and dislodging it.

Included in the category of micro-crystalline cellulose (MCC), is silicified micro-crystalline cellulose (SMCC), which contains particles containing micro-crystalline cellulose coated or mixed with colloidal silicon dioxide (silica). SMCC performs the same function as MCC, i.e., to provide mild frictional forces to remove biofilm from tooth surfaces. However, MCC has a tendency to form particulate clusters or agglomerates, which do not always easily break down during preparation of the composition to form a smooth composition. SMCC provides a useful alternative that is more readily dispersed in a paste formulation. The most popular form of MCC is Avicel®, which was invented by FMC Corporation (Philadelphia, PA) and now is a product of Dow (Midland, MI). Various grades of MCC and SMCC also are available in the USA from JRS Pharma LP, (Patterson, NY) and are manufactured under the Trade names, Vivapur® MCC and Vitacel® MCC and Prosolv® SMCC. Vivapur MCC is available with average particles sizes between about 15μ and 250μ. For dentifrices of this embodiment, preferred particles sizes are between about 15μ and 125μ and also 200 um. Prosolv® SMCC is available with various average particle sizes between 50μ and 125μ. The average particle sizes of SMCC for these embodiments may be chosen to be between about 30μ and about 125μ, and preferably between 50μ and 100μ, more preferably between 60 and 80μ.

Particles such as MCC may be elongated or irregular shape. Such particles may have at least one dimension that is larger than 25 microns or larger than 50 microns (average). The size could be up to 200 microns or larger. Such particles may have an aspect ratio (ratio of maximum dimension to minimum dimension) that is larger than 2 or larger than 3. In embodiments of the invention, the concentration (w/w) of particles such as MCC or SMCC may be at least as large as the concentration (w/w) of Minute Fibrils, or may be at least half the concentration (w/w) of Minute Fibrils. In embodiments of the invention, the concentration (w/w) of MCC particles may be 0.2% (w/w) or more, or 0.5% or more, or 0.6% or more. In some embodiments, the concentration (w/w) of MCC particles is 1.2% (w/w) or less. In some cases, particles such as MCC at a concentration up to 5% or 10% may further modify the storage modulus or stiffness of the composition.

In some conventional commercial toothpastes MCC is known to be included, but it is believed that in those conventional commercial toothpastes the MCC is in the form of very small particles such as smaller than 25 microns or smaller than 50 microns or even can be in the form of what is referred to as colloidal MCC such as 3 or 4 microns or even smaller, and it is present at a small concentration. It is believed that in the commercial toothpastes, which are based on polymeric thickeners such as carboxymethylcellulose (CMC), the type of MCC that is used is unlikely to provide a wiping or biofilm removal effect, because of small particle size and low concentration.

Other organic or inorganic particles also can possibly be used. These other particles, including both organic particles and inorganic particles, can be used irrespective of their shape and sizes. Additional water-insoluble cellulosic materials which can be used are ground peanut shells, consisting primarily of cellulose and hemicellulose polysaccharides with some lignin (reference: Kerr J I, Windham W R, Woodward J H and Benner R: Chemical Composition and In-vitro Digestibility of Thermochemically Treated Peanut Hulls. J. Sci. Food Agric. 1986; 37: 632-636) are also useful in the enhancement of plaque-biofilm removal. Pulverized corn cobs, which comprise mixtures of cellulose, hemicellulose and lignin, can also be used (reference: Pointner M, Kuttner P, Obrlik T et al: Composition of comcobs as a substrate for fermentations of biofuels. Agronomy Research 2014; 12(2): 391-396). Ramie is another example of a natural material which provides useful particulate fibers, which can be extracted from the inner bark phloem of ramie plant stems and degummed. Useful fibrous materials can also be obtained from Jute, the Java tree, flax and abaca fiber, psyllium, and other sources.

In an embodiment of the invention, these solids can be entangled in the network created by the Minute Fibrils, and thus the solid particles might not exist as loose freely-moving individual particles, which is what occurs in the case of conventional commercial toothpaste where the particles quickly become loose in the form of slurry once they are diluted with saliva water in the mouth. The various types of particles of embodiment compositions, being a part of the network, are believed to contribute to removal of plaque and stain by interacting with plaque biofilm or stain, such as by scraping or by creating localized forces at the surface that further improve the removal of plaque biofilm and stain as described elsewhere herein.

If the concentration of abrasive particles is taken together with the concentration of various other kinds of particles, the total concentration of various kinds of particles may be up to 30% or higher by weight of the composition.

Other Forms of Cellulose

Another optional plaque dislodging ingredient in embodiments of this composition is a water insoluble nanocrystalline cellulose polymer or cellulose nanocrystals (CNC), which can be derived by combinations of mechanical, chemical and enzymatic treatment of cellulose (Johnsy G: Cellulose Nanocrystals: Synthesis, Functional Properties, and Applications. Nanotechnology, Science and Application 2015; 8: 47-54). Mechanical processes convert cellulose into micro-fibrillated cellulose, such as by micro-fluidization, ultrasonic treatment or homogenizations methods. As previously noted, micro-fibrillated and microcrystalline cellulose, consists of long chains of cellobiose units. Cellobiose is a dimer consisting of two glucose units. In natural cellulose, these disaccharides are formed into long polymeric cellobiose chains. Microfibrillated and other forms of cellulose can easily be modified into CNC by acid-hydrolysis to remove the amorphous regions and to convert them to crystalline cellulose, thereby increasing the crystalline cellulose content. This frequently shortens the micro-fibrils and hence the resulting cellulose is often referred to as nanocrystalline cellulose. CNC is characterized as being stiff rod-like particles with mostly a crystalline cellulose structure. The apparent stiffness of the shorter relatively stiff, rod-like fibers is presumably due to their short length. Aqueous slurries of CNC generally have lower viscosities and lower yield stress than MFC in aqueous systems. Due to CNC's stiffness and rigidity, CNC may contribute somewhat greater frictional forces for plaque biofilm removal from tooth surfaces; because of its smaller particle size CNC may readily flow in the InterProximal space and produce biofilm removal. Nevertheless, CNC particles are still very soft and are not abrasive to surfaces.

The dimensions of CNC can vary depending on the source of the CNC and the method of manufacture. CNC from acid hydrolyzed wood fibers can have a fibril length of between about 100 and 300 nm. The widths of these fibrils can be from about 3 to 5 nm. Acid hydrolyzed, bacterial-sourced CNC has fibril length between 100 nm and 1000 nm and a width between 10 nm to 50 nm.

Yet another optional plaque-dislodging ingredient in the composition is powdered cellulose (NPC) (available, for example, from JRS Pharma, Patterson, NY). Powdered cellulose is another ingredient that can provide very mild frictional forces that can enhance the removal plaque biofilm from surfaces. The particle size of these powdered cellulose particles and their amorphous content makes powdered cellulose able to enter and remove biofilm from tight spaces. Because powdered cellulose does not greatly expand in aqueous media, as well as because of its relatively low cost, it is possible to include larger concentrations of powdered cellulose than other polymeric plaque dislodging components in a formulation to help remove more plaque. This allows relatively large areas of the tooth surface to be wiped with each brush stroke. Powdered cellulose also does not have as much effect on the dentifrice viscosity as the other polymeric ingredients and hence it can be used at higher concentrations. Many sources of powdered cellulose are available with various particle sizes. The average particle size of the powdered cellulose used may be chosen to be from about 15 μm to about 150 μm, preferably from about 35 μm to about 100 μm, more preferably from about 50 μm to about 75 μm. Preferred toothpaste embodiments can contain between about 0.2% and about 25% of powdered cellulose, which can contribute to the rheological properties of the composition. The size of the ingredient matters in order for the ingredient to be able to enter the interproximal spaces.

Fibers, Fibrils, Network-Forming Materials and Comparison with Commercial Dentifrices Embodiment compositions comprise water-insoluble discrete fibers and fibrils that form a 3-D network structure. Said fibers and fibrils are much larger (in diameter and length) than the size of the water-soluble macromolecular polymeric thickeners used to make commercial dentifrices. Examples of the fibers and fibrils source of the inventive compositions include microfibrillated cellulose and other network-forming materials as described elsewhere herein.

Embodiment fibers and fibrils have a diameter larger than 5 nm, which may be the diameter of the smallest primary cellulose nanofibrils found in fibrillated microfibrillated or nano-fibrillated cellulose. In embodiment compositions, the fibers and fibrils can be much larger than 5 nm. The discrete fiber and fibrils of embodiments form an entangled and extended 3D network of flocs, bundles or domains. These entangled domains can be from 10 microns to more than 1000 microns in size when measured by laser diffraction at low concentration. These formed entangled domains may become interconnected or sintered and can form even larger extended structures as the concentration of the fibers and fibrils increases especially when activated or upon proper mixing. The normally become viscoelastic and are difficult to breakdown by dilution or when subjected to shear forces. The fibers and fibrils may or may not be branched to form the compositions of the invention.

The 3D network of the embodiment composition can delay or retard saliva-induced dilution and may hamper the microstructural network breakdown in the presence of water or saliva during brushing or cleaning as described herein. In contrast, commercial dentifrices are held together by short water-soluble polymer molecules (length 4-20 nm) which when diluted by water or saliva during brushing they easily lose their network structure and form low viscosity slurry as it is known in the art. This slurry may normally include abrasive particles suspended in low viscosity aqueous solution which may behave as a Newtonian fluid.

Abrasives

In general, abrasives are added to dentifrices as a means of preventing unsightly stain build-up on teeth. The teeth absorb stains, from colored organic substances in foods and drinks, on a daily basis. These stains become entrapped within proteinaceous pellicle, which is continuously formed in the mouth and deposited on teeth. Dentifrices contain mild abrasives, which are chosen to remove a thin layer of pellicle with much of the stain deposited each day. Some pellicle is left intentionally on the tooth surface to prevent abrasion to the underlying tooth. The pellicle layer gradually thickens over time and the degree of tooth staining increases until the layer of pellicle is about 10μ in thickness. At periodic semiannual visits to the dental office, the dental hygienist removes tartar build-up on teeth and polishes the teeth with an abrasive prophylaxis paste to removes the stained pellicle that formed since the previous visit. Thereby, the tooth whiteness is restored.

Teeth are composed of two types of mineral. The crown of the tooth comprises a hard exposed inorganic mineral, called enamel, and a softer inner organic root portion, known as dentin, which is encased in the enamel. The harder enamel layer ends just below the gum line and the root material below the enamel junction consists of the softer dentin. The gums recede with age exposing the softer dentin organic/mineral from about 30 years of age. As a result, the dentin tooth organic/mineral below the gum line becomes exposed and due to its lesser hardness is especially subject to abrasive damage during brushing. The abrasives chosen for dentifrices may be chosen to be sufficiently abrasive to remove stained pellicle but not so generally abrasive as to damage tooth enamel or dentin. There are several factors affecting the abrasivity of toothpastes including the hardness of the abrasive material, the shape of the abrasive particles, the size of the abrasive particles and the concentration of abrasive in the dentifrice. A useful summary can be found in Pader M: Oral Hygiene Products and Practice (1988) 231-266.

The softer dentin is more adversely affected by the possible abrasive effects of dentifrices than is enamel. The standard method of determining dentifrice abrasiveness is using the Relative Dentin Abrasion (RDA) procedure, which is based on the Radioactive Dentin Abrasion Method of Grabenstetter et al. (Grabenstetter R J et al., The measurement of the abrasion of human teeth by dentifrice abrasives: a test utilizing radioactive teeth. J Dent Res 1957; 37:1060-1068. This standard method compares the abrasivity of the dentifrices being evaluated, with that of a standard ADA slurry (RDA=100). To accomplish this, irradiated dentin samples are brushed with an aqueous slurry of the toothpaste in a standard brushing machine using fixed standard conditions such as the amount of toothpaste and dilution, number of brushing cycles, etc. The amount of radioactive material found in the dentifrice slurry after a specified number of brushing cycles is then measured and compared with the results obtained using a standard ADA toothpaste slurry (which is considered to have an RDA of 100). A similar test, the REA procedure, is sometimes performed using tooth enamel (Bruce R Schemehom et al., Abrasion, polishing, and stain removal characteristics of various commercial dentifrices. J Clin Dent 2011; 22 (1) 11-18).

The ADA (American Dental Association) has generally recommended that the abrasivity of a toothpaste be no more than that needed to prevent the excessive build-up of stains on teeth. Of course, the amount of stain built up by different individuals varies widely. Hence, the optimum toothpaste abrasivity is different for each individual and depends on many factors such as genetics, diet, whether the individual is a smoker or regularly drinks strong tea etc. Accordingly, it is up to the consumer to select the toothpaste they find most suitable. While there are no strict rules concerning abrasivity, the following provides some guidelines regarding ranges for toothpaste abrasivity.

A toothpaste with an RDA below about 50 is generally considered to have very low abrasivity. Such a dentifrice is particularly suitable for users whose teeth have a low tendency to stain. A toothpaste with an RDA abrasivity in the range of between about 50 and about 150 is generally considered to have a moderate abrasivity. Such a toothpaste would be satisfactory for most of the population with regard to stain prevention and potential damage to teeth. A toothpaste with an RDA abrasivity of above about 150 would generally be considered to exhibit a high abrasivity and would only be suitable for users with a high tendency to develop tooth staining, such as smokers or heavy tea drinkers. The FDA recommends a maximum upper limit on RDA of 200, while the ADA specifies an upper limit of 250. Accordingly, toothpastes with an RDA above 250 would generally be considered to have an excessive abrasivity and be potentially damaging to teeth. Dentifrice compositions of embodiments of the invention should preferably have an RDA of between 30 and 200, more preferably between 50 and 150.

Depending on the type of dentifrice formulation and the desired characteristics, dentifrices can contain from about 5% to about 98% concentration of an abrasive ingredient. For example, the abrasive content of a powdered dentifrice could range from about 50% to about 98% (w/w). A toothpaste may have an abrasive content between about 10% and 65%, and the abrasive content of a tooth-gel can range from about 5 to about 35%. For a tooth liquid (which has a viscosity intermediate between a toothpaste and a mouthwash), the concentration of abrasive might be from 5% to about 30% w/w.

Dentifrices that are used for professional cleaning in the dental office, generally have a higher acceptable abrasivity than dentifrices available for use at home. This is because the dentifrices for use at the dental office are designed for infrequent use to remove any stains which have built-up since the previous visit to the dentist. While it is generally undesirable for tooth mineral to be removed during a prophylactic cleaning, it is necessary to remove the pellicle layer with entrapped stain that has built up since the previous visit to the dentist.

There are widely varying types of abrasives that can be included in compositions of embodiments of the invention. The following is a non-exclusive list of abrasives that would be effective in these toothpaste compositions: alumina, hydrated alumina, silica, aluminosilicates, calcium aluminosilicate, hydrated silica, calcium carbonate, dicalcium phosphate dihydrate, anhydrous dicalcium phosphate, tricalcium phosphate, calcium pyrophosphate, heat treated calcium pyrophosphate, untreated calcium pyrophosphate, calcium hydroxyapatite, insoluble sodium metaphosphate, calcium polymetaphosphate, magnesium carbonate, magnesium orthophosphate, magnesium trisilicate, titanium dioxide, perlite, pumice, sodium bicarbonate, aluminum silicate and zirconium silicate. Preferred abrasives include hydrated silica (W. R. Grace Co.), known as Sylodent®, and Zeodent, and dicalcium phosphate dihydrate and calcium carbonate.

A wide choice and range of concentrations of abrasive can be used dentifrices of the invention. Excessive toothpaste abrasivity is of course of concern regarding the potential scratching of tooth surfaces or thinning of the enamel layer. There are many types of abrasives which can be used, but a satisfactory choice might be a mildly abrasive dental grade of hydrated silica. It can be noted that the abrasivity provided by any amount or form of the cellulose itself that is contained in embodiments of the invention, is expected to be low.

The term abrasives, as used herein, may or may not overlap in the particle size dimensions and other characteristics with the particles such as MCC that are described elsewhere herein. Abrasives are intended to remove stains from the surfaces of teeth. Such particles typically have hardness less than 3 on the Mohs Hardness Scale, because such hardness is sufficient to remove stain while not being so hard as to damage tooth enamel or dentin. Their hardness may be greater than 2 on the Mohs Hardness Scale. Such particles typically have dimensions in the range of about 15 to about 30 microns average diameter, or more generally 5 microns to 50 microns. Such particles may be spherical or not greatly elongated in shape (elongated by a factor of not more than 2), or may be irregular. In comparison with the particles such as MCC, the abrasive particles may be smaller than the particles such as MCC, and their shape may be closer to spherical (such as elongated by a factor of not more than 2) than are the shapes of the particles such as MCC. Examples of the composition of such abrasive particles include: amorphous silica such as that made by W. R. Grace and Company others (e.g. Zeodent 113, DeWolf Chemical, Warwick, RI); calcium carbonate (CaCO3); calcium phosphates and zeolites (which are microporous aluminosilicate minerals). A composition of embodiments of the invention can contain silica, typically amorphous hydrated silica having a hardness less than 3 on the Mohs hardness scale. This would be mostly for stain removal, while still being soft enough so as not to erode enamel or dentin. Such material is available from W. R. Grace and Co. as SYLODENT®. Among the many known forms of silica, silica used herein may be dental grade silica, which provides appropriate hardness and particle size range. Alternatively, the hardness could be harder.

It is desirable that the abrasive chosen should be compatible with the other ingredients in the dentifrice especially the source of fluoride ingredient. There are several abrasives that cannot be used when sodium fluoride or stannous fluoride are present because those abrasives would cause the precipitation and inactivation of the fluoride ions during storage. The following abrasives are compatible with sodium fluoride: silica, hydrated silica, heat treated calcium pyrophosphate, sodium metaphosphate, titanium dioxide, perlite and sodium bicarbonate. The following abrasives are compatible with stannous fluoride: silica, hydrated silica, heat treated dicalcium phosphate, sodium metaphosphate, titanium dioxide, perlite. In the event that one of these fluoride incompatible abrasives is desired for the composition, a stable fluoride-containing composition can usually generally be formulated with sodium mono-fluorophosphate.

The concentration of such abrasive particles can be in the ranges defined herein for the prototype formulation (irrespective of other ingredient concentrations in the prototype formulation).

Herein, it has been found that the presence and concentration of the abrasive particles has an effect on the rheology of the composition. It is believed that the various types of particles described herein (both abrasives and particles that are MCC or similar substances) are incorporated in and entangled in the network formed by the Minute Fibrils. This raises questions about the relative function of abrasive particles and the particles that are MCC or similar materials. It is possible that their roles in cleaning overlap and they both have effects on the rheology of the composition. This may allow for using mixtures of abrasive silica and MCC to tailor cleaning and to reduce erosion of enamel and dentin. The effect on rheology can be quantified, for example, by measurement of G' using a rheometer. Although abrasive silica has been used in experiments, it is believed that other similar solid particles such as calcium carbonate could similarly be used. It is even possible that particles of abrasive could entirely substitute for MCC. In the present work, it has been found experimentally that particles of substances such as abrasives can be entangled in network and this can have a profound effect on rheology and can even increase viscosity or G' by as much as factor of 10 or even more.

SuperAbsorbent Polymer

In embodiments of the invention, a composition can include a superabsorbent polymer (SAP). Superabsorbent polymers have the ability to absorb very large amounts of water compared to their dry mass, for example up to 1000 g of water per gram of polymer.

Information on SAP, and options for SAP, such as particulate SAP, can be found in patent application U.S. Ser. No. 16/461,536, filed May 16, 2019, for example at ¶¶0029-53. Superabsorbent polymers are reviewed in Mignon A et al: Superabsorbent polymers: A review on the characteristics and applications of synthetic, polysaccharide-based semi-synthetic and smart derivatives. European Polymer Journal 2019; 117:165-178. Superabsorbent polymers are also reviewed in: Superabsorbent Polymer Materials: A Review. Iranian Polymer Journal, June, 2008. Superabsorbent polymers may be either synthetic or naturally-occurring.

A common chemical category of SAP polymers is polyacrylate-acrylic acid polymers. For example, a useful synthetic Super Absorbent Polymer is typically a copolymerization of acrylic acid with sodium, potassium or ammonium salts, or surface cross-linked polyacrylic acid. A list of SAPs that can used without limitation is given in our SAP patent application US20200270551, U.S. Ser. No. 16/461,536. See also Superabsorbent Hydrogels That Are Robust and Highly Stretchable, by B. H. Cipriano et al, Macromolecules 2014, 47, 4445-4452.

However, any SAP chemistry that is safe for dental or oral use can be considered. Embodiments of the invention are not limited to polyacrylate-acrylic acid polymers or their derivatives.

Embodiments of the invention may include natural SAPs for example polysaccharide-based SAPs. In regard to naturally occurring SAP, an example of a natural superabsorbent absorbent polymer is soluble fibrous ingredient comprises psyllium polysaccharide. This polysaccharide is present in natural plantago ovarta, as well as in psyllium husks, seeds and leaves. This polysaccharide source, which is mostly composed of inulin, is a water-soluble fructan fiber with a beta-(2-1) glucoside linkage. This mucilaginous material expands in water and increases its viscosity. It helps to provide more structure and enhances plaque biofilm removal. Psyllium seems better able to retain moisture than synthetic SAPS without the need for cross-linking. Without being bound by this mechanism, we believe that its advantageous characteristics are probably associated with the ring structures in psyllium. Water molecules can fit into the ring structures and are held by hydrogen bonding by the hydroxyl groups on the ring. Other potentially suitable natural sources of soluble super absorbent mucilage, which expand in aqueous media, are beta-glucans from oats, oat bran, flaxseed, pectin and gums found in berries, seeds, citrus peel or other fruit sources. Water-absorbing polysaccharides may preferably be chosen so that they are not lubricating, as discussed elsewhere herein.

The particle size of the dry SAP particles can range from 2 to 63 microns or from 2 to 106 microns more preferably from about 5 μm to about 75 μm, or from 2 to 150 microns or larger, and can include particles up to 800 microns. The SAP particles may include small particle size versions such as carbopols or carbomers (about 2 to 7 μm), as well as larger particles such as those used in hygiene pads or diapers or similar applications (2 μm up to 800 μm). The particle sizes of SAP and NSAP may be chosen so that when the particles are in the swollen state the particles are no larger than about 200 μm. Other sizes are also possible.

Synthetic superabsorbent polymers may be made from polymeric water-soluble polymers that are surface cross linked to allow water to be absorbed through the lightly cross-linked matrix around the absorbing polymer. The polymer swells and forms a gel, thereby entrapping absorbed water. A useful property of such a polymer is that the particles of cross-linked protected polymer gel do not merge, stick together or lose their individual particulate identity. The result is the polymers have a high absorption capacity for water within its matrix structure, which can allow it to absorb up to 1000 times as much water as its dry weight. Non-crosslinked polymers are less desirable for this purpose because they are not protected from merging. The SAP can be surface crosslinked or non-surface crosslinked or highly bulk cross-linked or a mixture of the various forms.

The SAP polymer is envisioned to be in the form of discrete particles that tend to retain their identity as separate particles even after swelling. It is believed to be preferable to use SAP particles that are surface crosslinked or highly bulk cross-linked. Such particles avoid coalescing with each other after swelling. The SAP particles may be able, even when mixed or incorporated in the described composition, to preserve their integrity as discrete particles rather than joining other SAP particles to form a soft mass or expanded gel domains. The CRC (Centrifuge Retention Capacity) values may be from 50 to 500 g/g in pure water or from 15 to 50 g/g in saline solution. The CRC value for a cross-linked SAP is expected to be smaller than the CRC value for a non-cross-linked version of the same substance. The CRC value for a cross-linked SAP is indicative of the extent of cross-linking, with larger amounts of cross-linking being associated with smaller CRC value.

It is believed (although it is not wished to be limited to this explanation) that particles of SAP that are Surface Cross-linked or highly bulk cross-linked are more likely to retain their shape. It is believed, although it is not wished to be limited to this explanation, that desirably the SAP particles should not be ground or milled after Surface Cross-Linking, so that not more than 10% of the bulk polymerized SAP is exposed, or 10% of the total surface of the SAP, or 10% of the particles. The majority of the SAP particles may be provided having outer surfaces that are intact after the surface cross-linking. The surface crosslinked SAP also increases the elastic properties (G') of the composition, compared to compositions containing non-surface-cross-linked SAP. It is believed, although not confirmed, that SAPs may limit breakdown of the network and may retard the effect of dilution due to water or saliva as described elsewhere herein.

It is believed, although it is not wished to be limited to this explanation, that desirably the SAP particles should not be ground or milled after Surface Cross-Linking, so that not more than 10% of the bulk polymerized SAP is exposed, or 10% of the total surface of the SAP, or 10% of the particles. The majority of the SAP particles may be provided having outer surfaces that are intact after the surface cross-linking. It is possible that the particles of SAP, or the majority of them, may have irregular shapes. Other SAP particle shapes may be used including spherical or irregular without limitation. The density of bulk and surface cross-linking density can be tailored as desired without limitation. Further information is available in co-pending commonly assigned patent application U.S. Ser. No. 16/461,536.

A desirable criterion regarding Surface Cross-Linked (SCL) or otherwise desirable particulate SAP can be that if the particles are contacted against each other under load, the particles do not join or merge with each other. Particles of SAP that are surface cross-linked or highly bulk cross-linked may have CRC values that are smaller than the corresponding values for the same SAP material that is not surface cross-linked. Thus, the CRC value may be a representation of how much cross-linking has occurred. The outer surface of the SCL particles may desirably be thick enough to result in a CRC value in saline (0.9% concentration of NaCl, i.e., physiological saline solution) less than 32 g/g, preferably less than 28 g/g. The particles of SAP may be entangled in the fibrous network.

It is believed that when MFC and superabsorbent polymers together are combined and exposed to water, they expand and together play a role in helping to dislodge plaque biofilm and displace it from tooth surfaces. SAP particles may be incorporated within the fibrillated network, as evidenced by microscopic examination. The resulting entangled network forms a viscoelastic fluid which helps to transfer the forces of brushing to the biofilm on the tooth surface, hence effecting removal of the biofilm. In addition, the resulting rheology of the embodiment composition is such as to limit the formation of a depletion layer at tooth surface, which in turn ensures more direct contact between the dentifrice ingredients and biofilm. It is believed that the SAP enhances the elastic properties (G') of embodiment compositions, such that the elastic component forces the composition to make contact with biofilm under the action of normal force applied by the toothbrush. During translational motion during brushing, shear forces are created to remove adhering biofilms from teeth. However, we do not wish to be bound by any particular explanation.

Humectant or Water Retention Agent

Water activity also describes the chemical activity of the water in the toothpaste, as it relates to physical, chemical and microbiological characteristics of an aqueous solution. For example, because bacteria and fungi need moisture to survive, a low water activity will prevent bacterial and fungal growth in the toothpaste. Most bacteria do not grow when the water activity is less than about 0.8. Other organisms cannot grow if the water activity is less than 0.6. It should be noted that bacteria and other organisms can still be viable when the water activity is low even if they do not grow. Of course, growth and viability of organism is also affected by the presence of other ingredients in the formulation, such as preservatives. Replacement of water with humectants reduces the water activity and generally improves the smoothness and consistency of a toothpaste. Some humectants also generally improves the smoothness and consistency of a toothpaste. Humectant ingredients also are reported to reduce attachment of plaque biofilm to tooth surfaces.

The water activity (Wa) of a composition is the ratio between the vapor pressure of the composition itself, when in equilibrium with the surrounding air media, and the vapor pressure of pure water under identical conditions. Water activity is measured by determining the equilibrium vapor pressure above the toothpaste in an enclosed container at the chosen temperature. The water vapor pressure is then divided by the vapor pressure of pure water at the same temperature and Water activity is expressed as a number between 0 and 1. This is described in U.S. Pat. No. 7,135,163. Ideally, for toothpaste, the water activity should be less than about 60% although another useful target can be less than 70%. Preferably, the water activity of toothpaste embodiments should be less than 0.78, more preferably less than 0.75 and most preferably less than 0.70.

Preferable humectants include glycerin, 1,3 propylene glycol, 1,2 propylene glycol and sorbitol. Xylitol and erythritol are other useful humectants and may have some additional benefits perhaps by preventing plaque attachment or by favoring less cariogenic bacteria in the mouth. Compositions of the invention may include one or more humectants selected from the following: glycerin, sorbitol (available as sorbitol 70%), xylitol, erythritol, 1,3 propylene glycol, 1,2 propylene glycol, dipropylene glycol, ethylene glycol, polyethylene glycols with from about 5 to 12 repeating ethylene glycol units, and higher polypropylene glycols, and some other sugar alcohols.

In embodiments of the invention, in order to lower water activity down to 0.75 or lower, the humectant may be glycerol, propane diol or sorbitol at a concentration of 30%, 40% or even 50% of the composition, preferably in the range of 35% to 45%. It is possible to use a combination of these humectants, and the concentration can be the total of the concentrations of the individual humectants. It can be noted that xylitol and erythritol precipitate at concentrations above around 30%.

Inert fillers such as microcrystalline celluloses might have an effect of reducing water content and helping to control the water activity. Salts that can be added include mono, di- and trisodium orthophosphate, monoammonium, diammonium and triammonium phosphate and monopotassium, dipotassium and tripotassium phosphate salts. The pH range may preferably be 3.5 to 9.5.

Humectant-water mixtures may be used to make the compositions of embodiments of the invention, as described elsewhere herein.

Surfactants or Foaming Agent

In embodiments of the invention, the composition can include a surfactant or a mixture of surfactants.

The surfactant may help in the removal of plaque. A significant purpose of surfactants is to create some foam during brushing. Foaminess is a sensory attribute that users expect and prefer, because they associate it with effective cleaning. Accordingly, in embodiments, the composition can include a surfactant that can produce some foam upon being agitated, as long as the type and concentration of the surface does not negatively impact the desirable rheological or friction properties as described elsewhere herein.

Surfactants may also have benefits as emulsifiers, which can be used to disperse water-insoluble ingredients such as flavor oils into the composition. It is possible that in the absence of a surfactant, during storage, such water-insoluble oils might undesirably separate from the bulk aqueous phase.

Formulation embodiments of these compositions may include one or more surfactants in concentrations between about 0.1% and 2.0%, preferably between about 0.25% and 1.5%, and most preferably from about 0.4 and about 1.2%. Preferred ingredients in compositions of the invention are one or more surfactants which are present in a concentration not to exceed about 2.5% and preferably in a concentration between 0.2% and 1.5%. Higher concentrations can be irritating while concentrations that are too low will not create sufficient foam.

Suitable surfactants include almost any non-toxic, non-irritating surfactant. Commonly used surfactants that can be used in toothpastes or other oral rinses are sodium laureth sulfate and cocamidopropyl betaine. Other possible surfactants include for example sodium lauryl sulfate (SLS) or sodium dodecyl sulfate (SDS) which is commonly used in commercial toothpastes.

In general, a surfactant in an embodiment of the invention can be any type of surfactant, including for example, anionic, cationic, or amphoteric surfactants. Most preferred surfactants are either anionic or amphoteric surfactants and mixtures thereof. It is useful to specify the degree of foaminess and the type of foam so that the composition can remain effective in removing plaque biofilms and calcium deposits during application.

In regard to anionic surfactants, examples of suitable anionic surfactants are water-soluble salts of alkyl sulfates with between 8 and 18 carbons in the alkyl chain.

Preferable anionic surfactants for use in toothpaste of this invention include sodium lauryl sulfate (SLS), which is also known as sodium dodecyl sulfate (SDS). Another suitable anionic surfactant is sodium lauroyl sarcosinate. Another group of high foaming anionic surfactants is sodium salts of hydroxyalkyl sulfates, for example sodium 2-hydroxyteradecyl sulfate and sodium 2-hydroxydodecyl sulfates. These surfactants are known to avoid the "orange juice effect" experienced with many other anionic surfactants. The orange juice effect results in a seriously adverse flavor when orange juice is imbibed after toothbrushing was performed using surfactant-containing toothpaste. Among other useful anionic surfactants are sodium N-methyl taurate, and sodium salts of sulfonated monoglycerides. A most preferred alkyl sulfate is sodium lauryl sulfates. Another group of useful anionic surfactants include water salts of lauroyl, cocyl, myristoyl and palmityl and steroyl sarcosinates. Particularly preferred is sodium lauroyl sarcosinate.

Examples of suitable anionic surfactants are the water-soluble salts of alkyl sulfates with between 8 and 18 carbons in the alkyl chain. A most preferred alkyl sulfate is sodium lauryl sulfate. Another group of useful anionic surfactants include water-soluble salts of lauroyl, cocyl, myristoyl, palmityl and steroyl sarcosinates. Of these, sodium lauroyl sarcosinate is preferred. A combination of sodium lauryl sulfate and sodium lauroyl sarcosinate provides a synergistically higher amount of foam than when either is used alone. Another anionic surfactant which is suitable in these dentifrice embodiments is sodium methyl cocoyl taurate. Similarly, sodium lauryl sulfoacetate and sodium lauroyl isoethionate can be used. Sodium laureth carboxylate is a somewhat lower foaming but acceptable surfactant. Another group of high foaming anionic surfactants are sodium salts of hydroxyalkyl sulfates, for example sodium 2-hydroxyteradecyl sulfate and sodium 2-hydroxydodecyl sulfate. Among other useful anionic surfactants are sodium N-methyl taurate, the water-soluble salts of sulfonated fatty acid mono-glycerides having 8-18 carbons in the fatty acid chain are also effective, especially is sodium coconut monoglyceride sulfonate.

In regard to amphoteric surfactants, a preferred amphoteric surfactant is cocamidopropyl betaine. Examples of amphoteric surfactants which can be utilized in embodiments of these dentifrices include alkyl betaines such as lauryl, myristyl, palmityl and cetyl betaine. Also useful are the amidobetaines including cocamidopropyl betaine, cocamidoethyl betaine and lauramidopropyl betaine. Cocamidopropyl betaine is especially preferred when used alone or in combination with an anionic surfactant such as sodium lauryl sulfate. Amphoterics are often less irritating than other surfactants and sometimes even reduce the irritation potential of other ingredients. Amine oxide surfactants, either alone in combination with betaine surfactants, can be used to make the inventive compositions as they may impart some antimicrobial properties.

In regard to nonionic surfactants, a suitable group of nonionic surfactants includes those known as the poloxamers (block co-polymers of ethylene and propylene oxide), polysorbates and sucrose or glucose esters. Nonionic surfactants also are especially useful as emulsifiers, for example to disperse flavor oils and other water-insoluble ingredients into the dentifrice. However, nonionic surfactants tend not to deliver as high a foam as is achieved with anionic surfactants and amphoteric surfactants. Nonionic surfactants may be utilized in combination with anionic or amphoteric surfactants to stabilize the foam.

Cationic surfactants, especially those which have antimicrobial properties, are not necessarily desirable for compositions of these embodiments, because such surfactants tend to be significantly more irritating and cytotoxic to the oral mucosa than other surfactants. Therefore, if they are used, the concentrations may be limited to a small concentration, for example, generally less than 0.3%. A further concern with cationic antimicrobials is their potential to promote the development of antibiotic and antimicrobial resistant strains of bacteria as discussed previously concerning toothpaste antimicrobials. Cationic surfactants also have other undesirable properties, such as increasing tooth staining, and incompatibility with many other potentially useful ingredients such as anionic surfactants and anionic polymers (e.g., CMC). Cationic surfactants also form inactive salts with saccharin and, when used with high specific surface area abrasives, are adsorbed and thereby inactivated.

Where cationic surfactants can sometimes be used is to provide anti-microbial activity to the dentifrice. However, cationic surfactants are often incompatible with other ingredients in some formulation. For such reasons, cationic surfactants may be less preferred for cleaning teeth. However, for various reasons cationic surfactants might be included in suitable concentrations. For example, cationic surfactants are routinely used in "Scope mouth rinse" made by Procter & Gamble. Suitable cationic surfactants, which are also antimicrobial, include benzalkonium chloride, benzethonium chloride, methyl benzethonium chloride, cetyl pyridinium chloride and tretradecylpyridinium chloride.

A specific surfactant ingredient that can be used is LAE (Lauryl Alginate Ester) hydrochloride or other salts. LAE is a natural cationic surfactant and is a natural preservative, and it has good attributes for retarding biofilm formation. For example, we have found that a concentration of 0.1% to 1% of LAE, or 0.5% to 1%, in combination with other ingredients of the inventive tooth cleaner, can also produce foam and promote cleaning. LAE is a cationic surfactant and it breaks down to arginine (which is an amino acid) and lauryl acid (which is a fatty acid) both of which are common in food and are safe. LAE seems to lower the surface tension of its composition and may also have a propensity to absorb on the surface of teeth giving after-brushing more persistent effect that may delay or retard biofilm formation. LAE has good ability to form foam (which is desirable in toothpaste), and also is a preservative and has some antimicrobial effect. It is considered a cationic surfactant and can replace other surfactant options for the formulation. Because of its arginine moieties, LAE may protect against tooth sensitivity.

It should be noted that the presence of surfactants is not essential to the performance of embodiments of these compositions. However, we have found that the cleaning action is often improved by the presence of surfactants.

Foaming agents are a subset of surfactants, and constitute an important ingredient in toothpastes. Consumers perceive toothpastes as less effective at cleaning if the foam is insufficient. However, the concentration of foaming agent added to the toothpaste formulation should not be excessive. Excessive foaming agent adversely affects flavor and mouth feel. Furthermore, some consumers are sensitive to surfactants and suffer from mouth sores when too much foaming agent is present. A widely used foaming agent is sodium lauryl sulfate. It is possible that sodium lauryl sulfate is acceptable and less risky than choosing other possible surfactants. On the other hand, it might be possible to identify a more natural or naturally-derived surfactant, though this could take considerable effort. For example, it is possible that a concentration of from 0.5% to 0.8% of sodium lauryl sulfate would prove satisfactory.

Thickeners and Rheology Modifiers in General

In addition to inclusion of minute fibrils, fibrillated materials or network-forming ingredients, one of the mechanisms by which the inventive composition promotes dislodgement and removal of plaque biofilm, is by achieving an appropriate rheology of the composition as detailed elsewhere herein. In toothpastes in general, it is sometimes desirable to incorporate thickeners or rheology modifiers for aesthetic or performance reasons. An increase in viscosity or G' may be desirable to prevent sagging of the toothpaste ribbon and to help stand-up when applied to the toothbrush. Such also may help prevent syneresis and may give a smoother feel to the composition. Thickeners may also be used in toothpastes to help suspend undissolved ingredients such as abrasives. Additionally, as noted regarding the composition's plaque dislodging ingredients, increasing the dentifrice's viscosity and tailoring its rheological parameters can help the transfer of brushing forces to biofilm being removed. However, in embodiments of the invention, it is found that there are both advantages and disadvantages for thickeners and rheology modifiers. The disadvantage can be lessening the contact of the fibers and fibrils and various types of particles with the biofilm at the surface to be cleaned.

Inorganic Thickeners

One commonly used group of thickening agents are the inorganic thickeners frequently referred to as thickening silicas. These silicas are distinct from abrasive silicas, which are sometimes referred to as cleaning silicas. Both types of silicas are sometimes referred to as "hydrated silica" or occasionally even just as "silica." The primary differences between thickening and abrasive silicas are in their specific surface areas, absorptive capacities and abrasivities. Thus, thickening silicas have larger specific surface areas and higher liquid absorptive capacities but are essentially non-abrasive, whereas abrasive silicas have smaller surface areas and lower absorptive capacities but deliver much higher abrasivities. As a result, abrasive silicas may affect the viscosity and other rheological properties, not to the same degree as thickening silicas. If an inorganic thickener is used, preferred inorganic thickeners include hydrated silicas, amorphous silicas, pyrogenic silicas, colloidal silicas, fumed silicas, and silica gels used at concentrations between about 1% and 10%. When added to aqueous media, silicas thicken through hydration with moisture in the composition forming a hydrated silica structure throughout the dentifrice. In addition to increasing the toothpaste's viscosity, another use for thickening silicas is to improve the mouthfeel of the composition.

As examples of inorganic thickeners, embodiments of the invention may comprise from 0% to about 10% concentration of silicas, such as Zeodent 165. These silicas absorb water and form chemical hydrates with silica. These materials form links and thicken aqueous compositions. It is also possible to use inorganic thickeners such as laponite and other clays.

In toothpastes in general the concentration of such inorganic thickeners, if present, could be in the range of 0.5% to about 10%. However, in work relating to embodiments of the invention, it has been found that it is preferable that the concentration of inorganic thickeners be limited to no more than 0.5% to 4% of the composition.

Polymeric Thickeners

Polymeric thickeners, which are common in conventional toothpastes, can be used in embodiments of dentifrice formulations discussed herein. For example, organic polymers are useful in adjusting the viscosity of dentifrices and liquid compositions. Additionally, they can be helpful for smoothing the dentifrice and for preventing syneresis (separation). The term polymeric thickeners as used herein does not refer to the Minute Fibrils or fibers.

Polymeric thickeners may be long chain polymers having hydrophilic groups spaced along the polymer chains and usually having high molecular weights for example from 2,000 to about 6 million Daltons. The hydrophilic groups may be nonionic, anionic or cationic. Non-exclusive examples of useful thickening polymers include polysaccharide gums, such as cellulose derivatives, including sodium carboxymethyl cellulose, hydroxymethyl cellulose, hydroxyethyl cellulose, hydroxypropyl cellulose. Other polysaccharides include guar gum, xanthan gum, carrageenan gum, tragacanth gum, and alginate salts of sodium potassium or ammonia, an alkali metal or ammonium salt of a polyacrylic acid, sodium carboxymethyl cellulose, hydroxymethyl cellulose, hydroxyethyl cellulose and hydroxypropyl cellulose, other hydropolymers based on cellulose derivatives, an alkali metal alginate salt or an ammonium alginate salt. Other such organic thickeners include polyvinylpyrrolidone, polyethylene oxide, polyacrylamide and its derivatives, which are used in some conventional toothpastes at concentrations between about 0.5 to about 10%, such as to improve the formulation texture and aesthetics.

Fluoride Additive

Fluoridating agents represent another optional dentifrice ingredient, which may be present in embodiments of these dentifrices. Meta-analysis of multiple clinical studies has confirmed a dose-dependent performance of fluoride toothpastes in preventing caries (Walsh T et al., A Fluoride Toothpastes of Different Concentrations for Preventing Dental Caries. [Cochrane Database of Systematic Reviews 2019, Issue 3. Art. No.: CD007868. DOI: 10.1002/14651858.CD007868.pub3].

In the United States, the fluoride content of Over-The-Counter anti-caries toothpastes is regulated by the FDA. The FDA has published Monograph (Code of Federal Regulations; Title 21, Volume 5; Revised as of Apr. 1, 2019; 21CFR355), which provides the range of fluoride concentrations permissible in toothpastes, the maximum allowable amount of fluoride in a single container of toothpaste, the permissible types of fluoride for use in dentifrices, and rules concerning pre-testing of fluoride availability and performance versus clinically proven effective fluoride toothpaste standards. The regulations also cover minimum concentrations of active fluoride which must be present during the labeled shelf life of the toothpaste. The Monograph also lays out package label requirements. Other countries have similar regulations although the details may differ significantly.

Embodiments of compositions herein described can optionally include a fluoride compound that can deliver active fluoride ions to the teeth. Three sources of fluoride, i.e., sodium fluoride (NaF), stannous fluoride (SnF2) and sodium mono-fluorophosphate (Na2PO3F), are permitted in the USA under the FDA Monograph. In addition to caries prevention, these compounds can strengthen tooth enamel and reduce erosion of teeth by acidic foods and drinks.

The FDA mandates testing requirements for fluoride availability and performance compared to clinically proven standards available through the USP (United States Pharmacopeia). It should be noted that amine fluorides are not a permissible source of fluoride in the USA, but they are approved in many other countries. For such other countries, embodiments of these compositions can include amine fluoride toothpaste.

In an embodiment of the invention, the composition may include a fluoride compound that is suitable to deliver active fluoride ions to the teeth. Such fluoride compound may be or may include sodium fluoride (NaF) or stannous fluoride (SnF2) system or sodium monofluorophophate (Na2PO3F) or other acceptable sources of fluoride without limitation. Such compounds are widely used in toothpastes and other dentifrices to strengthen tooth enamel. It is believed that such compounds convert the calcium mineral apatite into some form of fluorapatite. It is further believed that the resulting tooth enamel is more resistant to bacteria-generated acid attacks. The effective bioavailable concentration of fluoride should be equivalent to that of current commercial toothpastes. Such fluoride compound may be or may include sodium fluoride (NaF) or stannous fluoride (SnF2) or sodium monofluorophaphate (Na2PO3F). Such compounds are widely used in toothpastes and other dentifrices to strengthen tooth enamel. It is believed that such compounds convert the calcium mineral apatite into fluorapatite. It is further believed that the resulting tooth enamel is more resistant to bacteria-generated acid attacks. The effective bioavailable concentration of fluoride may be chosen to be equivalent to current commercial toothpastes.

In one of the commercially available toothpastes, the concentration of sodium fluoride is 0.24% by weight. In Commercial Toothpaste R, the concentration of stannous fluoride is 0.454% (which corresponds to a 0.15% w/v concentration of active fluoride ion). In embodiments of the invention, a fluoride concentration similar to or possibly higher than these concentrations can be used.

It can be noted that the presence of active fluoride ions was not a consideration for applications such as the cleaning of endoscope channels (described in U.S. Ser. No. 10/266,793). Although a toothpaste could be made without fluoride, most current toothpastes include fluoride as recommended by the American Dental Association. It is preferred to include water-soluble compounds, which deliver free fluoride ions to the teeth. Dentifrices that deliver appropriate amounts of free fluoride ions have been proven to significantly reduce the incidence of caries in users.

When included in dentifrices, preferred fluoride compounds are sodium fluoride (NaF), stannous fluoride (SnF$_2$), or sodium mono-fluorophosphate (Na$_2$PO$_3$F). Such compounds are widely used in toothpastes and other dentifrices to prevent caries and strengthen tooth enamel. All three of these fluoride ingredients are approved by the FDA as proven Safe and Effective for use as an anti-caries agent in dentifrices. Less preferred but acceptable fluoride compounds for use in dentifrices of the invention are amine fluorides. While amine fluorides are reported to deliver more fluoride to tooth mineral than other fluoride compounds, amine fluorides are not are not approved for inclusion in dentifrices by the FDA in the USA.

There are several mechanisms by which fluoride prevents caries: (1) Fluoride ions promote remineralization of tooth enamel using calcium and phosphate ions from saliva; (2) Fluoride ions react with calcium hydroxyapatite in tooth enamel producing a less water-soluble calcium fluoro-apatite and thereby reduce enamel demineralization due to acids from cariogenic bacteria; (3) Fluoride has an inhibitory effect on the growth of oral bacteria, thereby decreasing acid release by cariogenic bacteria.

Each fluoride-releasing compound has different characteristics, which affect the choice of fluoride depending on the composition of the dentifrice. Sodium fluoride completely releases essentially all of its fluoride ions to the saliva during brushing for maximum effectiveness. However, fluoride can be precipitated and deactivated in the presence of divalent and some other ions or by some types of abrasives. Hence sodium fluoride cannot be used in compositions conducive to its deactivation.

The fluoride in sodium mono-fluorophosphate is not present in the form of free soluble fluoride ions. Hence, the fluoride in sodium mono-fluorophosphate is "protected®" from reaction with divalent and other incompatible ingredients. Therefore, sodium mono fluorophosphate is the fluoride source of choice for dentifrices containing fluoride-incompatible ingredients. Studies generally indicate that sodium mono-fluorophosphate is slightly less effective than sodium fluoride in preventing caries because it takes time for free fluoride ions to be released from sodium mono-fluorophosphate during brushing.

Stannous fluoride has some performance advantages over other fluoride sources. Firstly, stannous ions react with tooth enamel and strengthens it, making it more resistant to acid attack. Stannous fluoride is also an effective antimicrobial agent, which decreases plaque biofilm build-up on teeth and reduces gingivitis. Furthermore, stannous fluoride is effective in reducing supragingival gingivitis. Another benefit of stannous fluoride is its ability to block dentinal tubules, which lead to the nerves in teeth. As a result, stannous fluoride is effective in preventing tooth sensitivity. As a disadvantage, stannous fluoride is somewhat less stable than sodium fluoride in dentifrices. Hence stannous fluoride-containing dentifrices gradually lose some of their effectiveness on storage. Additionally, stannous ions cause stain build-up on teeth. Furthermore, stannous fluoride imparts an adverse flavor, which is difficult to cover.

Amine fluorides tend to deliver greater amounts of fluoride to the surface of teeth and hence should be more effective in preventing dental caries. Examples of amine fluorides include: Ammonium monofluorophosphate; Ammonium fluoride; Hexadecyl ammonium fluoride; 3-(N-hexadecyl-N-2-hydroxyethyl-ammonio)propylbis(2-hydroxyethyl) ammonium dihydrofluoride; Ammonium hexafluorosilicate. However as noted above, amine fluorides are not approved by the FDA in the USA but are used in some other countries.

Dentifrices of the invention in general contain between about 0.05% to about 1% by weight of active fluorine. Dentifrices for regular twice daily home use should contain between about 0.08% to about 0.25% soluble fluoride compound. Prophylaxis pastes, used in the dental office, should contain from about 0.2% to about 1% fluoride. It can be noted that fibers and other components might skew what amount of fluoride is biologically available. For the USA, the permitted contents for fluoride toothpaste are identified in Table 1C.

TABLE 1C

Summary of FDA Monograph regulations for fluoride in OTC Dentifrices

| Type of fluoride | Total ppm F | Fresh Soluble F ppm ion | Aged Soluble F ppm ion | % compound |
|---|---|---|---|---|
| Sodium fluoride - | 1100 | 850-1150 | >650 | 0.188 |
| Stannous fluoride - | 1100 | 850-1150 | >700* | 0.351 |
| Sodium MFP Either | 1100 | 850-1150 | >884 | 0.654-0.884 or |
| Or | 1500 | 1500 | >1275 | 1.153% NaMFP |

*>290 ppm when heat treated calcium pyrophosphate abrasive is used

Buffer Salts

In embodiments of the invention, buffer salts such as mono, di and trisodium orthophosphate, monoammonium, diammonium and triammonium phosphate, and monopotassium, dipotassium and tripotassium phosphate salts can be included. Phosphate salts are not generally suitable as buffers for stannous fluoride toothpastes. These salts can serve to maintain the pH of the composition close to a desired value. The desired pH range for toothpastes with these embodiments is from about 3.5 to about 9.5 depending on the various ingredients in the toothpaste. For example, stannous fluoride needs a toothpaste in the pH range between about 4 to about 5.5. Sodium fluoride and sodium monofluorophosphate can be used at higher pH values.

Adjuvants

In embodiments of the invention, the composition can include any one or more additional ingredients or adjuvants such as: a sweetener such as sucralose or sodium saccharin; flavoring; colorant; a preservative. It is also possible to include a pH adjuster, as known in the art.

Embodiments of the invention may include one or more sweeteners such sucralose or saccharin, sodium saccharin, sodium cyclamate, sucralose, steviolglycodes, aspartame, acesulfame, xylitol, neotame. A possible starting point could be to use a concentration of about 0.3% to 0.5% saccharin, optionally combined with up to 0.1% sucralose. Sodium saccharin is a sweetener, benzoic sulfimide (C7H5NO3S, having a Molecular weight of 183.18 g/mol). Compositions of embodiments of invention may include from about 0.1 to about 2.0% concentration of flavoring agents. Flavoring agents can include but are not limited to: peppermint oil, spearmint oil, mixtures of mint oils, oil of wintergreen, clove oil, lemon oil, orange oil, grapefruit oil, lime oil, licorice, methyl salicylate, cinnamon, methyl cinnamate, ethyl cinnamate, butyl cinnamate, ethyl butyrate, ethyl acetate, eugenol, eucalyptol, anethole, carvone, menthone, thymol, cineol, methyl salicylate, vanilla, vanillin, carvone, licorice, thymol, menthol.

Sweetening agents suitable for these dentifrice embodiments include saccharin, sodium saccharin, sucralose, neotame, acesulfame, thaumatin, glycyrrhizin. These substances are hydropolymers. In embodiments of the invention, the composition can include any one or more of sweeteners such as saccharin, adjuvants such as: a sweetener such as sucralose or sodium saccharin; flavoring; a preservative. It is also possible to include a pH adjuster, as known in the art.

Tartar Control and Chelating Agents

A significant portion of the population suffers from tartar (also known as calculus) build-up on their teeth. This is dependent on the calcium content of their saliva, and often increases due to misalignment of teeth, which causes calcium phosphate deposition on and between teeth. Compositions of embodiments of the invention can include a tartar control agent such as pyrophosphate, tripolyphosphate and hexametaphosphate salts, and zinc chloride, zinc citrate or other zinc salts. These complex phosphates are also useful in preventing stain build up in the tooth surface and for supporting claims of tooth whitening.

Embodiments of the invention may comprise tartar control agents including Maleic acid copolymer, beta-D-galactose, beta-D-N-acetyl glycosamine, lactose, L-rhamose, beta-D-fucose (U.S. Pat. Nos. 4,362,713, 5,362,480; 4,775,525). Embodiments of the invention may comprise 1-20% Sodium alginate (average Molecular Weight 222), which helps to remove plaque by chelating calcium. Embodiments of the invention may comprise anti-plaque polysaccharide (U.S. Pat. No. 4,855,128) in a concentration of from 0.0025% to 1%. Such polysaccharides may be selected from the group consisting of lactobionic acid, xanthan gum, guar gum, gum tragacanth, guar gum, polygalacturonic acid, as long as they do not degrade the frictional properties of the composition as described elsewhere herein.

Embodiments of the invention may comprise an orally safe chelating agent. A known chelating agent for general (non-dental) applications is EDTA (ethylenediaminetetraacetic acid). However, EDTA might not be a desirable ingredient for dental applications. As an alternative, compositions of embodiments of the invention may comprise sodium gluconate. Sodium gluconate is a known and safe chelating agent that may sequester calcium during brushing. Other orally-safe chelating agents could also be used. Also, sodium alginate (average Molecular Weight 222), which helps to remove plaque by chelating calcium, could be used.

Tooth sensitivity often develops in the teeth of people in their thirties or forties. It is caused by receding gums which exposes dentin which is normally below the gum line. Dentin contains tiny tubules, which allows changes in pressure to the nerves within the pulp. Nerve sensitivity can be controlled using potassium salts such as potassium nitrate. Newer technology provides for ingredients which are deposited on the exposed dentin thereby blocking tubules. Because this toothpaste described herein contains only small quantities of hard abrasives which might remove protective mineral layers on exposed dentin, or maybe no such abrasives at all, the use of a toothpaste formulation of embodiments of the invention might be especially desirable for people who suffer from tooth sensitivity. In embodiments of the invention, the composition may comprise a) potassium nitrate; b) arginine; c) LAE; d) other anti-sensitivity compounds. In embodiments of the invention, the use of cationic compounds in combination with SLS may be avoided, because SLS is anionic and will neutralize the cationic compounds. Arginine 8%, which can be included for sensitive teeth, is an agent to reduce sensitivity of teeth. It modifies the pH of the saliva so as to cause precipitation of calcium into tubules. This contributes to clogging the tubules that create the sensitivity. Also, for people who have sensitive teeth we can take a typical toothpaste and reduce silica and it lowers sensitivity for people who have sensitive dentin or teeth. Also, Sensodyne toothpaste contains a local anesthetic.

Essential Oils

Embodiments of the invention can comprise essential oils. An essential oil is a substance extracted from a plant, so any natural oil is an essential oil. Essential oils do not necessarily act as anti-microbials. However, the term "antimicrobial essential oils" is sometimes used in reference to the four natural oils used as antimicrobials in Listerine, which have antimicrobial properties. They are (along with the concentration used in Listerine mouthwash) 0.042% menthol, 0.06% methyl salicylate, 0.064% thymol, and 0.092% eucalyptol. The percentages shown are the amounts used as the antimicrobial system in Listerine mouthwash. Still other ingredients that are essential oils or have antimicrobial properties include the following: Propolis; Aloe vera; Coconut oil; Cloves powder; Bloodroot; Limonene.

Essential oils may be included in embodiments of the invention that are toothpastes, mouth washes, chewing gums, or in general any other dosage form.

Antimicrobials or Antibiotics

Embodiments of the invention can comprise any of various antimicrobials or antibiotics. Examples of such substances include: a) cationic surfactants such benzalkonium chloride, benzethonium chloride, methyl benzethonium chloride, cetyl pyridinium chloride and tretradecylpyridinium chloride; b) quaternary amines; c) CHG (chlorhexidine gluconate) or CHX (chlorhexidine digluconate) or chlorhexidine acetate; d) cetylpyridinium chloride, benzethonium chloride and benzalkonium chloride; e) PHMB (polyhexamethylene biguanide); f) essential oils; g) LAE and derivatives; h) others. Stannous fluoride has antimicrobial properties. The ingredient triclosan, although not allowed in the US, has antimicrobial properties. For example, compositions of embodiments of the invention can be made specifically to treat thrush, yeast infections and fungal infections. Such embodiments may be made as specialty products so as to be dispensed for particular patients.

Preservative

Embodiments of the invention may include a preservative. It is possible that a preservative will not be needed in this formulation. Especially, if the water activity of the toothpaste is reduced to 60% or less, bacterial and fungal growth would likely be prevented even without the use of a preservative. There are many preservatives that could be used if desired, usually coupled with a buffer to adjust the pH to a mildly acidic range of about 5 to 5.5.

Humectant-Rich Compositions, and Categories of Compositions According to Amount of Humectant In some embodiments of the invention, the composition may comprise as large a concentration as possible of humectant and as small a concentration as possible of water. Such composition may be referred to as a nearly non-aqueous formulation. In addition to providing a suitable water activity of the composition, such situation may also have a benefit in regard to enhancing the entanglement of the Minute Fibrils. Such situation also may have a benefit in regard to the Superabsorbent Polymer, if such is included in the composition.

In regard to the amount of water that is contained in the composition, there may be some amount of water that is present unavoidably for reasons related to manufacturing. One reason for this is the fact that MFC is supplied commercially not in a dry condition, but rather as water-based paste. For example, MFC supplied by Borregaard is supplied in the form of a paste that contains 10% MFC, 90% water. MFC that is supplied by Weidmann is supplied in the form of a paste that is 30% MFC, 70% water. Reasons for this are discussed in U.S. Pat. No. 4,374,702 to Turbak and U.S. Pat. No. 4,481,077 to Herrick. Turbak describes that a basic process for preparing MFC can involve pumping a suspension of cellulose fibers through a high pressure jet creating shearing action and impinging or impacting. It is further described in Herrick that it is beneficial if the fibrillated material is never fully dried, because fibrillated material that is dried and then resuspended in water does not perform exactly as it did before the drying and resuspension. Further, it is disclosed in Herrick that if a liquid present around the fibrils includes a compound capable of substantially inhibiting hydrogen bonding of the fibrils. Water is not such a compound, but that category includes many organic liquids. In particular, included in that category are liquids that are of interest as humectants. Herrick indicates that it is further possible to evaporate water from liquid-MFC suspension after the other liquid has been introduced, such as by vacuum evaporation.

A further source of water is the possible use of sorbitol as a humectant or as one of a combination of humectants. Sorbitol is a solid at room temperature but is highly soluble in water. It is usually supplied in the form of an aqueous solution containing 70% sorbitol and 30% water. However, various other humectants can be used instead of sorbitol, and so sorbitol humectant does not have to be a source of water in the composition. In addition to sorbitol, it is possible that there could be some other ingredients that might be introduced to the composition as aqueous solutions, such as surfactants, flavors, etc.

In regard to numerical values of concentrations, it is possible that a composition of an embodiment of the invention could contain an MFC concentration of approximately 2%, referring to the fibrillated MFC material itself. If the MFC is added to the composition in the form of a paste that contains one-tenth MFC and nine-tenths water, then the composition would contain, in addition to the 2% MFC, a water concentration of 18%. This is how concentrations of ingredients in the compositions are reported herein. If the composition further contains 35% glycerin, as is the case for some embodiments, then the composition would be a majority-non-aqueous composition.

In addition to the majority-non-aqueous composition just described, other alternative compositions of embodiments of the invention could have a carrier liquid that is either entirely water or mostly water. Such embodiments have been described in patent application U.S. Ser. No. 17/062,424 and PCT/US2020/054149. Although they may have high water activity, they may be made resistant to microbial growth by including preservatives.

In still other embodiments, compositions could contain These are based mixtures of water and humectants; sometimes there is a larger concentration of humectants than of water. This class of formulation can be made to exhibit low water activity between 0.7 and 0.75 and in this context embodiments of the invention are equivalent to commercial and prior art toothpaste formulations.

It is found experimentally that even with the presence of humectants (e.g., propylene glycol, glycerol or sorbitol or their mixtures, at a total humectant concentration as large as 45%) in the toothpastes of an embodiment of the invention, the compositions were remarkably effective in removing highly adhering biofilms.

Figure 1A:
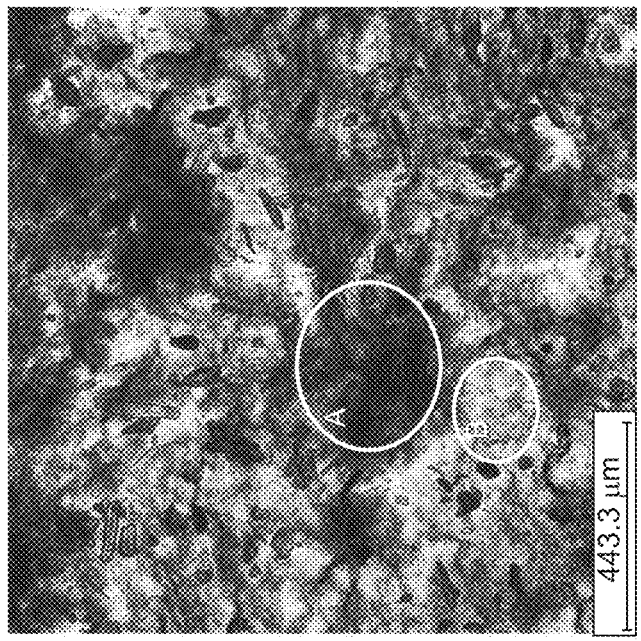
FIG. 1A is a micrograph showing a composition similar to an embodiment of the invention, in which microfibrillated material is dispersed in water, showing the existence of flocs and the existence of voids occupied by water.

Referring now to FIGS. 1A and 1B, there are shown micrographs Microfibrillated Cellulose in two different carrier liquids. FIG. 1A shows MFC in water as a carrier liquid, and it can be seen of that there is an intense aggregation of fibrils (i.e., flocs) with voids in between those aggregates. This would be typical of the low-humectant compositions disclosed in U.S. Ser. No. 17/062,424 and PCT patent application PCT/US2020/054149. In FIG. 1A, 35% of the area (with a likely standard deviation of about 5%) is occupied by large (>>10 microns in diameter) microstructural voids that contain little or no MFC. The other 65% of the area is occupied by MFC. In other words, about a third of the material microstructure is occupied by MFC-depleted large voids. These numbers could be influenced somewhat by the overall concentration of MFC in the composition. In FIG. 1B, the higher concentration of humectant (a concentration of 30-35-40% humectant) causes the fibers MFC to have a different microstructure because it makes the MFC more dispersed more highly dispersed and more uniformly dispersed and it is apparent that voids do not occur as they did in FIG. 1A. In FIG. 1B, with high concentration of humectant (35% glycerol), the fibrils extend all over and voids are essentially absent. There is no intense aggregation as was seen in FIG. 1A for the mostly-water case. A floc is a fibrillated entity or a plurality of fibrillated entities entangled with each other. A floc can be measured by laser diffraction at a very dilute condition. In many situations, an individual floc may not be particularly visible, but they can be seen once the composition is sufficiently diluted. FIG. 1A shows a microstructure comprising highly aggregated MFC flocs (A) and voids (Light shaded area B). FIG. 1B shows a uniformly dispersed MFC within the microstructure without visible voids.

Figure 1C:
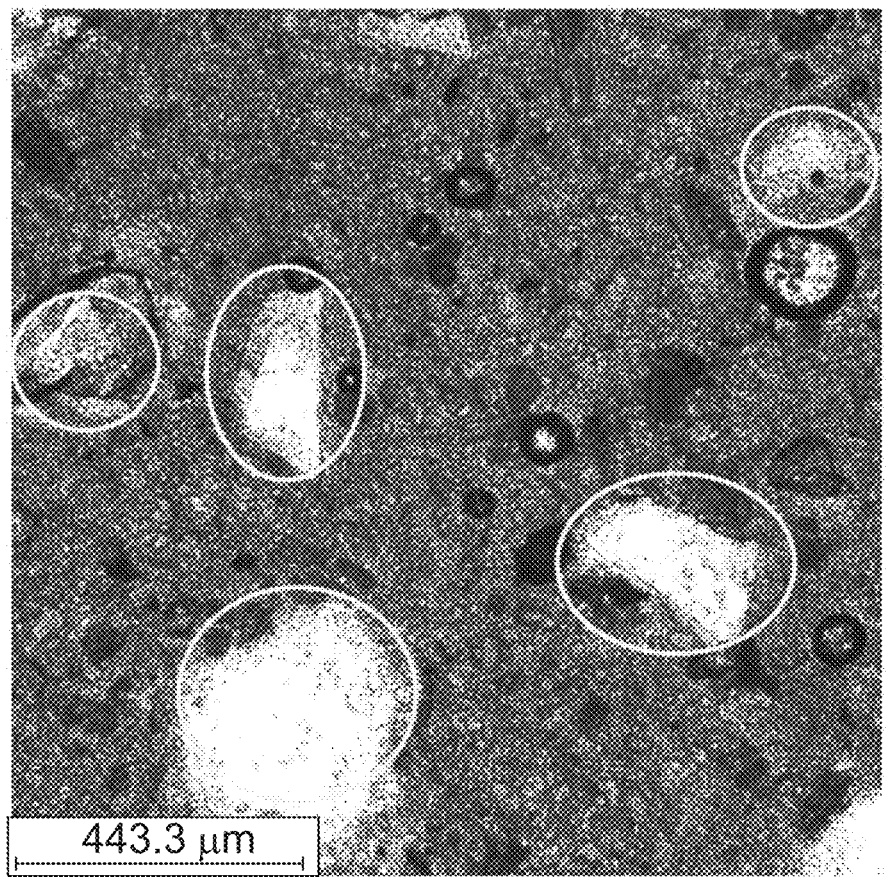
FIG. 1C is a micrograph showing particles of surface crosslinked SAP, dispersed in a composition of an embodiment of the invention.

Some compositions of embodiments of the invention comprise both MFC and high humectant concentration, thereby producing a unique and beneficial microstructure. This is shown in FIG. 1C. The embodiment composition is made with surface crosslinked SAP. SAP particles appear as light shaded irregularly shaped objects (circled by yellow circles). This is an example of a "thirsty" composition, having no voids, ready to absorb water.

Figures 1D, 1E:
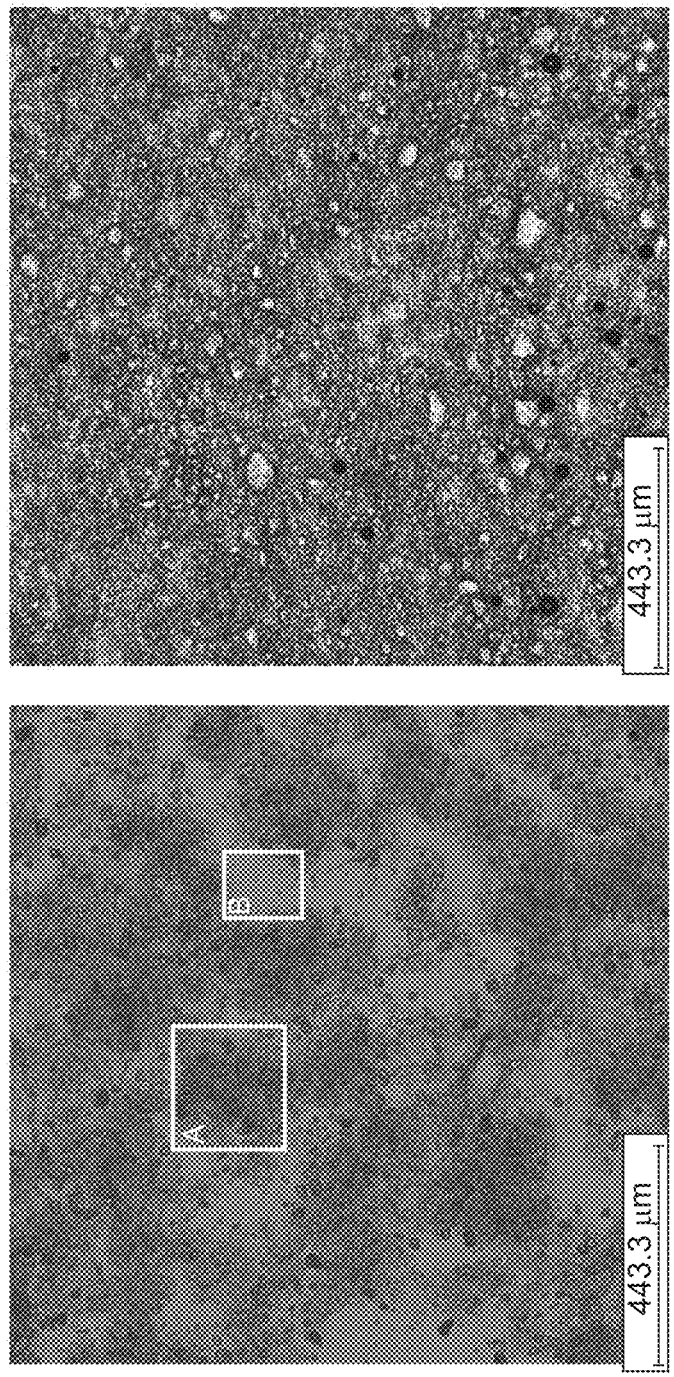
FIG. 1D is a micrograph showing a composition of an embodiment of the invention, in which particles of an abrasive are incorporated within the fibrillated network, and are generally absent in places were the network is absent.
FIG. 1E is a micrograph showing a prior art commercial abrasive-containing toothpaste, showing that the particles of abrasive are distributed generally throughout the composition.
Figure 1F:
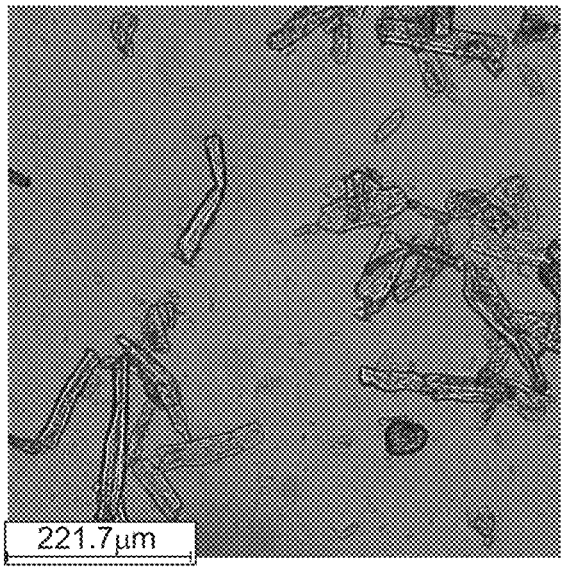
FIG. 1F is a micrograph showing particles of MCC (PH200) alone.
Figure 1G:
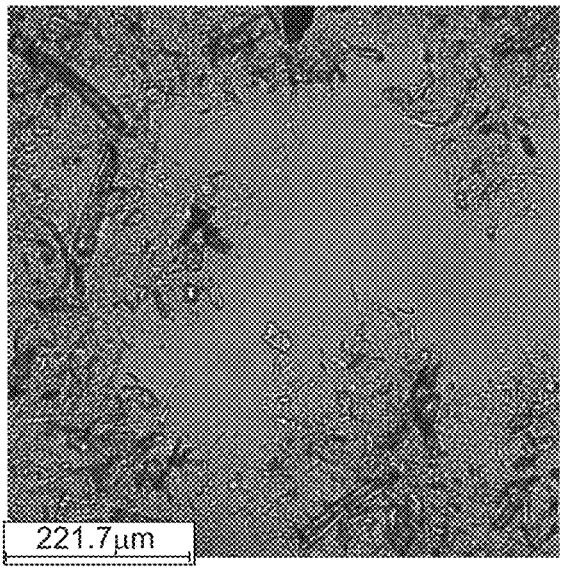
FIG. 1G is a micrograph showing particles of MCC (PH200) in the presence of MFC.
Figure 1H:
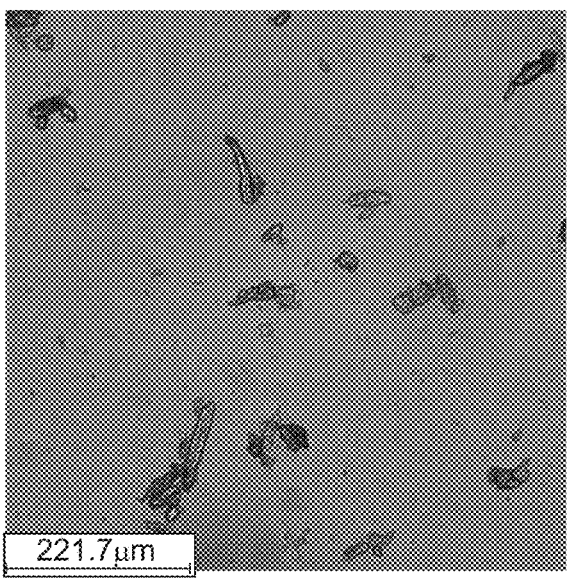
FIG. 1H is a micrograph showing particles of SMCC (SMCC50) alone.
Figure 1I:
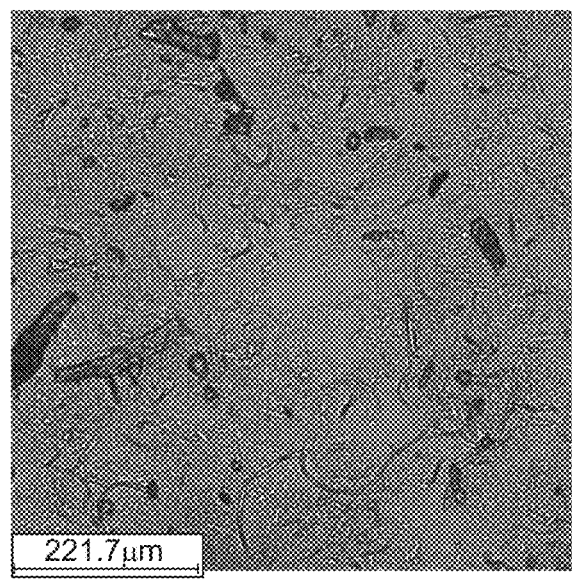
FIG. 1I is a micrograph showing particles of SMCC (SMCC50) in the presence of MFC.
Figure 9:
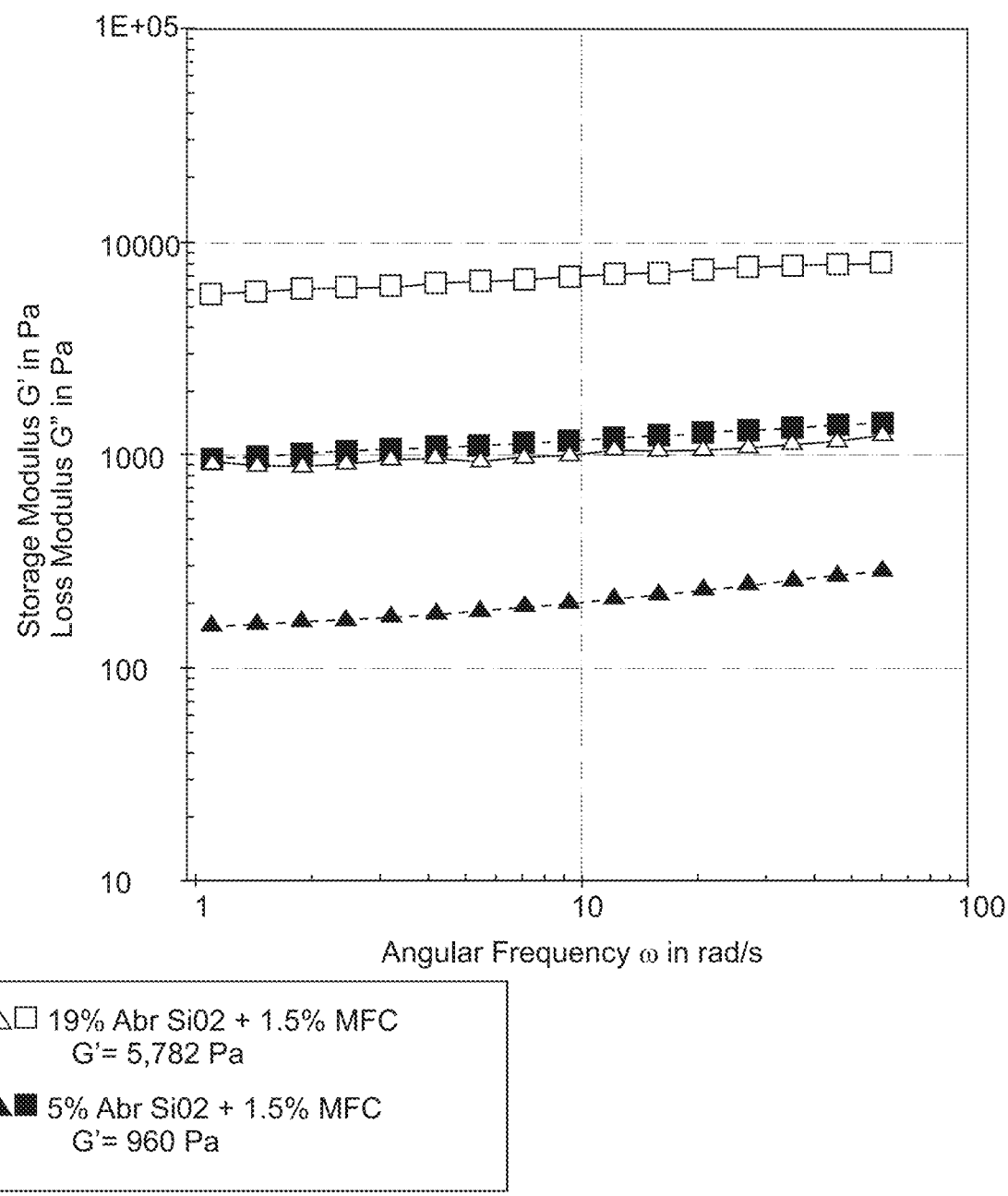
FIG. 9 shows the linear viscoelastic response of a composition made with 1.5% MFC in water with 5% and 19% abrasive silica (Zeodent 113).

It is believed that in embodiments of the invention, the abrasive silica particles become wrapped-up by the MFC fibers/fibrils thereby strengthening the mechanical properties of the network and possibly contributing an improvement towards stain removal as compared to the same concentration and type of abrasive silica dispersed in commercial toothpastes that lack the network. In FIG. 1D we show the evidence of abrasive silica trapped within MFC, with the carrier liquid being water. In FIG. 9 we report the resulting increase in viscosity (viscous modulus) and elasticity (storage modulus) when using a 19% concentration of abrasive silica (Zeodent 113) as compared to a 5% concentration of abrasive silica (Zeodent 113) in a solution of water containing 1.5% MFC. FIG. 1D shows abrasive silica particles incorporated within the fibrillated entity (A), and void (B) does not contain loose abrasive particles. FIG. 9 shows linear viscoelastic response of a composition made with 1.5% MFC in water with 5% and 19% abrasive silica (Zeodent 113).

In an embodiment we unexpectedly discovered that the abrasive hydrated silica particles become wrapped-up and incorporated by the fibers/fibrils of the microfibrillated network structure. FIG. 1D is a microscopic image that shows abrasive silica trapped within the fibrillated structure with no loose particles observed in the voids between the fibers and fibrils, even when the composition is diluted down to 50% of tis original concentration with water. This new microstructure is different from prior art commercial toothpaste (FIG. 1E), in which abrasive silica is loosely dispersed in the polymeric matrix. In FIGS. 1D, 1E, abrasive particles are the darkest particles. Light gray regions in FIG. 1D indicate liquid regions which are void. Also in FIG. 1D, it is possible to see fibrous with abrasive particles entrapped incorporated in fibrillated structure. The dark abrasive particles do not tend to be in the void (liquid) regions. In FIG. 1E (right), commercial toothpaste has an appearance resembling gravel. FIG. 1E shows commercial toothpaste with abrasive particles loosely distributed everywhere within the material.

Embodiment Compositions Having SAPs—Thirsty Compositions

In embodiment compositions that include particles of a SuperAbsorbent as described elsewhere herein, it is believed that it may be desirable to provide SuperAbsorbent Polymer in combination with a carrier fluid that may contain some water but has a high concentration of liquid humectant. It can be expected that in such a situation, in the toothpaste as delivered at the start of toothbrushing, the particles of SAP have not absorbed the equilibrium amount of water that they are capable of absorbing. Thus, they remain capable of absorbing additional water during the process of tooth brushing. In particular, this means that the SAP particles can absorb some saliva water produced during tooth brushing. It is believed that when saliva or water is absorbed by the SAP particles in this manner, that saliva or water is unavailable to cause the type of dilution that could cause the network of embodiments of the invention to become less effective in removing biofilm. In such a situation, the non-SAP components of the toothpaste can be expected to behave as though they were less diluted than one might expect from overall parameters. Therefore, behavior such as dilution-induced weakening of the network may be less severe than one would otherwise expect, and performance of the toothpaste for removal of dental biofilm may be improved. Persons skilled in the art may vary the type of SAP and humectant and their ratio to arrive at optimal performance with respect to removing plaque, stain or other residues. This embodiment is not meant to be limited to particular compositions. For example, it is applicable even to compositions that might not include minute fibrils or fibrillated materials. The goal of the embodiment is providing a new strategy to minimize the effect of saliva-induced dilution in toothpaste composition, broadly.

Embodiments of the composition can be made by considering the SAP CRC values and the water holding capacity (WHC) of the minute fibrils. The amount of water used in the composition can be less than the sum of CRC and WHC, meaning that the water used in the composition will be less that the amount required to obtain equilibrium swelling or hydration. These requirements can be satisfied by using humectant-water carrier liquid to make the composition. According to embodiments, this "thirsty" composition would have the propensity to remove water from mouth during the duration of brushing, and this would prolong the time during which the network maintains its favorable rheology and structure. The rate of removing water during brushing can be adjusted by selecting the type of SAP, its CRC value, its concentration, its rate of water absorption and the type and level humectant in the carrier fluid. It is believed that some of water removal may be arising from the humectant and minute fibril components of the composition. Persons skilled in the art may manipulate compositions to make such thirsty compositions according to the teaching of embodiments. The goal of making such composition is the reduction of the effect of saliva-induced dilution during brushing and maintaining the integrity of toothpaste structure so that optimal biofilm removal can be obtained. The invention is not intended to be limited to SAP, humectant, minute fibrils or other elements of composition.

In embodiments of the invention, the Minute Fibrils themselves also have a substantial water holding capability. In embodiments of the invention, it is possible to achieve water retention in the Minute Fibrils.

In some embodiments of the invention, the carrier liquid may comprise water and a concentration of one or more humectants. The total concentration of humectant(s) in the composition may be 20%, 30%, 40% or even 50% of the composition. The total concentration of humectant(s) in the composition may be larger than the concentration of water in the composition. At the same time, in embodiments of the invention, the composition also comprises particles of SuperAbsorbent Polymer. In addition to whatever effect the particles of SAP might directly contribute to cleaning, the ability of the SAP to absorb water may discourage syneresis and also may help to counteract the effect of dilution of the composition by saliva or water during use. Such dilution, if it occurs, might lessen the ability of the network to effectively cause cleaning action, because in a dilute situation the fibers/fibrils might become more distant from and separated from each other. Therefore, if water that might cause dilution of the network is captured by the particles of SAP, then that water would no longer be available to dilute or harm the network because the water would be sequestered inside the particles of SAP and would be unavailable to contribute to the loosening of the network. As a result, the composition would effectively contain less free water than might be expected based on overall proportions of the composition (including possible water/saliva added during brushing). In regard to the humectant that is present in the composition, presumably, the humectant would not be absorbed by the SAP, but rather would remain as liquid among the fibers/fibrils and other non-liquid components of the composition.

It is possible to quantify this criterion regarding the ability of the SAP to sequester water. A parameter that is descriptive of SuperAbsorbent Polymer is the Centrifuge Retention Capacity, which is the amount of pure water that can be held by the SAP per unit mas of the dry SAP. While some SAP can have a CRC value of several hundred g/g, it is believed that the form of surface cross-linked SAP or highly bulk cross-linked SAP that is desirable for embodiments of the invention can have a CRC value of 10-30 g/g. So, as an example calculation, if a composition contains a 50% concentration of water and 2% concentration of SAP, and if SAP has a CRC value of 25, then that concentration of SAP could absorb all of the water that is present in the composition. If a concentration of SAP is still larger than the amount just described, then even if the SAP were to absorb all of the water that is present in the composition, the SAP still would have additional capacity to absorb more water such as water/saliva introduced during brushing. This criterion can be expressed as:

$$CRC*[\text{concentration of SAP}] > [\text{concentration of water}]$$

Accordingly, in embodiments of the invention, the concentration of the SAP, multiplied by the CRC value of the SAP, may be greater than the concentration of water in the composition. As a further example, in embodiments of the invention, the concentration of the SAP, multiplied by the CRC value of the SAP, may be two, or more, times the concentration of water in the composition.

A further consideration is that the MFC fibers themselves have some ability to absorb water. In regard to this, the ability of fibrillated material itself to absorb water may act in somewhat the same way as the ability of SAP particles to absorb water. The parameter describing this is the Water Holding Capacity, WHC, also expressed in grams of water per gram of the material in question, namely MFC. Adding additional detail to the previous equation, this effect can be described as:

CRC*[concentration of SAP]+WHC*[concentration of MFC]>[concentration of water]

As a further example, in embodiments of the invention, the left side of the equation can be not just slightly greater than the right side, but could be a factor of two or more times the right side. It is believed, although it is not wished to be limited to this explanation, that during toothbrushing, when this water sequestration occurs, the network lasts longer and is more effective at removing plaque biofilm and stain than would otherwise be the case. It is believed that the SAP does not absorb humectant, and it is believed that the MFC fibrils do not absorb humectant either. It is believed that they only absorb water.

In an embodiment of the invention, the liquid content of the composition may be approximately 50% water and 50% humectant. In an embodiment of the invention, due to the remaining water-absorbing capacity of the SAP (and possibly the fibrillated material), the composition may be able to absorb an additional volume of pure water that is equal to the volume of the composition itself, or may be equal to half such volume.

Sequence of Manufacturing Steps, Especially for Humectant-Rich Compositions

An embodiment of the invention can also include a method of manufacturing some of the described compositions such as the "thirsty SAP" embodiment. Compositions of an embodiment of the invention may be made according to the following steps:

(A.) Solid ingredients of the composition such as MCC or similar solid particles and particles of SAP and possibly some of the abrasive silica and titanium dioxide are first suspended in pure humectant or in a humectant-water mixture, and then are homogenized to disaggregate them and to create a homogeneous uniform dispersion.

(B) Then, a portion or all of the fibrillated materials of the composition is added to the just-created dispersion in a sufficient amount/concentration so that the fibrillated material can form a protective adsorbed layer on the surface of the SAP particles. This adsorbed layer will stabilize them and prevent them from collapsing/coalescing with each other inside the composition.

(C) After mixing the solid particles and SAP in with the humectant or in the humectant-water mixture, the resulting composition is then homogenized to form a network where the solid particles and the coated-SAP particles become fully incorporated within the fibrillated network. The resulting composition becomes thick in consistency, has viscoelastic properties and possesses a yield stress as described elsewhere herein.

(D) After the fibrillated materials, solid particles and SAP are incorporated uniformly in humectant or the humectant-water mixture as described above, other solid ingredients including: additional fibrillated materials, remaining abrasive silica, remaining titanium dioxide and other ingredients as described elsewhere herein can be added and mixed with the above formed material under sufficient shear possibly with other type of mixing equipment and for a sufficient period of time to ensure the production of a uniform composition. Afterwards, the surfactant, flavors, sweeteners and preservatives are added to the above mixture and are then mixed to prepare the final toothpaste composition.

Dilution of Toothpaste

It is desirable that viscoelastic properties should remain in the effective range for removing biofilm (having a yield stress more than 10 Pa and having an elastic modulus or storage modulus greater than 1000 Pa) preferably for the duration of brushing or at least for more than 30 seconds and more preferably for more than 1 minute and most favorably for 2 minutes. It is desirable that these properties be maintained even with dilution to 50% of the original concentration of the composition. It is even more desirable if these properties can be maintained upon dilution to 33% or 25% of original concentration of the composition. Maintaining the viscoelastic properties of embodiment compositions at effective levels to remove biofilm plaque during brushing needs to be considered depending on the velocity and shear rates generated by the type of brush used. For example, conditions for effective biofilm removal may vary to some extent on whether manual, mechanical or sonic brushed are used to perform toothbrushing, as detailed in patent application U.S. Ser. No. 17/062,424 and PCT patent application PCT/US2020/054149 both filed Oct. 2, 2020.

Applicators and Dosage Forms

Although dentifrices such as toothpaste are prominent embodiments of the invention, dentifrices are not the only vehicle which can be used to physically remove plaque-biofilm from teeth using these embodiments. For example, effective plaque removal can be obtained using, for example, an oral device, such as a Water Flosser (Waterpik®, Fort Collins, Colorado), which forcefully delivers a stream of liquid composition onto and between teeth. Mechanical action can also be delivered by chewing a gum with compositional embodiments to dislodge and remove biofilm. Mechanical forces can also be supplied simply by thoroughly rinsing the mouth with a suitable mouthwash. Hence, while many of the embodiments discussed apply to compositions like dentifrices, it is envisioned that inventive compositions of different dosage forms, such as a mouthwash, a pre-rinse or a solid composition, such as a chewing gum, can be employed as embodiments as herein described.

One useful application of these embodiments is a dentifrice in the form of a toothpaste, tooth-gel, dental-cream, tooth-liquid or tooth powder which maximize the ability of the toothbrush or other suitable applicator to physically remove plaque-biofilm from teeth during brushing. Included in dentifrice embodiments are a prophylaxis paste, a prophylaxis gel, a prophylaxis powder for in-office stain removal and polishing of teeth by a dental professional. Another dentifrice embodiment is a professionally prescribed or applied high fluoride oral gel for patients at high risk of dental caries or who exhibit signs of early carious lesions such as white spots.

An oral composition of these embodiments can be supplied in almost any form such as a liquid, a spray, a semisolid, a paste, a gel, or a cream, which has a pre-formed 3D, entangled, viscoelastic structure in a liquid medium, or it can be in the form of a dry solid, a dry powder, a gum or an anhydrous paste or gel, which forms such a 3D, entangled, viscoelastic structures when mixed with water or when mixed with saliva during use. By dry, we mean that the dry solid or dry powders are not wet with significant concentrations of unabsorbed liquid components, such as liquid water, liquid humectant, or liquid surfactants that would make the compositions seem moist, i.e., the compositions are dry to the touch.

It has surprisingly been found that certain combinations of natural or synthetic polymers can be formulated into effective plaque-biofilm dislodging and removing compositions that are much more effective in physically displacing plaque-biofilm from on and between teeth than currently marketed conventional oral care compositions. For example, twice daily brushing with a dentifrice incorporating these embodiments physically removes significantly more plaque-biofilm from the dentition, than a conventional toothpaste. Thoroughly rinsing the mouth with a mouthwash embodiment, is more effective in displacing plaque biofilm from the teeth than rinsing with a conventional mouthwash. A special pre-brushing mouth rinse can deliver plaque-biofilm dislodging embodiments prior to regular brushing. Subsequent brushing will supply the forces needed to promote plaque-biofilm removal to better remove plaque biofilm. An advantage of such a pre-rinse is that users can get the benefits of the plaque removing components, while using a toothpaste composition of their own choice. Chewing gum embodiments can provide a way for health-conscious individuals to dislodge plaque and rid biofilm from their teeth after meals or at other times between regular oral-hygiene procedures when brushing is not possible. Plaque-biofilm removing embodiments not only include personal care compositions, but also compositions used or prescribed by dental professionals, such as prophylaxis pastes, fluoride treatment compositions and tooth preparations used to more effectively clean tooth surfaces prior to fillings, extractions or root canal surgery. Such compositions can be formulated with or without abrasives, which might otherwise damage enamel or exposed dentin. Indeed, it is also envisioned that a careful subgingival cleaning of the teeth with a periodontal treatment embodiment by a dental professional can effectively remove pathogens from periodontal pockets and provide the basis for a highly effective non-surgical treatment for periodontitis.

Modes of Action

While not wishing to be bound by any specific modes of action, we propose a combination of several mechanisms to account for the highly effective displacement of plaque-biofilm from the dentition by the ingredients in the dentifrice. We believe that the polymeric components contribute to the composition's ability to remove plaque biofilm in several ways. During brushing, the fibrils from the micro-fibrillated polymeric component play a direct role in penetrating the narrow spaces, such as between closely spaced adjacent teeth, within fissures in teeth, and also along the upper and lower crevices formed at the gingival margins, i.e., where the upper and lower teeth emerge from the gums. The fibrils and micro-fibrils reach into, entrap, and extricate plaque, from these aforementioned areas, which would normally be inaccessible. Also, when added to an aqueous medium, both the micro-fibrillated component and super absorbent polymers absorb water and swell. The micro-fibrillated components, together with the organic polymeric thickener, create a viscoelastic fluid enveloping the water-insoluble, entangled 3D fibrillated network. During toothbrushing, the viscoelastic dentifrice fluid transfers the applied brushing forces to the biofilm and displaces it from tooth surface. Due to the characteristics of the viscoelastic dentifrice, the formation of a depletion layer, which would otherwise inhibit biofilm removal is minimized. Contributions to biofilm removal efficacy are also made by the microcrystalline cellulose, abrasive particles (e.g., silica), the silicified microcrystalline cellulose, the nanocrystalline cellulose and/or the powdered cellulose ingredients, which use mild frictional forces to ensure superior plaque removal from tooth surfaces. By "mild frictional forces", we mean weak lateral forces applied by the dentifrice ingredients to wipe biofilm from the tooth surface, even is the areas and zones between the bristles on the brush. It should also be further noted that the surfactant "foaming agent" may have a role in reducing the surface tension or interfacial forces between the biofilm and the tooth surface and thereby help in loosening its surface adherence.

Without being limited by possible specific modes of action, it is proposed that alone or in combination with other solids, these polysaccharide fibers and fibrils form 3-D entangled network structures when added to aqueous carriers. The resulting compositions are viscoelastic and have a yield stress more than 10 Pa and have an elastic modulus or storage modulus greater than 1000 Pa and preferably higher. Hence, one of the functions of these materials is to modify the tribology and better direct the brushing forces through the dentifrice to achieve appropriate values of these parameters. As a result, it has been found that when compositions of embodiments of the invention are driven by the toothbrush or applicator over the surface of the teeth, the solid particles in conjunction with the network physically remove biofilm, even highly challenging biofilm, from the surfaces being cleaned. This contrasts with most commercial toothpastes, which are generally found to be ineffective in physically increasing removal of plaque biofilm. Another aspect of modifying the dentifrice tribology is to access tight spaces on and between the teeth where a normal toothbrush or conventional toothpaste cannot reach. We also believe that one of the advantages of using natural particulate polysaccharides is that they provide a surface to which plaque biofilm can attach and as a result help its removal when the dentifrice is expectorated after brushing.

These characteristics of the compositions, whether their geometry is fibrous or particulate or something else, significantly improve the physical displacement of oral biofilm, food residues and other undesirable materials from teeth and result in reduced gingivitis, less tooth decay and less tooth loss and hence better oral health.

It is additionally proposed that, during brushing, the lectins on the polysaccharide fibrils make contact and bind with adhesins on the biofilm bacteria, thereby releasing them from lectins in pellicle and on mineral surfaces to which they initially adhere.

Another worthwhile group of oral embodiments are oral care liquid or solid, oral care compositions, which include, for example, chewing gums, tablets, lozenges, mouthwashes, mouth rinses, oral pre-rinses and fluid compositions used with an oral care device, such as a Water Flosser (Waterpik®, Fort Collins, Colorado).

While not wishing to be bound by any specific modes of action, we propose that liquid compositions, such as mouthwashes, remove plaque by similar mechanisms to those we proposed for dentifrices. It is believed that, during thorough rinsing, the fibrils and micro-fibrils from the micro-fibrillated polymeric component penetrate the narrow spaces, such as on and between teeth, along the gum line, in fissures etc. and extricate plaque-biofilm, which would normally be inaccessible. The micro-fibrillated component, in combination with other water absorbing and swelling polymers SAP or NSAP and the organic polymeric thickeners, form a viscoelastic fluid around the water-insoluble, entangled 3D fibril network. Thorough rinsing with a mouthwash embodiment, or other forceful actions of delivery of the viscoelastic fluid to the teeth, forces the liquid composition into areas of the teeth that otherwise are difficult to access.

Among other potential oral care compositions, are a pre-rinse embodiment which helps to dislodge and remove plaque-biofilm prior to and during brushing. A pre-rinse, which adds to the effectiveness of a dentifrice, can be attained by providing shear-thinning (pseudoplastic) viscosity characteristics. While the pre-rinse is in motion during rinsing, the viscosity of the liquid composition is greatly reduced, allowing the liquid to reach virtually all areas of the dentition. After the rinsing action ceases, the composition viscosity will increase, due to the pseudoplastic characteristics, leaving a gel-like film of the rinse on the plaque particularly in places where plaque biofilm builds up, such as between teeth. Subsequent brushing with or without toothpaste will allow residual polymeric plaque dislodging and removing ingredients in the residual film from the mouth pre-rinse to displace and remove more biofilm. Of course, as discussed previously, contributions to biofilm removal are also made by the microcrystalline cellulose, the silicified microcrystalline cellulose, the nanocrystalline cellulose and/or powdered cellulose ingredients in the rinse, which provide mild frictional forces to improve biofilm removal.

Compositions as Described by Numerical Ranges
Following are Example Compositions:
For Dentifrices (Such as Toothpaste)

Dentifrice compositions, of embodiments of the invention, may comprise:
(A) the aforementioned ingredients, which physically dislodge and remove plaque-biofilm comprising:
  (1) From about 0.1% to about 10% of an oral-plaque-biofilm removing, water-insoluble, hydratable, natural or synthetic, fibrillated or micro-fibrillated, polymer, which swells and thickens in an aqueous medium, together with one or more of the following additional plaque removing components:
  (2) From about 0.1% to about 5% of a water-insoluble, micro-crystalline cellulose (MCC) or a water-insoluble, silicified, microcrystalline cellulose (SMCC) (the concentration could be larger in the case of a chewing gum or a dry dosage form);
  (3) from about 0.1% to about 5%, of a synthetic, superabsorbent polymer (SAP), which may be surface cross-linked but does not have to be, or a natural, super absorbent polysaccharide (NSAP), and which swells and thickens in an aqueous medium;
  (4) from about 0.1% to about 10% of a natural or synthetic, water-insoluble, nanocrystalline cellulose polymer (CNC), derived by acidification or oxidation of a natural or synthetic cellulose;
  (5) from about 0.1% to about 4% of one or more water-soluble, organic, polymeric thickeners (PT), selected from an alkali metal or ammonium salt of a polyacrylic acid, xanthan gum, carrageenan gum, an alginate salt, sodium carboxymethyl cellulose, hydroxymethyl cellulose, hydroxyethyl cellulose and hydroxypropyl cellulose;
  (6) from about 0.1% to about 15% of a natural or synthetic, water-insoluble, powdered cellulose (PC).
(B) Functional dentifrice ingredients, which deliver the additional cleaning, oral care, health care and aesthetic benefits expected of a dentifrice composition comprising:
  (i) From about 5% to about 65% of an abrasive;
  (ii) From about 0.1% to about 2.0% of a flavoring agent;
  (iii) Optionally, from about 0.05 to about 1% of a sweetener, selected from saccharin; sodium saccharin, sucralose, aspartame, *Stevia*, potassium acesulfame, neotame, thaumatin, sodium cyclamate;
  (iv) Optionally, from about 0.2% to about 2.0%, preferably from about 0.4% to 2.0% of a surfactant;
  (v) Optionally, from about 0.1% to about 2.0% of a preservative;
  (vi) Optionally, from about 0.2% to about 2.0%, preferably from about 0.5% to about 1.5%, of a buffer to provide a pH between about 3.5 and 9.5, the exact pH range chosen will depend on the fluoride chosen, if there is one, and the needs of other ingredients selected;
  (vii) Optionally, sufficient colorant, such as an FD&C dye, or an opacifier, such as titanium dioxide, to impart a desirable color or whiteness to the dentifrice
  (viii) Optionally, from about 0.05% to about 1.0% of an emulsifier
  (ix) Optionally, a fluoride source, selected from sodium fluoride, sodium mono-fluorophosphate, stannous fluoride and an amine fluoride, in an amount to provide from about 0.025% to about 1% of fluoride-ions;
(C) And additionally, may also comprise one or more of the following optional performance broadening agents, selected from:
  (x) A tartar control agent, present in a concentration of from about 0.1% to about 5%, selected from the following: a complex phosphate salt, zinc citrate, zinc lactate, zinc chloride, an alkali metal polyacrylate, and an ammonium polyacrylate salt, alkali metal gluconate and an ammonium gluconate salt;
  (xi) A tooth desensitizing agent selected from about 0.1% to about 7% of potassium nitrate salt, from about 0.1% of a strontium salt and a stannous salt;
  (xii) A non-abrasive stain removing agent selected from sodium citrate, and a complex phosphate salt.
  (xiii) A non-abrasive tooth whitening agent the ingredient selected from hydrogen peroxide, carbamide peroxide. sodium percarbonate, and sodium perborate.
  (xiv) A breath deodorizing component such as Eucalyptol, Zinc Chloride, Methyl Salicylate, Thymol, Menthol.
(D) the composition is mixed, suspended, dispersed, emulsified or partially dissolved in about 4% to about 50% of a carrier selected from one or more of the following:
  (xv) water,
  (xvi) a humectant selected from glycerin, sorbitol, 1,2 propylene glycol. 1,3 propanediol, polyethylene glycol, sorbitol, polypropylene glycol, erythritol, and xylitol.
  (xvii) (in the case of a tooth powder or a chewing gum) a powdered flake or solid substance selected from one or more of the following: a solid, a gum and a powder. Cellulose, micro-cellulose, hydrated silica, precipitated silica, amorphous silica, precipitated silica, a silica xerogel, polyethylene glycol with a molecular weight above about 650, sorbitol, mannitol, maltitol, isomalt, calcium sulfate, gypsum, magnesium sulfate, hydrated magnesium silicate, talc, sodium bicarbonate, bentonite, sodium carbonate, calcium carbonate, dicalcium phosphate dihydrate, anhydrous dicalcium phosphate, calcium pyrophosphate, tricalcium phosphate, calcium metaphosphate, a gum bases, a wax, stearic acid.

For Liquid Dosage Form (Such as Mouthwash)

Oral liquid and other compositions of embodiments of the invention, may comprise:

(A) ingredients, which physically dislodge and physically detach plaque-biofilm including:
  (1) from about 0.02% to about 8% of an oral, plaque-biofilm removing, water-insoluble, hydratable, natural or synthetic, fibrillated or micro-fibrillated, polymer, which swells and thickens in an aqueous medium, together with one or more of the following additional plaque removing components:
  (2) From about 0.1% to about 5% of a water-insoluble micro-crystalline cellulose (MCC) or a water-insoluble silicified microcrystalline cellulose (SMCC),
  (3) from about 0.1% to about 5%, of a synthetic surface cross-linked superabsorbent polymer (SAP), or a natural, super absorbent, polysaccharide (NSAP), and which swells and thickens in an aqueous medium,
  (4) from about 0.1% to about 2% of a natural or synthetic water insoluble nanocrystalline cellulose polymer (CNC) derived by acidification or oxidation of a natural or synthetic cellulose
  (5) from about 0.1% to about 4% of one or more water-soluble, organic, polymeric thickeners (PT), selected from an alkali metal or ammonium salt of a polyacrylic acid, xanthan gum, guar gum, carrageenan gum, sodium carboxymethyl cellulose, hydroxymethyl cellulose, hydroxyethyl cellulose and hydroxypropyl cellulose, an alkali metal or ammonium alginate salt;
  (6) from about 0.1% to about 15% of a natural or synthetic water-insoluble powdered cellulose (PC).
(B) functional ingredients for liquid compositions, which deliver the additional cleaning, oral care, health care, breath deodorizing, and aesthetic benefits expected of a complete oral care, composition comprising:
  (iii) Optionally, from 0.01% to about 0.5% an antimicrobial agent selected from chlorhexidine, cetylpyridinium chloride, benzethonium chloride and benzalkonium chloride, and essential oils, which include menthol, methyl salicylate, thymol, and eucalyptol,
  (iv) From 0% to about 2% of a surfactant
  (i) From about 0.05 to about 2.0% of a flavoring agent,
  (ii) From about 0.01% to about 1% of a sweetener,
  (v) Optionally, a pH buffer
  (vi) Optionally, a fluoride source, selected from sodium fluoride, sodium mono-fluorophosphate, stannous fluoride and an amine fluoride, in an amount to provide from about 0.025% to about 0.5% of fluoride ions;
  (vi) Optionally, an emulsifier
  (viii) Optionally a preservative,
  (ix) Optionally a colorant,
(C) And additionally, may comprise one or more of the following optional performance broadening agents selected from:
  (x) From about 0.1% to about 2% of a tartar control agent selected from the following: a complex phosphate salt, zinc citrate, zinc lactate, zinc chloride, an alkali metal polyacrylate, an ammonium polyacrylate salt, an alkali metal gluconate, an ammonium gluconate salt;
  (xi) Potassium nitrate, a strontium salt, a stannous salt
  (xii) A whitening agent selected from hydrogen peroxide, sodium perborate,
  (xiii) Breath deodorizing components selected from 0.05 to 0.7% cetyl pyridinium chloride, and the essential oils, such as eucalyptol, methyl salicylate, thymol, and menthol, And the above ingredients may be mixed, dispersed, suspended or partially dissolved in
(C) a carrier selected from:
  (i) Water;
  (ii) ethanol;
  (iii) a powder, a flake or solid substance selected from one or more of the following: a solid, a gum and a powder, Cellulose, micro-cellulose, hydrated silica, precipitated silica, amorphous silica, precipitated silica, a silica xerogel, polyethylene glycol with a molecular weight above about 650, sorbitol, mannitol, maltitol, isomalt, calcium sulfate, gypsum, magnesium sulfate, hydrated magnesium silicate, talc, sodium bicarbonate, bentonite, sodium carbonate, calcium carbonate, dicalcium phosphate dihydrate, anhydrous dicalcium phosphate, calcium pyrophosphate, tricalcium phosphate, calcium metaphosphate, a gum bases, a wax, stearic acid.
  (iv) and a humectant selected from glycerin, sorbitol, 1,2 propylene glycol, 1,3 propanediol, polyethylene glycol, sorbitol, polypropylene glycol, erythritol, and xylitol;

An oral care composition of embodiments of the invention may comprises an effective amount of a fibrillated or micro-fibrillated, natural or synthetic, water-insoluble, hydratable, polymer (MFC), which swells and thickens in an aqueous medium to form a viscoelastic fluid and which physically removes plaque biofilm from oral surfaces.

Another oral composition of embodiments of the invention may comprise (A) 0.05% to 8% of an oral plaque-biofilm-dislodging and removing, natural or synthetic, water-insoluble, hydratable, polymer (MFC), which swells and thickens in an aqueous medium to form a viscoelastic fluid which physically dislodges and removes plaque biofilm from oral surfaces, together with (B) one or more of the following biofilm removing components:
  (i) From about 0.1% to about 5% of a particulate, water-insoluble, micro-crystalline cellulose (MCC) or a particulate, water-insoluble silicified micro-crystalline cellulose (SMCC);
  (ii) From about 0.1% to about 5% of a particulate, synthetic, cross-linked, Super Absorbent Polymer (SAP), which swells and thickens in an aqueous medium;
  (iii) From about 0.1% to about 5% of a particulate, natural, non-cross-linked Superabsorbent Polymer (NSAP), which swells and thickens in an aqueous medium;
  (iv) From about 0.1% to about 2% of a water-insoluble, particulate, nano-crystalline cellulose polymer (CNC), derived, for example, by acid hydrolysis of natural or synthetic cellulose;
  (v) From about 0.1% to about 4% of a water-soluble, organic, polymeric, thickener (PT), selected from one or more of the following: an alkali metal or ammonium salt of a polyacrylic acid, an alkali metal or ammonium alginate salt, xanthan gum, guar gum, carrageenan gum, sodium carboxymethyl cellulose (CMC), methyl cellulose (MC), hydroxymethyl cellulose (HMC), hydroxyethyl cellulose (HEC), hydroxypropyl cellulose (HPC) and hydroxypropyl methyl cellulose (HPMC).

(vi) A natural or synthetic water-insoluble powdered cellulose (CP).

The aforementioned plaque-biofilm dislodging and removing oral compositions can be mixed, absorbed, dispersed, suspended, emulsified or dissolved, to form a paste, a gel, a cream, a liquid, a powder, a gum or a solid with carrier ingredients (C), comprising the following:

(i) A solid substance, a powder, a flake or a gum, including one or more of the following: cellulose, micro-cellulose, hydrated silica, precipitated silica, amorphous silica, precipitated silica, a silica xerogel, a polyethylene glycol with a molecular weight above about 650, sorbitol, mannitol, maltitol, isomalt, calcium sulfate, gypsum, magnesium sulfate, hydrated magnesium silicate, talc, sodium bicarbonate, bentonite, sodium carbonate, calcium carbonate, dicalcium phosphate dihydrate, anhydrous dicalcium phosphate, anhydrous calcium pyrophosphate, tricalcium phosphate, calcium metaphosphate, a gum base, a wax, stearic acid;

(ii) From about 0.5% to about 25% ethanol (iii) From about 10% to about 95% water (iv) From about 5% to about 80% of a humectant selected from glycerin;

sorbitol; 1,2 propylene glycol; 1,3 propanediol; polyethylene glycol with a molecular weight between 250 and 650; polypropylene glycol; erythritol; and xylitol.

An embodiment can be a dentifrice in the form of a toothpaste, tooth-gel, dental-cream, tooth-liquid or tooth powder, which maximizes the ability of the toothbrush or other suitable applicator to physically remove plaque-biofilm from teeth during brushing. Included in dentifrice embodiments are a prophylaxis paste, a prophylaxis gel, a prophylaxis powder for in-office stain removal and polishing of teeth by a dental professional. Another dentifrice embodiment is a professionally prescribed or applied high fluoride oral gel for patients at high risk of dental caries or who exhibit signs of early carious lesions such as white spots.

A dentifrice composition of these embodiments, may comprise from about 0.1% to about 6% of a fibrillated or micro-fibrillated, natural or synthetic, water-insoluble, hydratable, polymer (MFC), which swells and thickens in an aqueous medium to form a viscoelastic fluid, and which physically removes plaque biofilm from oral surfaces.

The dentifrice composition can optionally comprise one or more of the following additional plaque-biofilm removing components comprising:

(i) From about 0.1% to about 5% of a particulate, water-insoluble, micro-crystalline cellulose (MCC) or a particulate water-insoluble silicified micro-crystalline cellulose (SMCC);

(ii) From about 0.1% to about 5% of a particulate, synthetic cross-linked Super Absorbent Polymer (SAP), which swells and thickens in an aqueous medium;

(iii) From about 0.1% to about 5% of a natural, particulate, non-cross-linked Superabsorbent Polymer (NSAP), which swells and thickens in an aqueous medium;

(iv) From about 0.1% to about 2% of a water-insoluble, particulate, nano-crystalline cellulose polymer (CNC), derived, for example, by acid hydrolysis of natural or synthetic cellulose;

(v) From about 0.1% to about 4% of one or more of a water-soluble, organic, polymeric, thickener (PT), selected from one or more of the following: an alkali metal and ammonium salt of a polyacrylic acid, an alkali metal and ammonium alginate salt, xanthan gum, guar gum, carrageenan gum, sodium carboxymethyl cellulose (CMC), methyl cellulose (MC), hydroxymethyl cellulose (HMC), hydroxyethyl cellulose HPMC), hydroxyethyl cellulose (HEC, (vi) From about 0.1% to about 15% of a natural or synthetic water-insoluble powdered cellulose (CP).

In addition, the dentifrice may comprise one or more the following functional dentifrice ingredients, which deliver the additional cleaning and oral health care and safety benefits expected of a dentifrice composition comprising, (D):

(i) From about 5% to about 65% of an abrasive (ii) From 0.2% to about 2% of a surfactant selected from sodium lauryl sulfate, sodium lauroyl sarcosinate, cocamidopropyl betaine and sodium lauryl sulfoacetate;

(iii) Optionally, a fluoride source, selected from sodium fluoride, sodium mono-fluorophosphate, stannous fluoride and an amine fluoride, in an amount to provide from about 0.025% to about 1% of fluoride-ions.

(iv) Optionally from about 0.5% to 8% of an inorganic thickener (v) Optionally, from about 0.2% to 0.5% chlorhexidine gluconate for professionally applied or prescribed dentifrices.

Furthermore, dentifrices and other oral compositions comprise one or more of the following auxiliary ingredients (E), which provide an enjoyable experience, pleasant aesthetics, and an optimum environment for effectiveness and safety in the mouth:

(i) From about 0.2% to about 2.5% of a buffer salt to provide a pH between about 3.5 and 9.5. The exact pH range chosen may depend on the fluoride source and the needs of other ingredients;

(ii) From about 0.1% to about 2.0% of a flavoring agent;

(iii) From about 0.05 to about 1% of a sweetener, selected from saccharin; sodium saccharin, sucralose, aspartame, Stevia, potassium acesulfame, neotame, thaumatin, sodium cyclamate;

(iv) From about 0.1% to about 2.0% of a preservative;

(v) Sufficient colorant, such as an FD&C dye to impart a desirable color to the dentifrice; From about 0.2 to about 2.5% of an opacifier, such as titanium dioxide, to whiten to the dentifrice (vi) From about 0.05% to about 1.0% of an emulsifier.

The dentifrices may also include one or more of the following optional performance broadening agents (F), selected from:

(i) From about 0.1% to about 5% of a tartar control agent selected from the following: an alkali metal or ammonium complex phosphate salt, zinc citrate, zinc lactate, zinc chloride, zinc acetate, an alkali metal gluconate and an ammonium gluconate salt;

(ii) A tooth desensitizing agent selected from about 0.1% to about 7%, preferably 6%, of potassium nitrate and from about 0.1% to about 3% a strontium salt and a stannous salt;

(iii) A non-abrasive stain removing agent selected from sodium citrate, and a complex phosphate salt (iii) A non-abrasive stain removing agent selected from sodium citrate, and a complex phosphate salt Therapeutic dentifrices are intended for in dental-office application by professionals, or for prescription, and include prophylaxis pastes, gels, powders and subgingival plaque removing compositions. Also included are high fluoride treatment gels, which comprise from about 0.15% to about 1.0% fluoride ion, for patients at high risk of caries or with signs of early carious lesions. These compositions may also comprise one or more of the functional, (D), auxiliary (E) and carrier ingredients (C) described above. The presence of a fluoride functional ingredient can be especially important in a prophylaxis paste, which tends to be highly abrasive. Fluoride can promote remineralization of areas of the enamel or dentin, which may have been abraded during the prophylaxis. Additionally, the chlorhexidine gluconate functional ingredient may be helpful for subgingival professional plaque removing formulations to kill any residual pathological bacteria left behind by the sub-gingival biofilm dislodging composition. Chlorhexidine is not generally recommended for routine use in OTC (Over the Counter) conventional toothpastes, because of its tendency to stain teeth and because of its potential to promote the formation of resistant bacterial strains when regularly employed.

The dentifrice ingredients comprising, plaque biofilm dislodging and removing ingredients, (A) and (B), functional components (D), auxiliary constituents, (E), and performance broadening agents, (F), are mixed in a suitable carrier (C), to form a mixture, a suspension, dispersion, an emulsion, partial solution, a solid, a powder, a liquid, a paste, a gel, or a cream comprising one or more of the following:
  (i) A solid substance, a powder, a flake or a gum, selected from one or more of the following: cellulose, microcellulose, hydrated silica, precipitated silica, amorphous silica, precipitated silica, a silica xerogel, a polyethylene glycol with a molecular weight above about 650, sorbitol, mannitol, maltitol, isomalt, calcium sulfate, gypsum, magnesium sulfate, hydrated magnesium silicate, talc, sodium bicarbonate, bentonite, sodium carbonate, calcium carbonate, dicalcium phosphate dihydrate, anhydrous dicalcium phosphate, anhydrous calcium pyrophosphate, tricalcium phosphate, calcium metaphosphate, a gum base, a wax, a stearic acid;
  (ii) From about 0.5% to about 25% ethanol
  (iii) From about 10% to about 95% water
  (iv) From about 5% to about 80% of a humectant selected from glycerin; sorbitol; 1,2 propylene glycol; 1,3 propanediol; polyethylene glycol with a molecular weight between 250 and 650; sorbitol; polypropylene glycol; erythritol; and xylitol, mixed, suspended, dispersed, emulsified or partially dissolved in a carrier.

Example Compositions

| Ingredient | Composition 1 | Composition 2 |
|---|---|---|
| | Percent by weight | |
| MFC | 1.8 | 2.0 |
| MCC | 1.5 | 1.2 |
| SAP | 0.5 | 0.5 |
| Carboxymethyl cellulose | 1.0 | 0.3 |
| Carbopol 974 (Polyacrylate) | 0.0 | 0.7 |
| Pumice | 35.5 | 0.0 |
| Magnesium silicate | 0.0 | 32.0 |
| Glycerin | 30.0 | 34.0 |
| Flavor | 0.4 | 0.5 |
| Sodium Saccharin | 0.4 | 0.4 |
| Monosodium phosphate | 1.0 | 0.9 |
| Disodium phosphate | 0.5 | 0.4 |
| Sodium saccharin | 0.4 | 0.4 |
| Sodium fluoride | 2.2 | 2.2 |
| Water | 24.8 | 20.6 |

| Ingredient | Composition 3 | Composition 4 | Composition 5 |
|---|---|---|---|
| | Percent by weight | | |
| MFC | 3.5 | 6.0 | 1.8 |
| MCC | 2.0 | 2.0 | 1.5 |
| SAP | 1.0 | 0.5 | 0.4 |
| Xanthan gum | 0.4 | 0.3 | 0.0 |
| Carboxymethyl cellulose | 0.0 | 0.5 | 0.4 |
| Carbopol 974 (Polyacrylate) | 0.5 | 0.5 | 0.4 |
| Xylitol | 15.0 | 0.0 | 0.0 |
| Erythritol | 0.0 | 0.0 | 12.0 |
| 1,3 Propanediol | 20.0 | 0.0 | 0.0 |
| Glycerin | 10.0 | 32.26 | 35.0 |
| Flavor | 0.4 | 0.5 | 0.4 |
| Monosodium phosphate | 1.0 | 0.7 | 0.8 |
| Disodium phosphate | 0.5 | 0.3 | 0.4 |
| Sodium saccharin | 0.4 | 0.4 | 0.4 |
| Benzalkonium chloride | 0.0 | 0.04 | 0.0 |
| Cetylpyridinium chloride | 0.0 | 0.0 | 0.07 |
| Sodium fluoride | 0.24 | 0.24 | 0.24 |
| Water | 45.06 | 56.2 | 50.06 |

| Ingredient | Concentration (%) | | | |
|---|---|---|---|---|
| | MFP Paste | SnF2 Paste | NaF Paste | NaF Bak soda |
| Mincrofibrillated cellulose | 1.500 | 1.700 | 1.500 | 0.800 |
| MCC | 1.500 | 1.200 | 2.500 | 0.600 |
| SAP | 0.000 | 0.000 | 0.500 | 0.200 |
| Hydroxypropyl Methyl cellulose | 0.500 | 0.000 | 0.000 | 0.000 |
| Hydroxyethyl cellulose | 0.000 | 0.250 | 0.300 | 0.500 |
| Water | 22.040 | 24.116 | 28.000 | 18.000 |
| CMC | 0.000 | 0.000 | 0.000 | 0.000 |
| Saccharin | 0.100 | 0.150 | 0.300 | 0.600 |
| Sucralose | 0.050 | 0.030 | 0.040 | 0.070 |
| Sorbitol (70%) | 0.000 | 0.000 | 0.000 | 0.000 |
| Glycerin | 25.000 | 45.000 | 34.000 | 19.000 |
| Propylene glycol | 15.000 | 3.000 | 15.320 | 0.000 |
| PEG-8 | 0.000 | 0.000 | 0.000 | 2.000 |
| Sodium bicarbonate | 0.000 | 0.000 | 0.000 | 55.490 |
| Dicalcium phosphate dihydrate | 31.000 | 0.000 | 0.000 | 0.000 |
| Sodium citrate | 0.000 | 2.500 | 0.000 | 0.000 |
| Citric acid | 0.000 | 0.500 | 0.000 | 0.000 |
| Tetrasodium pyrophosphate | 0.000 | 1.800 | 0.000 | 0.000 |
| Flavor | 0.900 | 0.900 | 0.850 | 1.000 |
| Hydrated silica abrasive | 0.000 | 15.000 | 14.000 | 0.000 |
| Hydrated silica thickener | 0.000 | 0.500 | 0.500 | 0.000 |
| Titanium dioxide | 0.400 | 0.400 | 0.250 | 0.000 |
| Sodium lauryl sulfate | 1.250 | 1.000 | 0.700 | 0.500 |
| Sodium lauroyl sarcosinate 35% | 0.000 | 0.000 | 0.000 | 1.000 |
| Cocamidopropyl betaine (35%) | 0.000 | 0.000 | 1.000 | 0.000 |
| Stannous fluoride | 0.000 | 0.454 | 0.000 | 0.000 |
| Stannous chloride dihydrate | 0.000 | 1.500 | 0.000 | 0.000 |
| Sodium fluoride | 0.000 | 0.000 | 0.240 | 0.240 |
| Sodium monofluorophosphate | 0.760 | 0.000 | 0.000 | 0.000 |
| Total | 100.000 | 100.000 | 100.000 | 100.000 |

| Ingredient | Concentration (%) | | | |
|---|---|---|---|---|
| | Fluoride Whitening Mouthwash | Oral-freshening Mouthwash | Oral Pre-rinse | Anti-plaque Oral Rinse |
| Micro-fibrillated cellulose | 0.200 | 0.150 | 0.200 | 0.250 |
| Micro-crystalline cellulose | 0.400 | 0.500 | 0.450 | 0.300 |
| Hydroxypropyl methyl cellulose | 0.100 | 0.000 | 0.15 | 0.000 |
| Psyllium gum | 0.000 | 0.000 | 0.150 | 0.000 |
| Sodium fluoride | 0.020 | 0.000 | 0.000 | 0.000 |
| Water | 67.800 | 66.912 | 76.530 | 67.030 |
| Alcohol | 5.000 | 0.000 | 0.000 | 0.000 |
| Sorbitol 70% | 2.830 | 8.000 | 0.000 | 5.000 |
| Glycerin | 0.000 | 20.000 | 19.500 | 16.000 |
| Propylene glycol | 20.000 | 3.000 | 2.000 | 10.000 |
| Hydrogen peroxide (100%) | 2.500 | 0.000 | 0.000 | 0.000 |
| Flavor oils | 0.000 | 0.200 | 0.200 | 0.350 |
| Monosodium orthophosphate | 0.000 | 0.000 | 0.150 | 0.000 |
| Disodium phosphate | 0.000 | 0.000 | 0.000 | 0.000 |
| Citric acid | 0.000 | 0.100 | 0.000 | 0.100 |
| Sodium citrate | 0.000 | 0.050 | 0.000 | 0.100 |
| Cetyl pyridinium chloride | 0.000 | 0.000 | 0.000 | 0.070 |
| SLS | 0.000 | 0.000 | 0.300 | 0.000 |
| Poloxamer 407 | 0.260 | 0.400 | 0.000 | 0.000 |
| Sodium Saccharin | 0.350 | 0.200 | 0.250 | 0.300 |
| Sodium benzoate | 0.200 | 0.050 | 0.200 | 0.000 |
| Benzoic acid | 0.150 | 0.130 | 0.000 | 0.000 |
| Potassium sorbate | 0.000 | 0.000 | 0.000 | 0.300 |
| Sucralose | 0.060 | 0.050 | 0.070 | 0.030 |
| Zinc acetate | 0.000 | 0.000 | 0.000 | 0.020 |
| Eucalyptol | 0.000 | 0.092 | 0.000 | 0.000 |
| Thymol | 0.000 | 0.064 | 0.000 | 0.050 |
| Menthol | 0.070 | 0.042 | 0.000 | 0.100 |
| Methyl Salicylate | 0.060 | 0.060 | 0.000 | 0.000 |
| Total | 100.000 | 100.000 | 100.000 | 100.000 |

B. Functional Oral Care Ingredients

This section further describes the various functional oral care ingredients for dentifrices and other compositions. Other than the polymeric plaque dislodging ingredients, dentifrice functional ingredients include a dentifrice abrasive, a fluoridating agent, a surfactant, an inorganic thickener, an organic thickener, a flavoring agent, a sweetener, a pH buffer as well as a component capable of reducing plaque adhesion, a tartar control agent, a calcium deposits control agent, a tooth desensitizing agent, a whitening agent, a water activity modifier, a preservative, in amount that provides a dentifrice benefit. In one dentifrice embodiment, it is preferred to include the four following dentifrice ingredients from the aforementioned list:

(a) between about 5% and about 50% of a dentifrice abrasive,
(b) between about 0.1% and about 2.0% of one or more dentifrice surfactants,
(c) between about 0.1% and about 1.0% of a sweetener, and
(d) between about 0.1% and about 2.0% of a flavorant.

Dentifrice embodiments generally contain between about 0.025% to about 1% by weight of active fluorine. Dentifrices for regular twice daily home use typically contain from about 0.08% to about 0.25% soluble fluorine compound. Prophylaxis pastes, used in the dental office, typically contain from about 0.2% to about 1.0% fluoride. The permitted contents for fluoride toothpaste in the USA are identified in Table 1 herein.

Additional Embodiments

Embodiment compositions may be formulated with the stannous fluoride system so that optimal physical removal of plaque biofilm, fluoridation of enamel and deep delivery of the SnF2 (or other compounds) at gum-teeth interface can be achieved. The subgingival deep delivery of SnF2 can be further enhanced by adjusting the type and concentration of surfactants (e.g., SLS) to a higher concentration which may be about 1.5% if necessary. Not wishing to be bound by an explanation, it is believed that physical forces applied by embodiment composition during brushing can further promote deeper transport of SnF2 to 3 to 6 mm in the subgingival space between gum and teeth. This can be analyzed by using surface analysis techniques (e.g., TOF-SIMS or the like). In addition, the high level cleaning provided by embodiment composition is also believed to facilitate transport of SnF2 such that more effective fluoridation and antimicrobial properties can be delivered in various places. The combined benefits of embodiment compositions can result in less caries, tooth decay, lower tooth loss, stronger enamel and less gingivitis or periodontitis.

Embodiment methods and compositions may be targeted to obtain effective stain removal from teeth during brushing compared to prior art commercial toothpastes. It has been discovered that abrasives such as hydrated silica or other particles (e.g., calcium carbonate or the like) can become incorporated and entrapped within the network structure of embodiment composition even when said composition becomes diluted with saliva or water during brushing, i.e., particles do not separate from the network structure upon dilution. Collectively, the solids of the composition including fibrillated materials, particulate materials (e.g., MCC), abrasives (e.g., hydrated silica) and particulate SAP or their combinations can form a composite pad that can penetrate, wipe, transfer and remove stain from teeth. Here the particles in the composition populate the surface of the composition pad (not as a slurry) at some surface density and capture and remove the stain as the composition is moved over the surface of teeth by the action of the brush.

Accordingly, embodiment compositions may be designed and tailored to effectively remove stain from teeth according to a new embodiment method that is different and distinct from commercial toothpaste because in conventional toothpastes the toothpaste transforms into a low viscosity slurry by saliva dilution as described elsewhere herein. In commercial toothpastes, slurried abrasive particles separate from the toothpaste and are dragged over the surface of teeth by brush bristle tips where the movement of such particles helps in removing stain as articulated well by Lewis et al (Lewis, R., Dwyer-Joyce, R. S., & Pickles, M. J. (2004). Interaction between toothbrushes and toothpaste abrasive particles in simulated tooth cleaning. Wear, 257(3-4), 368-376). It is believed that embodiment method and composition of the invention may provide means to more effectively remove stain from teeth and that the new mechanism may provide larger contact surface area between the composition and stained teeth compared to methods or compositions of prior art.

Compositions of embodiments may effectively remove tea, coffee and food stain from teeth and in this regard they can be used routinely on a daily basis or less frequently, for example once a week. The compositions can also be formulated in the form of prophylaxis paste or gels that can be used by consumers as necessary for example once per week to prevent excessive accumulation of stain. In addition, the compositions can be formulated as a prophylaxis paste for used by hygienists in a dental office setting or for cleaning dentures or dental appliances. When embodiment compositions are formulated as toothpastes, they may provide effective control of both stain and plaque biofilm as described elsewhere herein.

Embodiment compositions may be formulated to produce chlorine dioxide (C102) during and after tooth brushing or application inside the oral cavity. Sodium chlorite or other appropriate precursor of chlorine dioxide can be included in embodiment compositions at concentration from about 50 ppm to 1000 ppm or more; the concentration of precursor can be adjusted to allow for reaction with cellulose ingredients during storage. The composition may be adjusted to have a pH above 8.0 to about 10.5 using an appropriate buffer (e.g., phosphate buffer) to prevent the degradation of the chlorine dioxide precursor during shelf storage. Once the embodiment composition is applied, the precursor would react with natural acids in the oral cavity to produce nascent chlorine dioxide in solution. The produced C102 is expected to be effective over a wide range of pH in the mouth, for example between 3.0 to 7.5. The combination of high-level plaque biofilm removal found with embodiment composition as demonstrated elsewhere herein and the produced C102 may be expected to enhance the following functions: 1) killing organisms that cause biofilm; 2) neutralizing mouth odor as in halitosis; 3) enhancing whitening of teeth due to oxidative bleaching; 4) preventing tartar formation with routine use; 5) removing previously accumulated tartar. Accordingly, embodiment compositions that can deliver C102 may be formulated according to the present invention. Different dosage form compositions are anticipated, including: toothpaste; tooth gels; mouth rinses; mouth pre-rinses; prophylaxis pastes and gels. These can be made available for consumer and professional use. Persons skilled in the art may vary concentrations and level of ingredients to make effective C102-producing compositions based on the teaching of the present invention.

Embodiment oral compositions wherein abrasives are incorporated within the microstructure of the fibrillated network are disclosed. We discovered that abrasive silica particles (or other abrasives such as calcium carbonate) become a part of the embodiment composition and that such particles do not separate even at high dilution levels, as described elsewhere herein. This discovery may provide better stain and biofilm removal during cleaning such as during tooth brushing or mouth rinsing. This discovery may enable making formulations with different dosage forms (paste, gel, slurry, pre-rinse, rinse, etc.) where the abrasive particles are securely held within the fibrillated entities without transforming into liquid slurries due to dilution as in the case with prior art commercial toothpastes. It is thus feasible to make mouth rinses with a small concentration of highly fibrillated MFC, wherein abrasive particles are incorporated within the fibrillated entities. Such composition may be effective in removing stain and biofilm from interproximal spaces, surfaces or teeth, at and below the gum line. Without being bound by explanation, it is believed that the flow of abrasive-loaded fibrillated entities may create shear forces that can provide cleaning when such entities flow in the interproximal space, which would enhance cleaning of these inaccessible areas. Persons skilled in the art can manipulate and optimize compositions of various dosage form to obtain similar cleaning results based on the teaching of this invention.

In an embodiment, compositions of the invention may facilitate more effective fluoridation of tooth enamel when used regularly or when used in conjunction with high-concentration prescription fluoride preparations. Embodiment compositions would typically include 0.24% fluoride, which is the FDA recommended dose in the United States. It is believed that embodiment compositions may facilitate better fluoridation of enamel because such compositions can provide high-level removal of organic residues from teeth surfaces. These organic layers, if they are allowed to remain, may retard optimal fluoridation due to diffusional resistance of fluoride ions into the enamel. In another scenario, when teeth are brushed regularly with an embodiment composition and when the level of cleaning is high, it is believed that upon application of 5000 ppm or 10000 ppm fluoride gel/solution, the rate of uptake and fluoridation may be enhanced such that enamel build up and strengthening would be faster and more effective. Not wishing to be bound by an explanation, it is believed that regular brushing with an embodiment composition along with regular application of therapeutic high fluoride level preparation would be effective in repairing weak enamel.

Experimental Methods and Procedures

Embodiments of the invention are further described but are in no way limited by the Examples described herein. It is useful to first describe procedures that form the basis for the Examples.

A. Preparation of Biofilms for Assessing Dental Plaque Removal Effectiveness

In the work reported here, several types of biofilms were prepared using protocols. These are: 1) BBF (build up biofilm); 2) Single-species biofilm; and 3) Dual-species biofilm. The bacterial species used to grow biofilms and substrates used are provided in Table 2.

BBF is a form of biofilm representing the fact that biofilm that has occasional exposure to conditions and compounds that makes it become tougher and more difficult to remove from teeth. Dental biofilm which is not removed with daily brushing accumulates and then calcify overtime forming Tartar as described herein. BBF was found to be especially valuable in the present work for evaluating the removal effectiveness of plaque biofilm from various surfaces and substrates, and in comparing prior art commercial toothpastes and embodiment compositions. For the present work, BBF is grown over a period of 8 days, and at several times during preparation it is exposed to a low concentration of glutaraldehyde, which imparts crosslinking, strength and adhesion. Embodiment BBF has proven to be very useful for in vitro assessment of biofilm removal and in the development of embodiment methods and compositions.

TABLE 2

Methods for growing in vitro biofilm

| | BBF | Single-species biofilm | Dual-species biofilm |
| --- | --- | --- | --- |
| Organisms used | E. faecalis (Gram+; ATCC 29212) P. aeruginosa (Gram−; ATCC 27853) | S. mutans (Gram+; ATCC 700610) | A. naeslundii (Gram+; ATCC 12104) S. oralis (Gram+; ATCC 9811) |
| Growth medium | ATS2015 | BHI with 2% sucrose | THB |
| Substrate and Geometry | PTFE or HA Tube | HA discs, PTFE tubing | HA discs, Silicone tubing |

B preparation method/protocol: A bacterial suspension of 1 G FU/mL was prepared with *Enterococcus faecalis* and *Pseudomonas aeruginosa* cultured on blood agar (BA) plates at 37° C. in Artificial Test Soil (ATS2015) on Day 1. A pre-disinfected 3.7 mm Inside Diameter PTFE tubing and pump tubing set up was filled with bacterial suspension in ATS2015. Both ends were connected to make a closed circuit. The bacterial suspension was circulated in the tubing by a peristaltic pump at 72 mL/hr at room temperature. After 48 hours, on Day 3, the bacterial suspension was drained. The tubing was rinsed with sterile tap water, fixed with 1:50 diluted glutaraldehyde for 2 min, rinsed again with sterile tap water, filled with sterile RO water, and left on the tray overnight. On Day 4, the tubing was filled with bacterial suspension and connected to the peristaltic pump for 4-hour circulation. Then, the tubing was rinsed, fixed with 1:50 diluted glutaraldehyde for 2 min, rinsed again, and left overnight. The procedure of Day 4 was repeated on Day 5 except for the last step. Instead of filling it with sterile RO water, the tubing was filled with bacterial suspension and was connected to the peristaltic pump for circulation over the weekend. On Day 8, the tubing was drained, rinsed, fixed with undiluted glutaraldehyde for 20 min, and rinsed again. This is a modification of the published method according to: Alfa M, Ribeiro M M, Da Costa Luciano C, Franca R, Olson N, DeGagne P, and Singh H. 2017. A novel polytetrafluoroethylene-channel model, which simulates low levels of culturable bacteria in buildup biofilm after repeated endoscope reprocessing. Gastrointest. Endosc. 86(2):442-451.

Single-species dental biofilm preparation method/protocol: Prior to coating the hydroxyapatite (HA) discs with pellicle, the HA discs were etched for 60 seconds in 0.12 M HCl, soaked in saturated sodium carbonate for 30 seconds, followed by 60 seconds in 1% phytic acid. To develop pellicles on the HA discs, the discs were suspended in 1.2% mucin in distilled water at 40° C. for 15 min. Next, the solution was removed with the discs from the heated solution and then cooled down slowly to 36° C. The discs were removed from the solution and dried at 37° C. for 30 min. This cyclic treatment was repeated for 2 days to properly form pellicles to simulate the dental biofilm that normally grow in the mouth in the presence of saliva.

*Streptococcus mutans* suspension was prepared by growing single colony overnight in brain heart infusion (BHI) broth at 37° C. Overnight grown culture was diluted to 1:5 in BHI. The prepared discs were placed in a 12-well plate filled with 2.5 mL of 2% sucrose in diluted *S. mutans* suspension and were incubated at 37° C. until use. Every 24 hours, the media was replaced by fresh media. This biofilm was prepared as an adaptation of: Khosravi Y, Kandukuri R D P, Palmer S R, Gloag E S, Borisov S M, Starke E M, Ward M T, Kumar P, De Beer D, Chennu A, and Stoodley P. 2020. Use of an oxygen planar optode to assess the effect of high velocity microsprays on oxygen penetration in a human dental biofilms in-vitro. BMC Oral Health 20:230.

Dual-species biofilm preparation methods/protocols: Prior to coating the HA discs with pellicle, the discs were etched for 60 sec in 0.12 M HCl, soaked in saturated sodium carbonate for 30 sec, followed by 60 sec in 1% phytic acid. To develop pellicle on the HA discs, the discs were suspended in 1.2% mucin in distilled water at 40° C. for 15 min. Next, the solution was removed with the discs from the heat and cooled down to 36° C. slowly. The discs were removed from the solution and dried at 37° C. for 30 min. This cyclic treatment was repeated for 2 days.

This method was modified from Verkaik et al., 2010. *Streptococcus oralis* was cultured on Todd-Hewitt broth (THB, Sigma-Aldrich) aerobically and *Actinomyces naeslundii* in Chopped meat broth (Anaerobic systems, CA) under anaerobic conditions, both at 37° C. Strains were precultured in an overnight batch culture and inoculated in a second culture which was grown for 16 hrs. Bacterial concentrations were adjusted to $10^8$ CFU/mL in adhesion buffer (2 mM potassium phosphate, 50 mM potassium chloride, and 1 mM calcium chloride, pH 6.8) with 20% growth medium (THB for *S. oralis* and Chopped meat broth for *A. naeslundii*). Three methods were used to prepare the dual species dental biofilm, as follows:

Method 1: Dual-species grown on HA discs: Prepared discs were aligned on a rubber strip and placed in 6 inch manifold connected to inlet and outlet. A peristaltic pump was used to flow media for 2.5 mL/min through inlet to manifold to outlet for drain. Adhesion buffer was flowed first through the manifold for 30 min. For dual-species biofilm development, *A. naeslundii* suspension was flowed next for 2 hrs then the flow was switched to adhesion buffer for 30 min and to *S. oralis* suspension for 2 hrs to initiate co-adhesion. Then the flow was switched to THB and operating until use. All buffer and media were kept in water bath at 33° C. for entire experiment.

Method 2: Dual-species grown on HA discs: Prepared discs were soaked in adhesion buffer for 15 min. The adhesion buffer was replaced by *A. naeslundii* suspension and incubated on a rocker at 37° C. for 2 hrs. The discs were soaked in adhesion buffer again for 15 min and incubated in *S. oralis* suspension at 37° C. for 2 hours on the rocker. Finally, the discs were placed in a petri dish filled with fresh THB and were incubated on the rocker anaerobically at 37° C. until use.

Method 3: Dual-species biofilm grown in tubes: This method pertains to preparation of a dual species biofilm using two organisms known to make dental plaque biofilm that was proven to provide a quantitative measure of cleaning teeth according to the References cited herein. *Streptococcus oralis* was cultured in Todd-Hewitt broth (THB, Sigma-Aldrich) aerobically and *Actinomyces naeslundii* was cultured in Chopped meat broth (Anaerobe Systems, Morgan Hill, CA) under aerobic conditions; both were incubated at 37° C. Strains were pre-cultured in an overnight batch culture and inoculated in a second culture which was grown for 16 hrs. 3 ft of PTFE tubing was connected to 2 ft of silicone tubing to make a closed circuit which was connected to a peristaltic pump for circulation. The PTFE and silicone tubing was filled with 0.25% mucin on the day before experiment to form pellicles to mimic and simulate the natural formation of dental plaque biofilm in the mouth. On the next day, the mucin solution was drained and the tubing set was filled with a second culture of *A. naeslundii* and fluid was circulated at Room Temperature at a flowrate of 3 mL/min. After 1 hr, the second culture of *A. naeslundii* was replaced by a second culture of *S. oralis* and circulated for 1 hr. The bacterial suspension was replaced by 0.1% yeast medium in Brain Heart Infusion (BHI) broth. The media was replaced every 24 hrs. The silicone tubing was replaced after 3 days due to leakage. After 10 days of circulation, the silicone replacement tubing was used for testing biofilm removal using the tube geometry as described elsewhere herein. According to this method, the biofilm was developed inside the silicone tubing by bacterial transfer taking place due to the action of circulation. The resulting biofilm was found to adhere well to the surface of silicone tubing as evidenced by dark blue staining after exposing it to a 0.5% solution of methylene blue in water. References for dual-species biofilms: (1) Verkaik M J, Busscher H J, Rustema-Abbing M, Slomp A M, Abbas F, and Van der Mei H C. 2010. Oral biofilm models for mechanical plaque removal. Clin. Oral. Invest. 14:403-409. (2) Gusnaniar, Hizal F, Choi C-H, Sjollema J, Nuryastuti T, Rustema-Abbing M, Rozenbaum R T, Van der Mei H C, Busscher H J, and Wessel S W. 2018. Transmission of monospecies and dual-species biofilms from smooth to nanopillared surfaces. Appl. Environ. Microbiol. 84(15) e01035-18.

It has been discovered that the buildup biofilm (BBF) model can simulate two forms of challenge biofilm: 1) biofilm plaque that grows and accumulates during a regular brushing pattern (e.g., every 12 hours to two days) and 2) older biofilm plaque that has transformed into tartar or calculus over longer time (e.g., >1 week). The first form (plaque biofilm) can be referred to as "young biofilm," which may be soft and sticky and easy to remove with brushing, for example. The second form develops in areas where biofilm was not fully removed by routine brushing and then transforms into tartar. Tartar contains calcified dead bacteria, and it becomes highly adhering to teeth surfaces and it cannot be removed by brush bristles.

During the process of growing BBF, the bacterial suspension is circulated in a tube or is made to flow over a substrate (e.g., hydroxyapatite disc) over a period of from 4 days (BBF4) to 8 days (BBF8) as detailed under "Methods." As the bacterial suspension is circulated in a horizontal tubing, some bacteria continually sediment and accumulate on the bottom of the tube due to gravity. Over time, the biofilm that forms on the tube bottom become stronger and more adherent compared to the biofilm that forms on the sides and ceiling of the tube. Because the biofilm is treated periodically with a dilute glutaraldehyde solution during the biofilm growth process, the bottom biofilm transforms into a deposited structure similar to the tartar or calculus. The upper biofilm transforms into a less robust material more representative of plaque biofilm. The combination of sedimentation and periodic crosslinking with glutaraldehyde used to make BBF can be made to simulate both biofilm plaque and tartar in a single tube or experiment. In an embodiment, BBF made can be used to assess and quantitate the removal of both plaque biofilm and tartar by tailoring the age and form of the biofilm. Biofilm removal assessment methods are described under Methods.

BBF has proven to be an excellent surrogate for dental plaque biofilms because it adheres well to various different surfaces including both hydroxyapatite and polymer surfaces. Also, BBF has been compared with biofilms made with dental/oral plaque organisms was found to provide equivalent biofilm removal results. The dual-species dental biofilm was used to validate the methods used to assess the removal effectiveness from the surface of hydroxyapatite (which is equivalent to tooth enamel as described elsewhere herein).

B. Substrate Materials

For many experiments about cleaning compositions either for toothbrushing or for other cleaning applications, the biofilm was grown on the internal surfaces of polymeric tubes. In many experiments, the tubes of the test segment were made of (Teflon®). This is particularly true for biofilm that is grown from *S. mutans* bacteria. The trade name Teflon frequently refers to polytetrafluoroethylene (PTFE). However, there are also two other similar compounds, having similar properties, that can also be referred to using the trade name Teflon, namely, Fluorinated Ethylene Propylene (FEP), and Perfluoroalkoxyalkane (PFA). Polytetrafluoroethylene is not transparent, while FEP is transparent. The use of a transparent tube material, especially if the biofilm challenge is stained prior to testing, permits visual observation of the progress of cleaning while the cleaning process is occurring, and permits photographic documentation of the results of cleaning, after the completion of the cleaning process, without destroying the tube. However, for experiments reported herein using Teflon, the material used was polytetrafluoroethylene.

For some experiments, biofilm was grown on the internal surface of tubing that made of silicone rather than Teflon. This was done for growing dual-species biofilm (*A. naeslundii* and *S. oralis*), which is considered (Verkaik et al) to be a very good simulant for assessing biofilm removal in non-contact brushing evaluation. It was found that this dual-species biofilm did not adhere to Teflon tubing, but adhered to silicone tubing appropriately for use in testing using the technique of flow through a tube as described herein.

For some experiments, in order to most closely correspond to toothbrushing, the substrate used was hydroxyapatite. Hydroxyapatite (a form of calcium phosphate) is a ceramic material that is similar to tooth enamel. Hydroxyapatite is commercially available from Himed, Old Bethpage, NY. During manufacturing of the hydroxyapatite tube, the processing conditions were adjusted to produce a surface that represents tooth enamel especially well. Therefore, experimental results involving this hydroxyapatite surface are an especially good representation of what happens during toothbrushing. Hydroxyapatite is available from this manufacturer in the form of flat discs, which are usable like any other discs. In an embodiment we used hydroxyapatite in the form of tubes having an inside diameter of approximately 0.25 inch and a length of approximately 4 inch (100 mm) to properly assess the biofilm removal from HA using flow in the tube geometry as described herein. In regard to tubes, hydroxyapatite tubes are not flexible and are not transparent. Nevertheless, because of its chemical similarity to tooth enamel, hydroxyapatite in the form of tubes is used for some experiments.

Properties of biofilm such as adhesion strength depend on the surface on which biofilm is grown. Relevant characteristics include not just chemistry but also topology and elasticity of the surface. Teflon is smooth and of course has low-friction and adhesion-resistant properties. Hydroxyapatite, which is a mineral that mimics the physics and surface chemistry of tooth enamel, has a surface that is rougher than Teflon and is partially porous. Therefore, the same biofilm growing on two different surfaces could be different. Bacteria in the mouth are different bacteria from those used to grow BBF. Therefore, BBF on Teflon is not the same as dental plaque on teeth, and the surfaces are different (enamel vs. Teflon). However, we found that the results obtained with BBF were in agreement with those found with the dual species biofilms grown on hydroxyapatite discs.

C. Biofilm Removal Assessment Method Using a Tube Geometry

Several embodiments of the invention include methods for assessing biofilm removal by in vitro methods. The embodiments include: 1) methods of growing BBF in tube geometries; 2) methods of growing biofilms in HA tubes; 3) methods for assessing biofilm removal and evaluating the mechanical parameters from flow parameters, including: pressure drop; shear rate; shear stress; volumetric and linear velocity and related parameters; 4) ranking the results based on a removal effectiveness scale; 5) use of rheometry with a cone and plate geometry or other geometry to assess and measure toothpaste flow-induced biofilm removal from HA discs under defined shear rate and shear stress conditions; 6)

methods to grow dual-species biofilm and use in assessing the effectiveness of biofilm removal with any oral composition, including: toothpastes/dentifrice; tooth gels; mouth rinses, chewing gum or other dosage forms as described elsewhere herein. These embodiments are considered a part of the present inventions.

In experiments described herein, some characterization and screening of candidate compositions is performed using flowing the composition through a round tube, in which the internal walls are coated with bacterial biofilm or other contaminant. Although the luminal tubular geometry is not the same as the geometry of teeth during toothbrushing, the tubular geometry has usefulness because it is a standard and easily reproducible geometry, and because tubes are readily available commercially. For such experiments, as a biological challenge, biofilm is grown on the internal surface of the tube using a prescribed protocol using specified bacteria that are purchased from commercial suppliers.

For many experiments about cleaning compositions either for toothbrushing or for other cleaning applications, the tubes of the test segment were made of (Teflon®) or other composition, for example silicone, acrylic, etc. A typical inside diameter of such a tube was 3.7 mm (0.146 inch). For experiments reported herein using Teflon, the material used was polytetrafluoroethylene. In the experiments described herein, the stain typically used for staining biofilm was methylene blue, or in some cases Crystal Violet, or Rose Bengal.

For tube material that is not transparent, if the biofilm challenge is stained, it is possible to make some overall observations during the cleaning process in real time by observing the general color of the cleaning composition exiting the tube, as a function of time. When there is no longer any presence of the stain color in the cleaning composition that exits the tube, that is an indicator that effective cleaning has probably been accomplished. Furthermore, for a non-transparent tube, if it is desired to have photographic evidence or biological quantitation of the condition of the luminal surface after cleaning (such as by culture or PCR methods), it is possible to cut the tube open and perform visual inspection or recovery followed by culturing, although that entails destroying the tube.

For some experiments, in order to most closely correspond to toothbrushing, the tube used was a tube made of enamel-like hydroxyapatite.

We found that the results obtained with BBF were in agreement with those found with the dual species biofilms grown on hydroxyapatite discs.

Experiments were conducted herein to demonstrate that test results for flow through a Teflon tube are representative of cleaning a hydroxyapatite surface or are representative of toothbrushing. The procedure involved growing a pellicle film on an HA disc followed by growing single or dual species biofilm on the pellicle. This mimics dental plaque on HA discs, and was found to produce results that were in agreement with those obtained with the tube geometry. Removal of biofilm from HA discs was assessed using a cone and plate geometry available on the Anton Paar rotational rheometer. A thin film of toothpaste was placed on the HA disc and the rotating cone was moved to touch the toothpaste and set at a certain distance between the cone (truncated) tip and the bottom plate. The toothpaste completely filled the gap between the biofilm coated plate and the cone. The cone was rotated for 20 seconds at a certain torque or rotational speed and the disc was examined to see if biofilm was removed, as described elsewhere herein.

When performing tube flow experiments, the geometry was the biofilm-coated interior of a tube of circular cross-section, and various potential oral compositions were caused to flow through the lumen of the tube. During such a test, the flowrate and pressure drop per unit length of the cleaning composition are often constrained or measured. Often the biofilm is stained before performing the test, and any remaining biofilm is stained after performing the test.

Build up biofilm (BBF) was grown inside PTFE or silicone tubes having a 3.7 mm Inside Diameter. For flow tests, the "test section" was a 2 inch long segment of this tubing having BBF or other biofilm type on its internal surface. In the experimental setup, the 2 inch long BBF test section of 3.7 mm Inside Diameter was flanked at each end by 1 foot long segments of Tygon® tubing having an Inside Diameter of 3.2 mm. The dental formulation being evaluated was pumped though the series of tubes: 1 foot flanking section, followed by the test section, followed by another 1 foot long flanking section. In some experiments the composition flowing through this test setup was a dental composition at its nominal concentration. In many experiments, the dental composition was diluted with water, usually to 50% of its original concentration, to represent the consistency of toothpaste in the mouth during brushing. This dental composition was pumped by a syringe pump though the series of tubes at a set flow rate of 20 mL/min (which corresponds to an average linear velocity of about 3.1 cm/s in the test section) for a period of 2 minutes. The pressure drop was measured between the two ends of flanking tubing, and a calculation was used to obtain the pressure drop across the test section, taking into account the lengths of the flanking tubing segments and the test section, and their slightly different inside diameters. Immediately after flow of the cleaning composition, 120 mL of rinse water was pumped through the tubes at 90 mL/min.

At the cleaning composition flow rate of 20 mL/min, the pressure drop measured was the total pressure drop for the two flanking sections and the 2-inch long test section. We estimate the pressure gradient in the 2 inch long test section from use of the Hagen Poiseuille equation for laminar flow in a tube:

$$\Delta P = \frac{2\mu L Q}{\pi R^4}$$

Assuming applicability of the Hagen Poiseuille equation to this situation, we can show that the fraction, f, of the total pressure drop that occurs across the test section is given by:

$$f = \frac{\frac{L_2}{D_2^4}}{\frac{2L_1}{D_1^4} + \frac{L_2}{D_2^4}}$$

where D=tube Inside Dimeter, L=length of section, and subscript "1" denotes the flanking tubing segments and subscript "2" denotes the test segment. Substituting values of the respective lengths and diameters, we obtain the fraction of the pressure drop attributable to the test segment as:

$$f=0.045$$

The fraction has this value because in the present setup, the flanking sections were longer than the test section and also had a slightly smaller inside diameter. Then, the pressure gradient in the test segment in units of psi/ft becomes $$\left(\frac{\Delta P}{L}\right)_{test} = \frac{0.045 \Delta P_{total}}{\frac{2}{12}} = 0.27 \Delta P_{total} \text{ psi/ft}$$

where the pressure drop has units of psi and the pressure gradient has units of psi/ft.

For laminar flow of a Newtonian or non-Newtonian fluid, the shear stress at the wall of a circular tube is given by:

$$\tau_w = \frac{R}{2}\left(\frac{\Delta P}{L}\right)$$

This equation is used to estimate the shear stress exerted by the flowing composition at the tube wall of the test segment. Using $V_{ave}$ which is the superficial velocity (volumetric flowrate divided by cross-sectional area) and assuming a parabolic velocity profile, it is possible to calculate the shear rate at the wall, which is dv/dr at r=R. The result can b estimated as:

$$\text{Shear rate at wall, 1/sec} = \frac{8V}{D}$$

It can be noted that these equations are based on an assumption of laminar Newtonian flow. For flow of a non-Newtonian fluid, which is what compositions of embodiments of the invention are, this is only an approximation. However, some of the equations are valid even for non-Newtonian fluids.

D. Protocols for Measuring Biofilm that Remain after Cleaning in a Tube Geometry Results from flow testing were visually characterized on a ranking scale. We designated four cleaning rankings (1 to 4) compared to the positive control (not cleaned).

1=perfectly clean; no spots remaining at all

2=almost as good as 1; but occasional random blue spots of biofilm remain

3=partial removal of biofilm; some biofilm is removed, some remains

4=less than 5% or 10% removal of biofilm or no removal at all

This ranking was used to evaluate the effectiveness of biofilm removal of the experimental and to compare prior art commercial toothpaste compositions with embodiment compositions. This ranking method was used to assess biofilm removal from PTFE tubing, from silicone tubing, and from HA tubing. Sometimes this method also was extended to evaluate HA discs as described in Examples herein.

Figure 3:
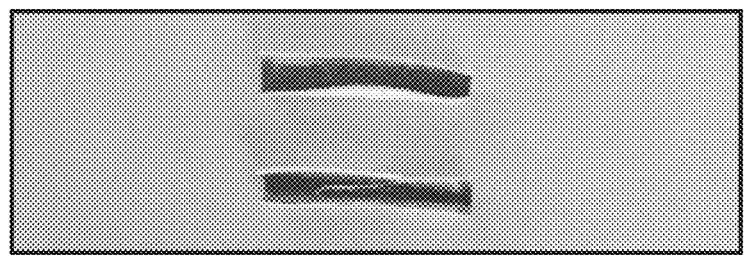
FIG. 3 is a series of photographs of stained biofilm remaining after tube tests in polytetrafluoroethylene tubes, illustrating the ranking of performance.
Figure 3:
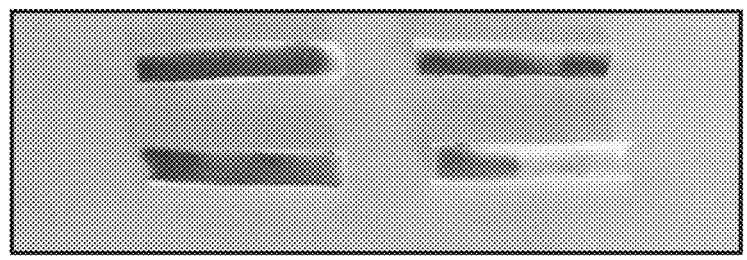
Figure 3:
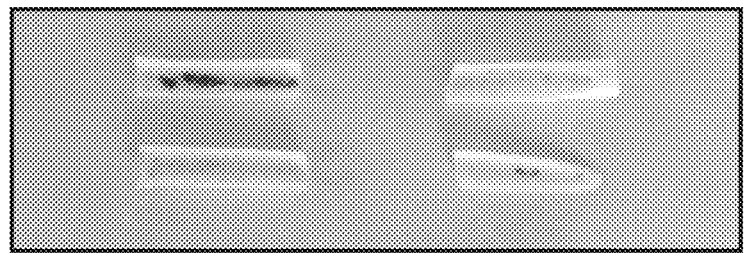
Figure 3:
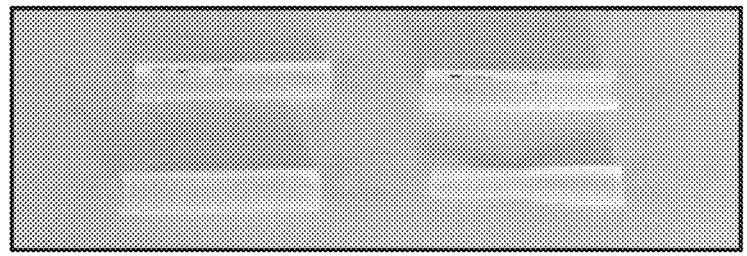
Figure 3:

These ranks were based on visually and microscopically estimating the "Apparent Biofilm Removal" based on the fraction of tube surface area where the biofilm was removed. To describe the extent of biofilm removal in a slightly more quantitative manner, this ranking and the corresponding apparent surface area where the biofilm was removed are summarized in Table 3: FIG. 3 visually illustrates the rankings used in the Examples from actual cleaning experiments.

TABLE 3

| Ranking | Apparent % BBF Removal |
| --- | --- |
| 1 | 100 |
| 2 | 70-99 |
| 3 | 30-69 |
| 4 | 1-29 |
| Positive Control | 0 |

The general procedure includes the following steps: 1) preparing the biofilm in tubing as described under Methods; 2) staining the biofilm with the selected stain (e.g., methylene blue); 3) assessing the amount of biofilm in the tube lumen by the surface area covered with biofilm or by recovering the biofilm by sonication followed by culturing or by PCR (polymerase chain reaction); 4) performing the cleaning with test composition as described under Methods; 5) assessing the residual biofilm that remain on the surface by measuring the uncleaned fraction of surface area (covered by biofilm) using image analysis software as described elsewhere herein; 6) computing percent cleaning or biofilm removal by subtracting percent of surface covered by biofilm from 100; 7) alternatively, assigning a ranking scale to the level of removal based on visual appearance. The ranking scale assigned was from 1 to 4 with 1 being 100% clean and 4 being almost uncleaned, as displayed in FIG. 3.

E. Using Rotational Rheometers to Perform and Test Removal of Biofilm from HA Discs As described elsewhere herein, rheometers are conventionally used to measure rheological properties of materials by placing the materials between two surfaces, with there being relative rotation between the two surfaces, with the rotation being either continuous rotation or oscillatory rotation. Here, we used this device to test the toothpaste flow-induced bacterial biofilm removal.

Figure 2A:
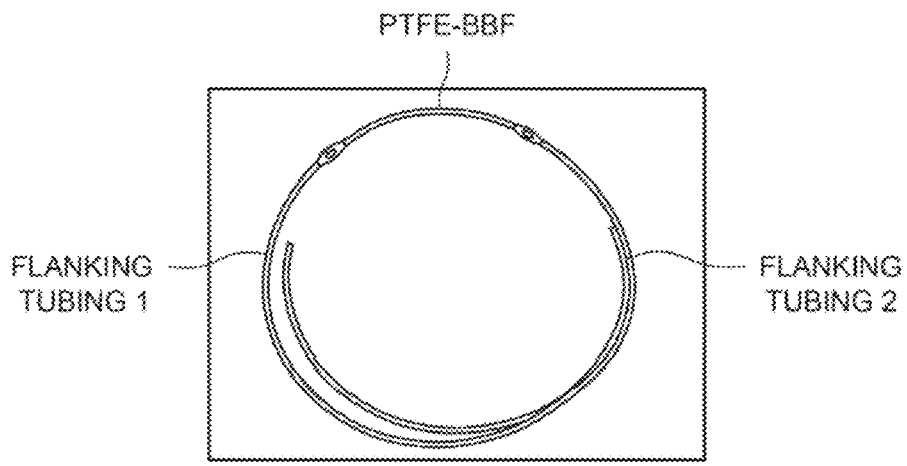
FIGS. 2A and 2B show a diagram of the tubing and flow arrangement used for testing biofilm removal inside a tube.
Figure 2B:
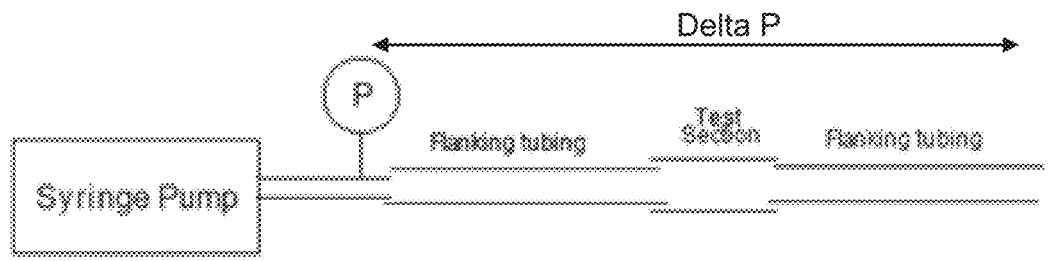
Figure 2C:
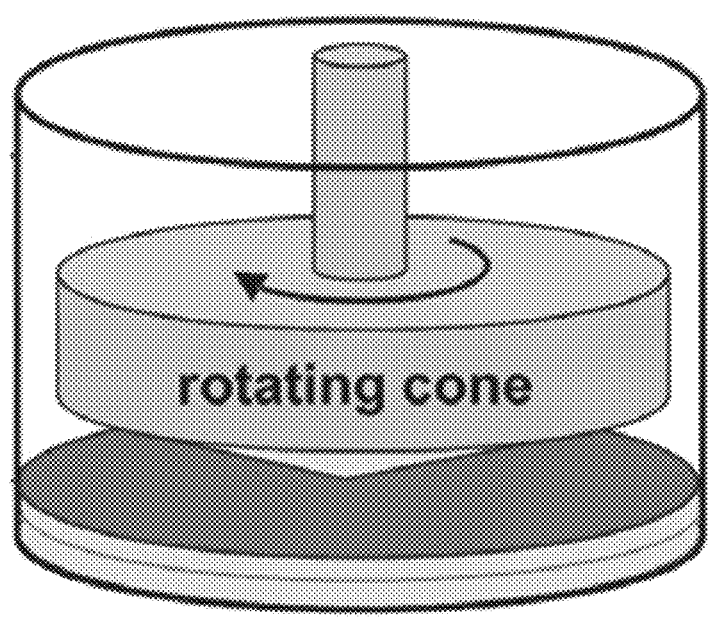
FIG. 2C shows a cone and plate arrangement used for performing tests of biofilm removal using a disc in a rheometer.

In testing for this example (using an Anton Paar MCR 302 rheometer), we used a cone-plate geometry. For the bottom disc of the rheometer configuration, we used an enamel-like hydroxyapatite disc (from Himed) of 1.2 cm diameter. This disc was coated with a biofilm prepared as described elsewhere herein. For the top cone we used a roughened metallic cone plate 25 mm in diameter, having a cone angle of 1 degree. We placed 2 ml of toothpaste on top of the biofilm-coated lower disc, and then we lowered the cone to provide the intended gap size. In this configuration, the gap distance between the cone and the disc was fixed at about 0.050 mm. It can be noted that if the top and bottom plates were both perfectly flat and parallel to each other, the local shear rate would vary as a function of radius, and cleaning towards the outer part of the disc would be better than cleaning near the center. Instead, the conical taper provides a slightly larger gap outboard and a smaller gap near the center of the discs. This variation makes the local shear rate toward the outside of the disc equal to the local shear rate near the center of the disc. (FIG. 2) and hence there is a uniform shear rate applied over the material.

We then rotated the cone with a predetermined value of either shear rate, shear stress, torque or rotational speed. In the case of a constant shear rate, we kept a constant shear rate of about 300 $s^{-1}$. The torque was approximately 1.4 mN-m and the rotational speed was about 50 rotations/min. Rotation was performed for about 20 seconds. We believe these values to be consistent with the typical values experienced during ordinary toothbrushing. After the desired rotation, we analyzed the biofilm removal caused by composition being tested. We tested the embodiment toothpaste, several other commercial toothpastes. In most instances, because of interest in the effects of dilution, the material being tested was diluted to 50% (or occasionally some other fraction) of its nominal or as-purchased composition.

Figure 4B:
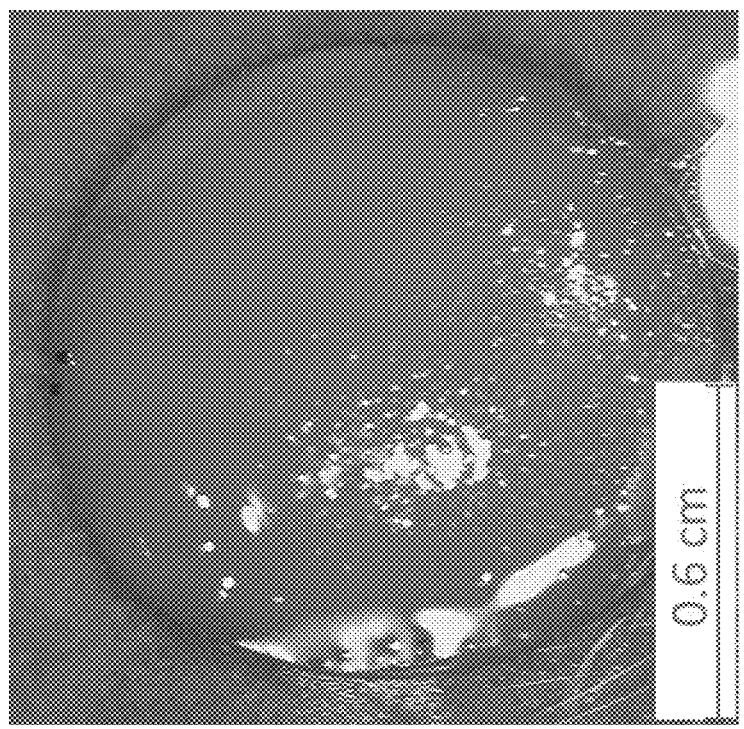
FIG. 4B shows a hydroxyapatite disc after cleaning with an embodiment of the invention.
Figure 4A:
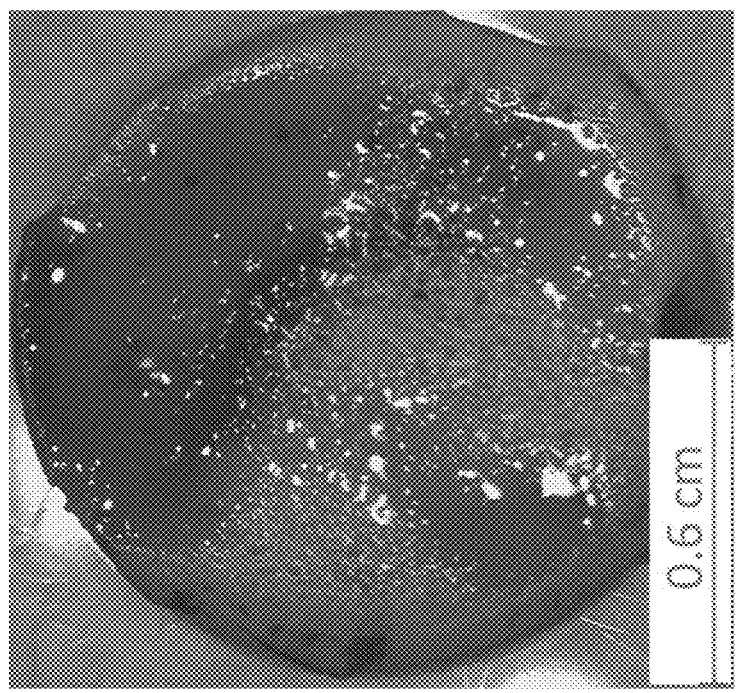
FIG. 4A shows a hydroxyapatite disc

Representative photographic results of typical experiments are shown in FIGS. 4A and 4B. The presence of biofilm is indicated by blue stain [depicted as a darker shade]. It can be seen that formulations of embodiments of the invention (FIG. 4B) clearly remove almost all of the biofilm from the disc. In contrast, with a commercial toothpaste (FIG. 4A), very little biofilm is removed.

We note that the shear rate applied in this test has to be considered only as an approximate shear rate value because, due to equipment and specimen limitations, the top cone is much larger than the bottom plate, whereas ideally they would be of the same size. Nevertheless, this type of experiment provides a very useful set of data.

F. Image Analysis

Images used in the experimentation were taken with a Firefly Model GT700 UV microscope with Bright LED settings (FireflySci Inc., Staten Island, NY). The images were taken over the whole surface area of the HA disc. Beyond simple visual observation, images were inputted to the image processing software ImageJ (public domain, developed by National Institutes of Health). Images were cropped to exclude overlapping sections and portions of the image which did not include the sample. Then the color threshold tool under Image >Adjust >Color Threshold, Dark background was unchecked. Hue, brightness, and saturation were adjusted until the threshold includes all the biofilm on the sample. Hue should be selected to be the blue wavelengths, and saturation and brightness should include major peaks shown in the diagram above the sliders. Then, click select to select all sections with biofilm. To measure, first, go to Analyze >Set Measurements and include Area. Then go to Analyze >Measure to figure out the number of biofilm-covered pixels. Return to the color thresholding tool Image >Adjust >Color Threshold and expand selection to include the whole surface area of the HA disc being analyzed. An easy way to do this is after deleting all non-relevant parts of the image in the first step (overlapping sections and sections off the sample) expand hue and saturation to include the full spectrum and expand brightness from 1-255. Click select and this should select the entire sample. Go to Analyze >Measure and it will print the number of pixels in the entire section. Repeat this process with each image until the entire surface area of the HA disc has been analyzed. Sum the area covered by biofilm and sum the total area of each image. The parameter reported as percent covered is calculated as covered pixels/total pixels.

G. Rheological Measurements

In experiments described herein, some characterization and screening of candidate compositions is performed using measurements of rheology.

Rheology describes the behavior of fluids in terms of elastic behavior and viscous behavior. These measurements were also taken on the Anton Paar MCR 302 Rheometer, using an experimental apparatus in which round flat plates rotate relative to each other. Rheological measurements characterize a fluid by measuring its viscosity and by describing its elastic properties by the Storage Modulus G' and describing its viscous properties by its Loss Modulus G" (both having units of Pa or similar units).

Tribology characterizes the interaction of solid surfaces that are in relative motion with respect to other solid surfaces, often with a fluid substance also present between the solid surfaces. Such information is relevant to frictional interaction, which is relevant for removal of biofilm. Tribological properties can be characterized in terms of friction factor, which is a ratio of tangential force to normal force, just as in classical physics. This is typically presented in the form of a Stribeck plot, in which the friction factor is plotted as a function of relative velocity between the respective solid surfaces, as is discussed elsewhere herein.

In the present work, tribological measurements are taken using an Anton Paar MCR 302 Rheometer, using an experimental apparatus in which a sphere is rotated around a vertical axis while being contacted by smaller pins at three equally distributed locations. For some experiments the pins were made of Teflon. For other experiments the pins were made of PDMS (polydimethylsiloxane). PDMS is more deformable as compared to Teflon and this may better reflect the situation of tooth-bristle interaction during tooth brushing. It is well known in tribology that the chemistry and mechanical properties of the ball and pin surfaces affect friction measurements. It is thought that the deformable PDMS pins can better mimic behavior of toothpaste between a hard surface (like the tooth enamel) and a softer material (like the bristles of the toothbrush). We specifically consider sliding velocities larger than 1 cm/s because such velocities can simulate the useful range of velocities encountered during tooth brushing.

In embodiments of the invention, the rheology is generally similar to the rheology of commercial toothpastes.

H. Measurement of Water Activity

The following is the procedure that was used for measuring Water Activity. Place humidity chamber in oven at 23 degrees Celsius and wait for temperature to stabilize. Record initial humidity and temperature readings once temperature has stabilized. Place a 5 gram sample in a small glass petri dish at the bottom of humidity chamber. Secure fan 8 inches above sample and turn on to highest setting pointing the fan towards sample. Record humidity and temperature readings at minutes: 1, 3, 5, 8, 10, 15, and 20. Humidity stabilizes between 18-20 minutes. Record final humidity reading once stabilized.

These procedures and protocols were used in the following Examples.

Example 1: Dual-Species Biofilm Removal Testing—Embodiment Compositions Versus Commercial Toothpastes, by Tube Testing Dual-species biofilm (*A. naeslundii* and *S. oralis*) was grown in silicone tubing as described elsewhere herein. Verkaik et al found that this biofilm is a better simulant for assessing biofilm removal in non-contact brushing evaluation than is *S. mutans* biofilm. Herein, we found that this dual species dental biofilm can provide an excellent surrogate biofilm for evaluating embodiment compositions and for providing valid comparison with commercial toothpastes.

Figure 5:
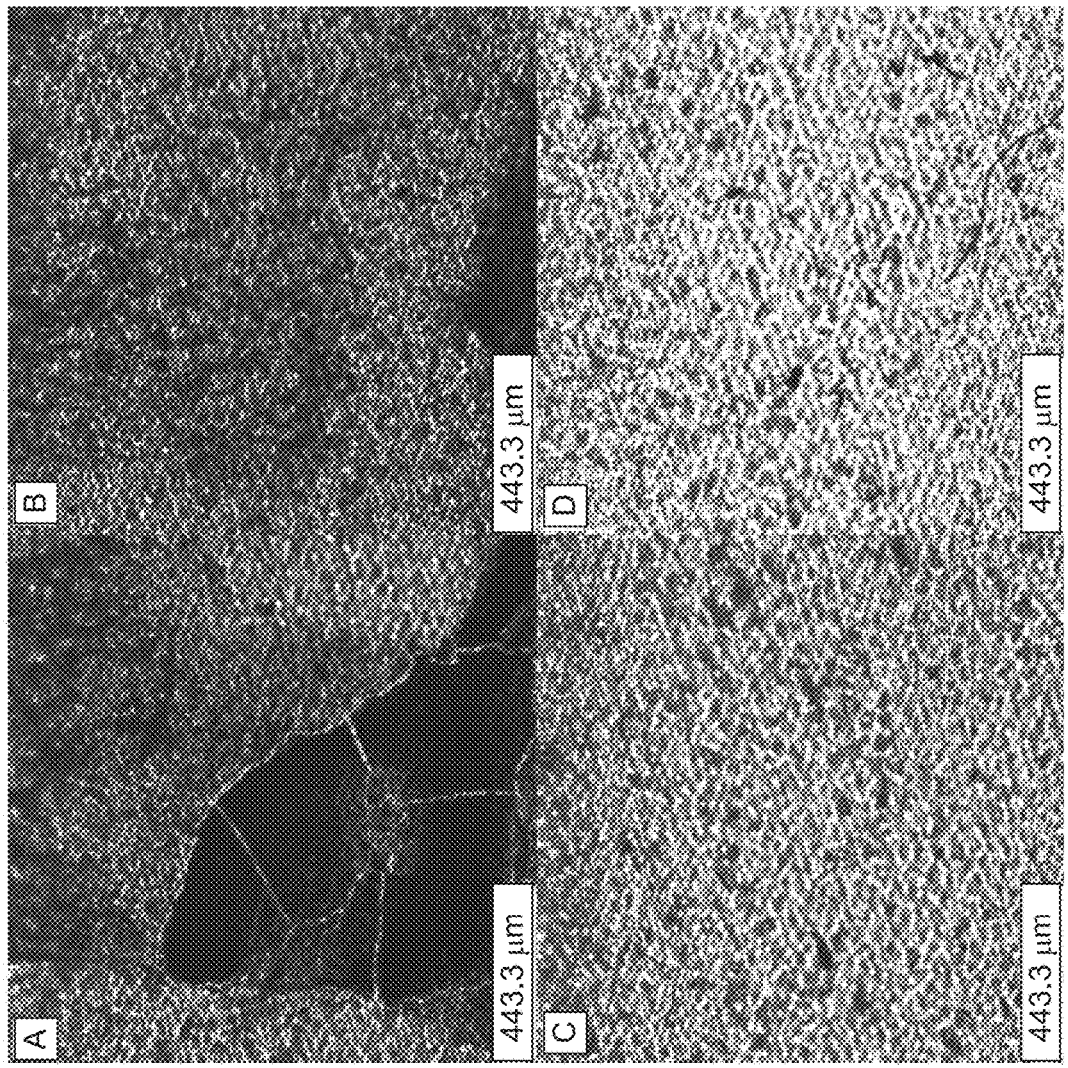
FIG. 5 shows, for commercial toothpaste, cleaning results on a silicone tube, and, for an embodiment of the invention, cleaning results on a silicone tube.

CP1 and inventive embodiment TP #46, both at 50% concentration (diluted with water), were used as the test composition to determine the effectiveness of removal of biofilm after dilution with saliva or water as typically happens during tooth brushing. The flow rate and cleaning duration were as described under methods for the tube geometry. After coating with biofilm and cleaning according to the experiment, cross-sections of the tubes were cut using a razor blade to a length of 1.5-2.0 cm and then were bisected horizontally. Samples were analyzed at 10× magnification using a Leica DM18 microscope with an HC FL PLAN 10/0.25 Dry objective. Consecutive bright field images were taken over the entire sample length using the microscope's native Leica-K5-14401188 camera. The biofilm, stained with methylene blue, was identified visually as having a blue color under the microscope when viewed via the eyepiece, and this corresponds to a dark grey color in the images. ImageJ software was used to select and then measure areas covered in biofilm. The biofilm-covered areas were summed for each field across the length of the sample, and a total remaining coverage was determined as covered area divided by the total area of the tube segment. It was determined that 36.70% of the area remained covered by biofilm after cleaning with Commercial Toothpaste 1 (CP1), whereas only 0.55% of the area remained covered when cleaned with embodiment composition (TP #46). In FIG. 5, two images of each sample are shown to demonstrate different places on the same sample, showing that biofilm exists over the whole tube. The dark grey areas indicate surface covered with biofilm, while black spots indicate surface deformities or roughness of the silicone tube. Commercial Toothpaste images (A and B) show significant remaining biofilm on the surface of the material in varying thickness as well as in shallow and deep roughness and grooves. Images C and D show that TP #46 removed all the biofilm including from surface features while leaving some biofilm remaining in the bottom of cracks and crevices.

The results of this Example clearly show that embodiment composition (TP #46) was able to remove 99.45% of the biofilm surface area, compared to 63.3% for commercial toothpaste CP1. These results are when the dual species biofilm was used as the challenge dental biofilm simulant. These (dual species biofilm on a silicone tube) results are in agreement with the results obtained with the BBF simulant biofilm in a Teflon tube geometry. FIG. 5 displays image comparison of TP #46 and CP1 along with % residual surface area remained covered with biofilm after cleaning.

Example 2: Testing Using Hydroxyapatite Tubes

Figure 6:
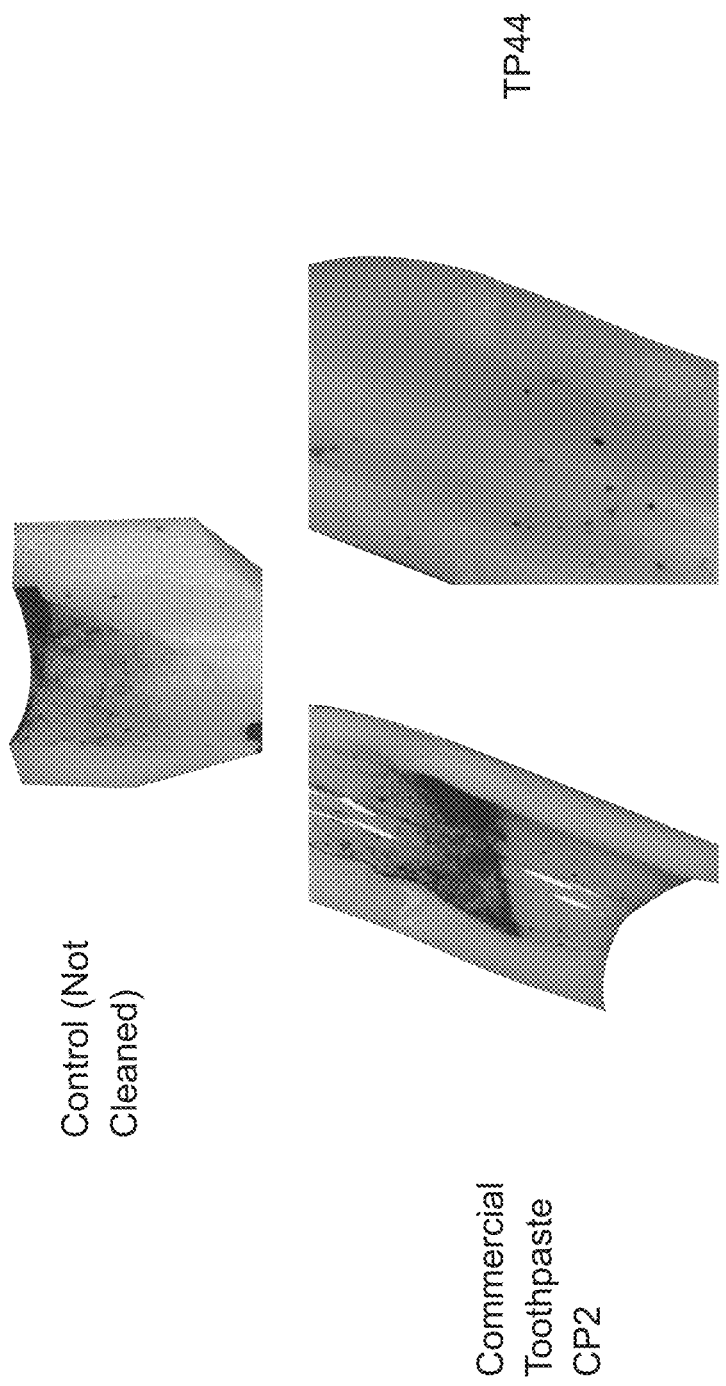
FIG. 6 shows interiors of hydroxyapatite tubes before cleaning (control), after cleaning with commercial toothpaste, and after cleaning with a composition of an embodiment of the invention.

Build up biofilm (BBF) was grown on the luminal surface of HA tubes by the recirculation method as described under Methods. The removal procedure was performed and assessed in the tube geometry by flowing the test compositions inside the tubing as described elsewhere herein. The HA material was selected to simulate biofilm removal effectiveness with test compositions from teeth enamel and to compare the results with BBF was grown on Teflon or silicone tubing or on HA discs. BBF-coated HA tubes were stained with methylene blue to the reveal the biofilm and to assess the removal effectiveness. Comparison of BBF removal from HA tubing was made with embodiment composition (TP #44) and commercial toothpaste CP1. FIG. 6 shows that TP #44 was effective, while commercial toothpaste CP1 was clearly ineffective in removing BBF from HA surface. This data is in agreement with other experiments made with BBF-coated Teflon and BBF-coated silicone tubing. In addition, these results are in agreement with dual-species biofilm removal from HA discs as provided in another Example herein.

Figure 7:
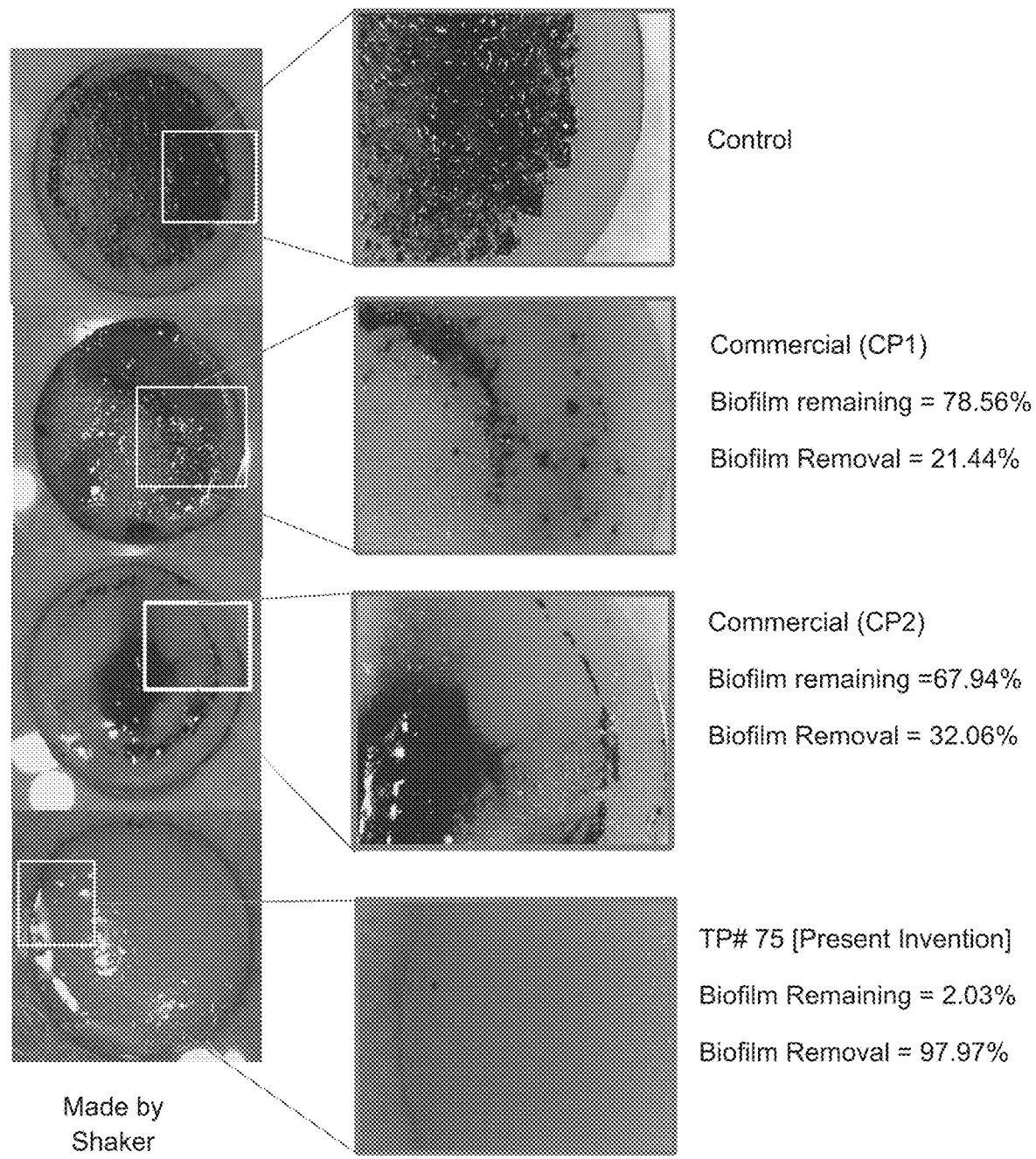
FIG. 7 shows HA discs as a control and after cleaning with various compositions, with the biofilm being made by the shaker method. High magnification images were used for determining biofilm coverage using the previously described process along with 5-7 other fields of the sample. Location of the image taken is shown with the box.
Figure 8:
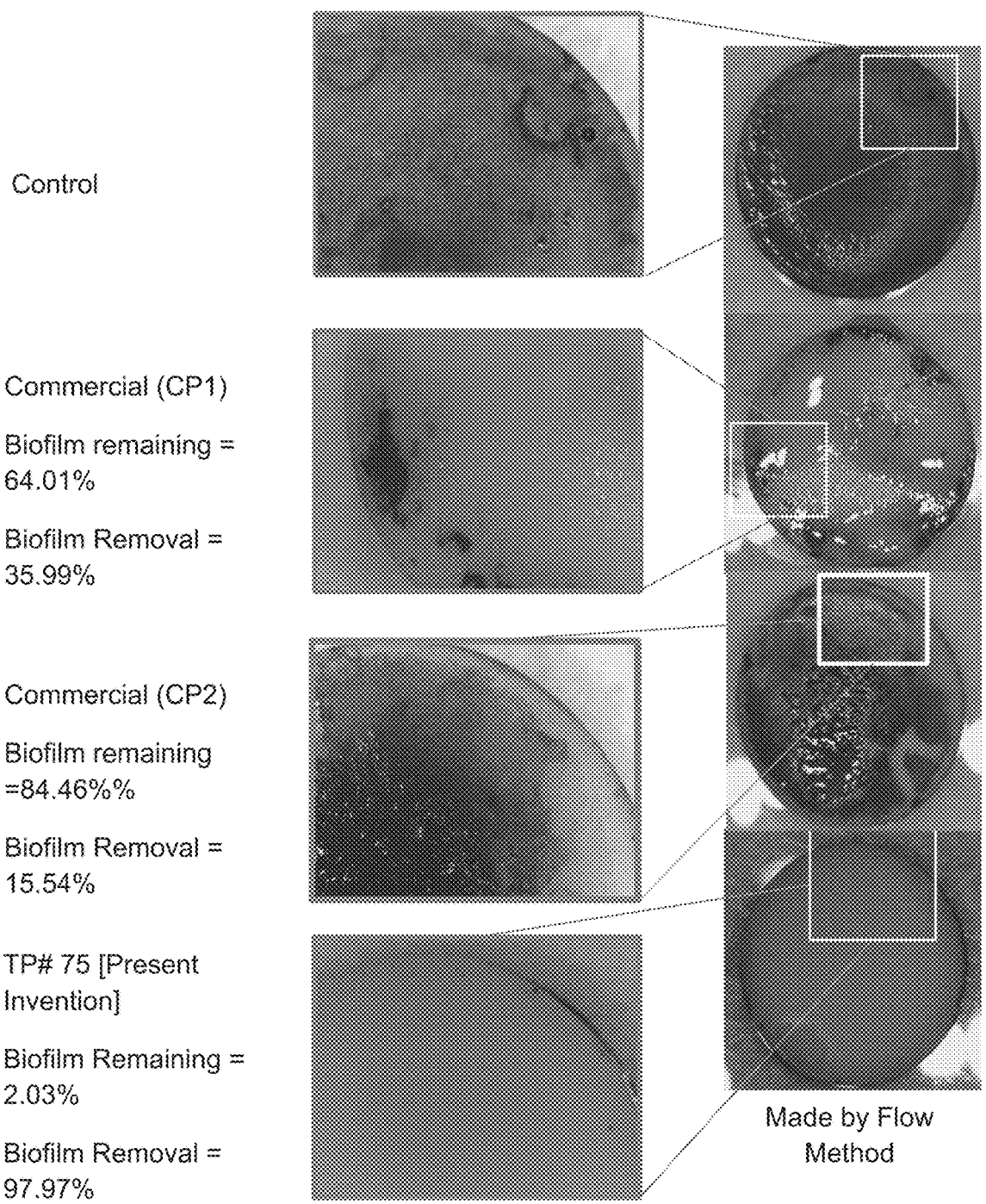
FIG. 8 shows HA discs as a control and after cleaning with various compositions, with the biofilm being made by the flow method. High magnification images were used for determining biofilm coverage using the previously described process along with 5-7 other fields of the sample. Location of the image taken is shown with the box.

Example 3: Removal of Dual-Species Biofilm from Hydroxyapatite Discs Under Constant Shear Stress Using the Rheometer and Methods of Quantitation Dual-species dental biofilm was grown on HA discs as described under "Methods". The biofilm was stained with 0.3% methylene blue (MB) for 10 minutes and then rinsed with water to remove residual MB and reveal the biofilm before cleaning. This served as a control. Removal effectiveness of the dual biofilm was assessed, with rotation being performed at constant shear stress using the cone and plate arrangement and the configuration as described under "Methods." The cleaning time was 20 seconds. After this procedure, the HA discs were rinsed with water and then were evaluated with special microscopic techniques and image analysis to determine the removal effectiveness of the dual-species biofilm with either embodiment compositions or commercial toothpastes. The surface of HA discs is assessed with image analysis software as described elsewhere herein. Percent cleaning was calculated for the compositions evaluated. In all cases, the evaluation was made with the respective compositions (either commercial toothpastes or embodiments of the invention) diluted to 50% of their nominal concentration to simulate the case of dilution with saliva or water during tooth brushing, as described elsewhere herein. Results are summarized in photographs in FIGS. 7 and 8.

Using this process we determined that:
1) This test used dual-species biofilm that was made by shaker wave method. Commercial toothpaste (CP1) removed only 35.99% of the biofilm (was NOT able to remove 64.01% of the biofilm) based on the surface area that remained covered with biofilm after cleaning. Percent biofilm removal was 35.99% for CP1.
2) This test used dual-species biofilm that was made with the flow method. Commercial toothpaste CP1 removed only 21.44% of the biofilm (was NOT able to remove 78.56% of the biofilm) based on the surface area of the HA disc.
3.) This test used dual-species biofilm that was made by shaker wave method. Commercial toothpaste (CP2) removed only 32.06% of the biofilm (was NOT able to remove 67.94% of the biofilm) based on the surface area that remained covered with biofilm after cleaning. Percent biofilm removal was 32.06% for CP2
4.) This test used dual-species biofilm that was made with the flow method. Commercial toothpaste CP1 removed only 15.45% of the biofilm (was NOT able to remove 84.46% of the biofilm) based on the surface area of the HA disc.
5) This test used dual-species biofilm that was made with the flow method. Embodiment composition (TP #75) successfully removed 98.70% of the biofilm on the HA disc. The percentage of biofilm that remained was 1.30% of the surface area).
6.) This test used dual-species biofilm that was made with the flow method. Embodiment composition TP #75 successfully removed 97.97% of the biofilm on the HA disc. The percentage of biofilm that remained was 2.03% of the surface area.

These results are summarized in Table 4; all test compositions were at 50% dilution.

TABLE 4

| Test Number | Biofilm Preparation Method | Test Composition | % biofilm Removed | % biofilm Remaining |
|---|---|---|---|---|
| 1 | Shaker | CP1 | 35.99% | 64.01% |
| 2 | Flow | CP1 | 21.44% | 78.56% |
| 3 | Shaker | CP2 | 32.06% | 67.94% |
| 4 | Flow | CP2 | 15.45% | 84.55% |
| 5 | Shaker | TP75 | 98.70% | 1.30% |
| 6 | Flow | TP75 | 97.97% | 2.03% |

The column Biofilm Preparation method indicates the method of biofilm generation, as described elsewhere in Methods. The column Composition indicates the fluid composition used to clean (after being diluted). The column % Removed indicates the fraction of the area on the surface of the HA disc that was NOT covered in biofilm after cleaning. The column % remaining indicates the fraction of the area that remained covered in biofilm after cleaning, which was the measured quantity in the test.

In general, it can be noted that for cleaning with commercial toothpaste, significant biofilm remained of the disc generally over the entire surface of the disc. For cleaning with toothpastes of embodiments of the invention, whatever small amount of biofilm remained was primarily located at the edges of the disc. Biofilm removal was about 98% with embodiment compositions at 50% dilution (Table 4)

Example 4: Head-to-Head Comparison by Taking Commercial Toothpaste and Adding MFC This example shows that pressure drop alone, or corresponding average wall shear stress generated during flow, is not a sole determining measure of cleaning effectiveness for removing biofilm from surfaces. This Example used Buildup biofilm (BBF) that was grown on Teflon tubes as described in Methods.

In this example, we show that the addition of MFC to commercial toothpaste compositions will improve BBF biofilm removal effectiveness of the commercial composition. Three different brands of popular commercial toothpaste were tested: CP1, CP2, and CP3.

It can be noted that these various commercial toothpastes comprised a variety of ingredients including: SLS, sodium lauroyl sarcosinate, Polysorbate 80 (Tween 80), sodium gluconate, CAPB, SMCT, zinc citrate, Na5P3O10, Na2HPO4, NaOH, NaHCO$_3$, stannous chloride, carrageenan, xanthan gum, cellulose gum, glycerin, carbomer (PAA polyacrylic acid), PEG-8, hydrated silica, TiO2, Mica, sorbitol, sodium saccharin, and sucralose. A typical toothpaste can comprise approximately 10 to 12 of these ingredients in addition to water.

The experimental procedure for evaluating the effectiveness of the cleaning composition was to dilute it with water to 50% of full strength (thus replicating a representative concentration in the mouth during brushing). This mixture was then pumped by a syringe pump through tubes of 3.7 mm inside dimeter. The PTFE test section containing the challenge BBF was 2 inch in length and was positioned between two flanking tubing segments each of 1 foot length. The flow rate of the diluted composition was 20 m % min for a period of 2 minutes. Pressures were measured at this flow rate at the inlet to the first flanking tubing. Cleaning was followed by a rinse with water at 90 mL/min for 1.3 minutes.

As mentioned, the compositions were made at 50% dilution with water, and the compositions that did contain MFC contained MFC concentrations of % MFC or 0.5% MFC. Thus, on an undiluted basis the concentrations of MFC in the toothpaste would have been 2% or %, respectively.

Results: We did not see any sample that might be ranked as a 3. For this series of experiments, Table 5A gives MFC content, ranking results, and pressure drop across the test section and the two 1 foot long flanking segments of tubing, and the calculated wall shear stress. A rank of is the best rank while a rank of 4 is the worst. The visual appearances of illustrative cleaned test sections and their rankings are shown in FIG. 3.

TABLE 5A

| Composition | % MFC* | Rank | Pressure, psi | Estimated Wall Shear Stress, Pa |
|---|---|---|---|---|
| CP2(50% diluted) modified by having MFC added to it | 1.0 | 1 | 11.5 | 130 |
| CP3(50% diluted) modified by having MFC added to it | 1.0 | 1 | 12.5 | 141 |
| CP1 | 0.0 | 2 | 1.7 | 19 |
| CP2(50% diluted) modified by having MFC added to it | 0.5 | 2 | 4.9 | 55 |
| CP1(50% diluted) modified by having MFC added to it | 1.0 | 4 | 12.0 | 136 |
| CP2(50% diluted) modified by having MFC added to it | 0.0 | 4 | 4.5 | 51 |

*MFC concentration is on a diluted basis.

A typical commercial toothpaste representing prior art (CP2, see Example 2) was studied "as is" (i.e., with 0% MFC added) and compared with compositions having three concentrations of MFC: 0, 0.5 and 1.0%. In the first three instances of this example, see Table 5B, the commercial toothpaste, CP2, was diluted to 50%. This diluted composition is typically used to simulate the effectiveness of the compositions after saliva dilution as normally happens during brushing. MFC in weight percent was added to the 50% concentration CP2 base and then mixed to produce a uniform mixture. In the fourth row of the Table 5B, another commercial toothpaste, CP4, was diluted only by 25% (resulting in 75% CP4 and 25% water) with no added MFC. The results are shown in Table 5B:

TABLE 5B

| Toothpaste Composition | % MFC* | Rank | Pressure, psi | Estimated Wall Shear Stress, Pa |
|---|---|---|---|---|
| CP2 (50% dilution) + MFC | 1.0 | 1 | 11.5 | 130 |
| CP2 (50% dilution) + MFC | 0.5 | 2 | 4.9 | 55 |
| CP2 (50% dilution) | 0.0 | 4 | 4.5 | 51 |
| CP4 (25% dilution) | 0.0 | 4 | 16.0 | 181 |

*MFC concentration is on a diluted basis.

It is concluded that the addition MFC to a known commercial toothpaste improves the cleaning effectiveness of that commercial toothpaste. In this, MFC or other network-forming ingredient is an important component of the inventive composition. It should be noted that all MFC-containing compositions included in Table 5A and in Table 5B are embodiment compositions and are used here to demonstrate role of the fibrillated or network forming material in removing biofilms compared to prior art commercial compositions.

Calculation of the wall shear stress is described elsewhere herein. This data shows that although an increase in the wall shear stress can be helpful, it is not the sole factor in achieving high cleaning effectiveness. We note the high wall shear stress generated by the 75% CP4 (25% dilution) mixture but its poor rank. This relatively 'thick' composition gave a high pressure drop and correspondingly high wall shear stress but was unable to produce effective removal of the biofilm. This shows that simply generating a high shear stress at the wall surface is not necessarily sufficient to remove biofilm. It is believed that the combination of the unique properties of MFC, its high surface area, and its fibril structure enabling it to reach fine crevices, combine to produce an effective cleaning agent/composition.

Example 5: Use of Humectants

This example provides embodiment compositions made with different humectants. Variation is achieved by adjusting the type and concentration of humectants within the composition. Water activity is measured as the relative humidity at equilibrium in a closed vessel equipped with a recirculating fan, and is considered an important property of toothpastes to prevent dryness and bacterial growth. Table 6 shows that compositions with different water activity levels can be made by adjusting the type and concentration of humectants within the composition, and that other ingredient normally does not affect water activity. These results show that using glycerol, propylene glycol, sorbitol or their mixtures can provide water activity as low as 0.70. Other compositions that include glycerol with either propylene glycol, sorbitol, PEG, xylitol or erythritol or with mixture of propylene glycol with either glycerol, sorbitol, PEG, xylitol or erythritol, were also made and showed that the desired toothpaste water activity between 0.70 and 0.75 can be achieved. This Example shows that humectant-water carrier liquid can be used to make embodiment compositions at any desired water activity without limitation. The invention is not meant to be limited to the type of humectant or the mixture used to make the composition. In addition, compositions made with water are useful when preservatives are included.

TABLE 6

|  | TP 20 | TP 22 | TP 28 | TP 41 |
|---|---|---|---|---|
| Microfibrillated cellulose (MFC) | 1.5 | 1.5 | 2.0 | 1.75 |
| Microcrystalline cellulose (MCC) | 1.5 | 1.5 | 1.5 | 2.5 |
| Super Absorbent Polymer (SAP) SCL | 0.5 | 0 | 0 | 0.5 |
| Titanium dioxide | 0.22 | 0 | 0 | 0.22 |
| Hydrated silica abrasive | 19.0 | 19.0 | 19.0 | 19.0 |
| Hydrated silica thickener | 4.0 | 2.0 | 0 | 2.0 |
| 1,2 Propanediol | 24.0 | 0 | 40 | 45.0 |
| Glycerin | 5.0 | 45.0 | 0 | 0 |
| Baking Soda | 0 | 0 | 0 | 0 |
| Sorbitol (70%) | 15.0 | 0 | 0 | 0 |
| Water from Sorbitol | 4.5 | 0 | 0 | 0 |
| Water | 27.387 | 31.0 | 37.50 | 27.137 |
| Water Activity (Wa) | 0.78 | 0.70 | 0.75 | 0.71 |

Example 6 Minimal Composition, with MFC Alone (No Particles Included), is Able to Clean A relatively simple embodiment composition (Table 7A) comprising MFC, glycerin, surfactant and water was found to effectively remove BBF (representing plaque biofilm) with a Cleaning Rank of 1. In this composition, the viscosity and rheology are determined mainly by the MFC or fibrillated material. This composition lacks the presence of MCC, abrasive silica and thickening silica and polymeric thickeners. Nevertheless, it could still thoroughly remove the BBF. This indicated that the fibrillated network formed due to MFC can effectively function to provide the necessary attributes to remove the biofilm. This demonstrates that MFC is the key ingredient for the plaque removal performance and that, if needed, MFC can function as a toothpaste thickener instead of inorganic thickener such as silica or organic thickeners which are typically used as thickening agents in prior art commercial toothpastes.

As a control, we show that there is no biofilm removal when a composition does not contain MFC, even when adding a high load of silica and MCC.

TABLE 7A

|  | TP 67 Concentration (%) |
|---|---|
| Sodium lauryl sulfate (SLS) | 1.0 |
| Microfibrillated cellulose (MFC) | 5.0 |
| Microcrystalline cellulose (MCC) | 0.0 |
| Super Absorbent Polymer (SAP) | 0.0 |
| Titanium dioxide | 0.22 |
| Hydrated silica abrasive | 0.0 |
| Hydrated silica thickener | 0.0 |
| Glycerin | 35 |
| Water | 58.780 |
| ΔP (psi) | 13.40 |
| Cleaning Rank | 1 |

In contrast, a similar composition (Table 7B) containing no MFC (even though it did contain MCC and abrasive) did not clean at all (Cleaning Rank 4).

TABLE 7B

| EXAMPLE: TP with No MFC | |
|---|---|
|  | TP 68 |
| Sodium lauryl sulfate (SLS) | 1.0 |
| Microfibrillated cellulose (MFC) | 0.0 |
| Microcrystalline cellulose (MCC) | 4.0 |
| Super Absorbent Polymer (SAP) | 0.0 |
| Titanium dioxide | 0.22 |
| Hydrated silica abrasive | 25.0 |
| Hydrated silica thickener | 5.0 |
| Glycerin | 40 |
| Water | 24.780 |
| Cleaning Rank | 4 |

Example 7: Effect of MCC

We prepared toothpaste formulations comprising various different concentrations and types of microcrystalline cellulose, and showed that successful biofilm removing formulations (cleaning ranking 2) can be achieved with microcrystalline cellulose particles of various different sizes and types, such as 50 microns silicified microcrystalline cellulose (SMCC 50) or microcrystalline cellulose with particle size 200 microns (PH200) or mixtures of them. The concentration of the MCC or SMCC can be adjusted from about 1% to 5% to help in tailoring rheological properties and cleaning performance. In addition, this example also demonstrates that successful biofilm cleaning formulations can be formulated, in case they are needed, within a broad range of thickening silica (0 to 5%) or abrasive silica (10-25%). (MCC was obtained as Avicel PH200, from DuPont Nutrition USA, Inc. (part of DOW), Wilmington, DE. SMCC was obtained from JRS Pharma LP, Patterson, NY. NatrosolT 250HR CS was obtained from Ashland Chemicals, Wilmington, DE.) Note that the number 50 or 200 in the product designation indicates mean particle size in microns. the results are summarized in Table 8. MCC is helpful but there may also be other ways of achieving good cleaning.

TABLE 8

|  | TP 72 | TP 74 | TP 75 | TP 76 | TP 77 |
|---|---|---|---|---|---|
| Microfibrillated cellulose (MFC) | 2.2 | 1.75 | 1.75 | 1.75 | 1.75 |
| Microcrystalline cellulose (MCC) | 2.5 | 2.5 | 4.0 | 5.0 | 5.0 |

TABLE 8-continued

|  | TP 72 | TP 74 | TP 75 | TP 76 | TP 77 |
|---|---|---|---|---|---|
| Titanium dioxide | 0.22 | 0.22 | 0.22 | 0.22 | 0.22 |
| Hydrated silica abrasive | 10.0 | 19.0 | 5.0 | 10.0 | 10.0 |
| Hydrated silica thickener | 0.5 | 2.0 | 0 | 0 | 0 |
| Glycerin | 40.0 | 35 | 35 | 40 | 40 |
| Water | 44.580 | 39.530 | 54.030 | 43.030 | 43.030 |
| ΔP | 5.8 | 5.4 | 8.8 | 3.9 | 3.9 |
| Rank | 2 | 2 | 2 | 2 | 2 |
| MCC Type | * SMCC 50 | * PH 200 | * PH 200 | * 50/50; SMCC50/ PH 200 | * PH 200 |

Example 8: Effect of Polymeric Thickeners

We prepared MFC-based toothpaste formulations with various polymeric thickeners and showed that good bacterial biofilm cleaning performance can be achieved when formulating the toothpaste with hydroxyethylcellulose (HEC, Natrosol 250HR CS), xanthan gum or Carbopol 918. This shows that there is a broad range of polymeric thickeners concentration and type, or mixture of thereof, from which to select to meet any specific requirement of rheological and cleaning performance. Moreover, these formulations can be realized within a broad range of MCC (from 0 to 5%), a broad range of thickening silica concentration (from 0 to 5%) and with a broad range of abrasive silica concentration (10 to 25%). This, along with other Examples, shows that it is possible to make a composition without polymeric thickeners that can still clean. The compositions and cleaning rankings are shown in Table 9.

TABLE 9

|  | TP 49 | TP 54 | TP 55 |
|---|---|---|---|
| Microfibrillated cellulose (MFC) | 1.75 | 1.20 | 1.20 |
| Microcrystalline cellulose (MCC) | 2.5 | 2.5 | 2.5 |
| Titanium dioxide | 0.22 | 0.22 | 0.22 |
| Hydrated silica abrasive | 19.0 | 15.0 | 15.0 |
| Hydrated silica thickener | 2.0 | 0.5 | 0.5 |
| Glycerin | 35 | 35 | 35 |
| Hydroxyethyl cellulose (HEC) (Natrosol 250 HR CS | 0.50 | 0.50 | 0 |
| Carboxymethyl cellulose (CMC) | 0 | 0 | 0 |
| Xanthan Gum | 0 | 0 | 0.50 |
| Carbopol | 0 | 0 | 0 |
| Carrageenan | 0 | 0 | 0 |

TABLE 9-continued

|  | TP 49 | TP 54 | TP 55 |
|---|---|---|---|
| Water | 36.537 | 42.587 | 42.587 |
| Rank | 2 | 3 | 3 |

Example 9: Effect of SAP

Embodiment compositions comprise SAPs. In this Example, we prepared compositions with different types of SAPs. Particulate SAPs are included in embodiment compositions to tailor their rheology, retard effect of saliva-induced dilution of the paste, enhance the removal of plaque biofilm among other functions as described elsewhere herein. Two main types of SAP were used and found to provide successful compositions in terms of biofilm removal: i) a surface cross-linked SAP (example: 0-60 SCL obtained from Zappa Stewart (Westwood, MA); particle size 2 μm to 104 μm or larger); this is in the form of plate-like particles that remain as discrete particles which do not coalesce/merge into each other when exposed to water and ii) not-surface cross-linked one (example: Aqua Keep 10SH-NFC made by Sumitomo Seika, Tokyo, Japan; particle size 20-30 microns) where the particles formed in water can at least partially merge together. Similarly, Carbopol may be used as an SAP despite their small particle size (about 1-10 μm). SAP-containing embodiment compositions can be made at a broad range of concentrations of (0 to 5%) and at a broad range of the other components, for example: MFC (0 to 5%), MCC (0 to 5%), abrasive silica (10 to 25%), thickening silica (0 to 5%) and polymeric thickeners (0 to 5%). Table 10 provides example compositions made with different SAP types and concentrations.

We prepared MFC-based toothpaste formulations with different types and contents of super absorbent polymers (SAP). SAP can be used as an organic thickener within our toothpaste and/or as a bacterial biofilm cleaning adjuvant. Two main types of SAP were used and found to provide successful toothpaste formulations in terms of bacterial biofilm removal: i) a surface cross-linked SAP (Zappa Stewart 0-60 SCL), that forms plate-like particles in water that do not merge/compenetrate into each other and ii) non-surface cross-linked SAP (Aquakeep 10SH-NFC) in which the particles formed in water can at least partially compenetrate each other, similarly to solutions of Carbopol in water. These toothpastes can be formulated within a broad range of concentration of SAP (0 to 5%) and within a broad range of the other compounds examines, such as MFC, MCC (0 to 5%), abrasive silica (10 to 25%), thickening silica (0 to 5%) and polymeric thickeners (0 to 5%).

The compositions and cleaning rankings are shown in Table 10. A representative micrograph is shown in FIG. 1C.

TABLE 10

|  | TP 17 | TP 18 | TP 31 | TP 37 | TP 59 | TP 60 |
|---|---|---|---|---|---|---|
| Sodium lauryl sulfate (SLS) | 0.7 | 1.0 | 1.0 | 1.0 | 1.0 | 1.0 |
| Microfibrillated cellulose (MFC) | 1.5 | 1.5 | 1.5 | 1.5 | 1.3 | 1.3 |
| Microcrystalline cellulose (MCC) | 1.5 | 1.5 | 1.5 | 3.0 | 2.0 | 2.0 |
| Super Absorbent Polymer (SAP) | 0.5 | 0.5 | 0.5 | 1.0 | 0.50 | 0.50 |
| Titanium dioxide | 0 | 0 | 0.22 | 0.22 | 0.22 | 0.22 |
| Hydrated silica abrasive | 19.0 | 19.0 | 19.0 | 19.0 | 15.0 | 15.0 |
| Hydrated silica thickener | 4.0 | 4.0 | 0 | 0 | 0 | 0 |
| 1,2 Propanediol | 24.0 | 24.0 | 45.0 | 45.0 | 0.00 | 0.00 |
| Glycerin | 5.0 | 5.0 | 0 | 0 | 35.0 | 35.0 |
| Sorbitol (70%) | 15.0 | 15.0 | 0 | 0 | 0 | 0 |
| Water from Sorbitol | 4.5 | 4.5 | 0 | 0 | 0 | 0 |
| Sodium phosphate monobasic | 0 | 0 | 0 | 0 | 0.25 | 0.25 |
| Sodium phosphate dibasic | 0 | 0 | 0 | 0 | 0.25 | 0.25 |
| Potassium sorbate | 0 | 0 | 0 | 0 | 0.10 | 0.10 |

TABLE 10-continued

|  | TP 17 | TP 18 | TP 31 | TP 37 | TP 59 | TP 60 |
|---|---|---|---|---|---|---|
| Hydroxyethyl cellulose (HEC) | 0 | 0 | 0 | 0 | 0.25 | 0.25 |
| Water | 28.8 | 28.5 | 30.887 | 29.387 | 44.130 | 44.130 |
| Rank | 2 | 2 | 1 | 1 | 1 | 1 |
| SAP type | SCL | SCL | SCL | SCL | Not SCL | SCL |

Example 10: Incorporation of Abrasives in the Microstructural Network of the Embodiment Composition The incorporation of abrasives in the fibrillated microstructure was found to significantly strengthen the mechanical properties of the resulting material. FIG. 9 shows a significant increase in G' and G" by about a factor 6 when the abrasive silica (Zeodent 113) was increased from 5% and 19% in a suspension/paste of 1.5% MFC by weight in water. It is believed that the incorporation of abrasives in the inventive composition may enhance the effectiveness in removing plaque biofilm and stain as detailed elsewhere herein.

It is known (Lewis, R., Dwyer-Joyce, R. S., & Pickles, M. J. (2004). Interaction between toothbrushes and toothpaste abrasive particles in simulated tooth cleaning. Wear, 257(3-4), 368-376) that the mechanism by which abrasive particles remove stain is by entrapment and dragging/friction of the particle between the toothbrush bristles and the surface of the teeth where the stain is located, while abrasive particles that do not get trapped underneath the bristles and are dispersed in solution and do not contribute any stain removal. In this regard, we hypothesize that the MFC fibers/fibrils act as another possible factor in trapping the abrasive particles and dragging them over the stain thus improving the stain removal.

Example 11: Effect of the Humectants on Mechanical and Microstructural Properties of the Formulations We note that there are significant effects on the microstructure and mechanical properties of the toothpaste according to the liquid carrier that is used. Indeed, there is a significant increase in viscosity and elasticity when using a humectant or a mixture of humectant and water as compared to the use of water alone. The combined use of humectant and water contributes an increase in the mechanical properties of the paste possibly due to the formation of more extended microstructural network without the formation of solvent pockets/voids, which are likely to occur when using only water as a solvent.

It is observed that there is significant difference between compositions made with a mostly-water carrier liquid and those made with a mostly-humectant carrier liquid. There are differences in the microscopic appearance, in the Water Activity Coefficient, and in the rheology of the compositions.

Figure 10:
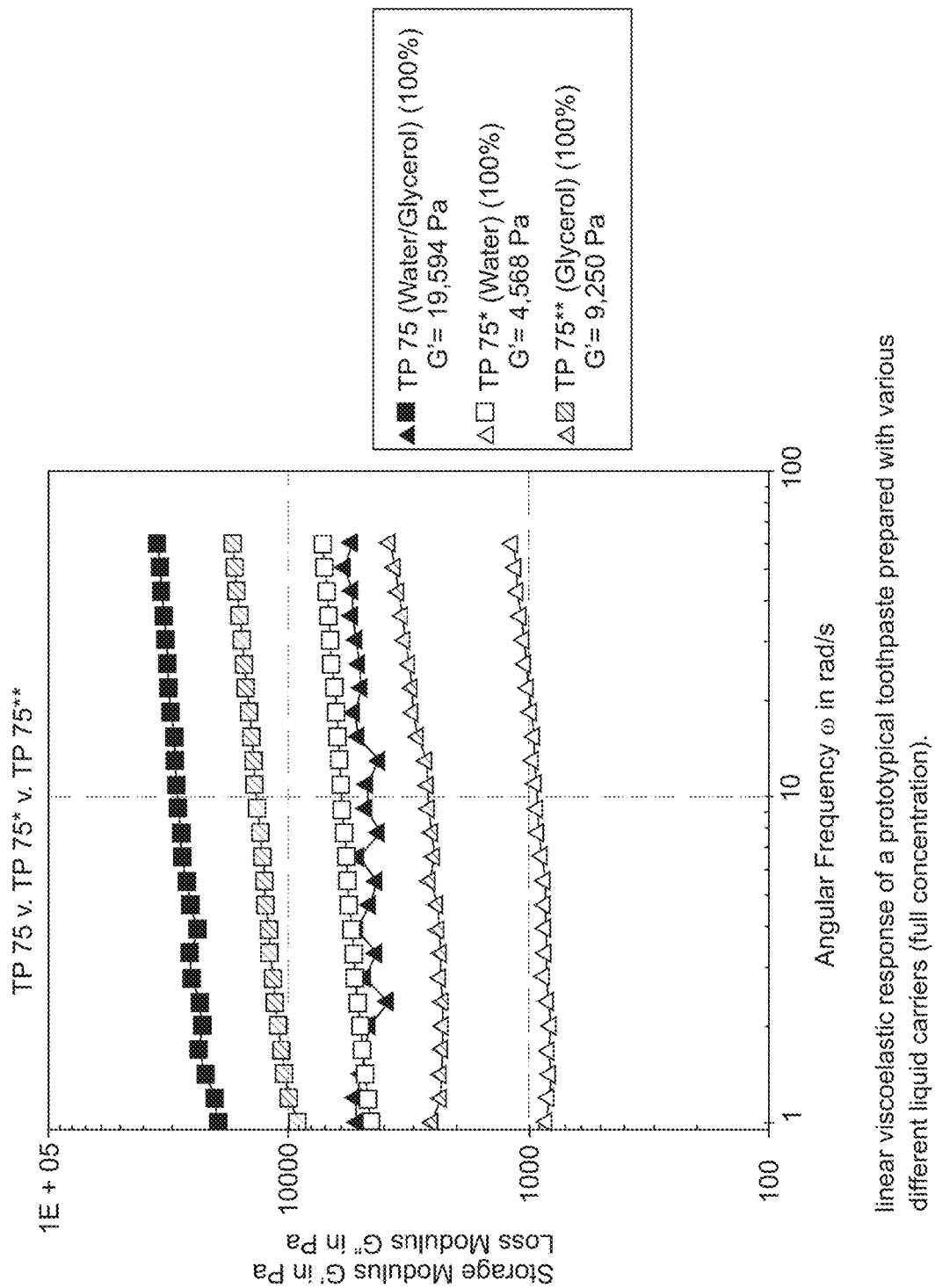
FIG. 10 shows the linear viscoelastic response of a prototypical toothpaste prepared with various different liquid carriers (full concentration).
Figure 11:
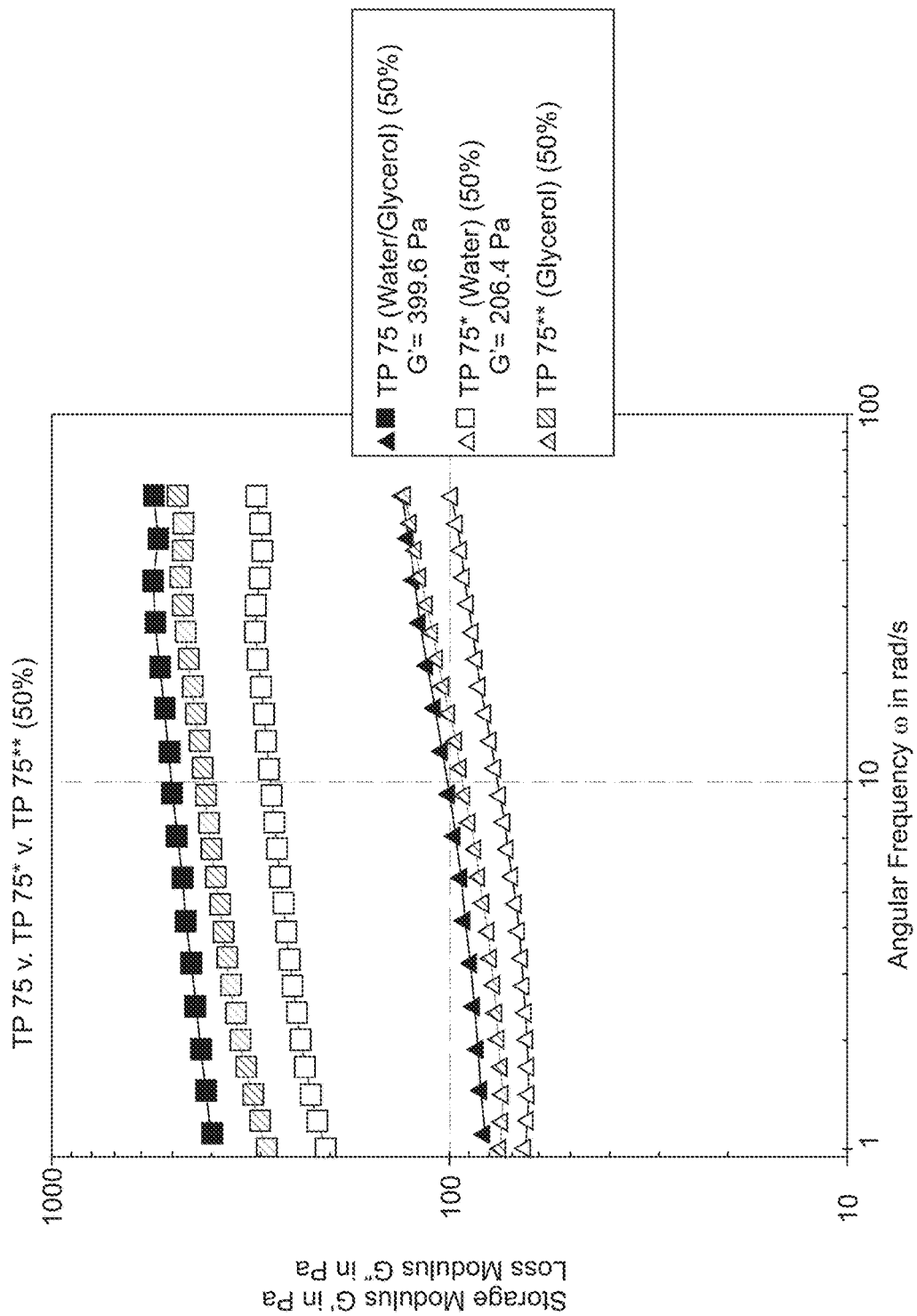
FIG. 11 shows the linear viscoelastic response of a prototypical toothpaste prepared with different liquid carriers (dilution 50%).

In FIG. 10 we report the storage (G') and viscous modulus (G") of three prototypical toothpastes prepared with either water alone as a solvent or mixtures of water and glycerol. The weakening of mechanical properties created by water dilution of the paste is less pronounced when using a humectant in combination with water as compared to water alone, as highlighted. In FIG. 11 we report the linear viscoelastic response of the toothpaste, made with three different carrier liquids, after being diluted with water to a 50% concentration of the original composition. In other words, the storage and viscous modulus of the paste at 50% dilution with water are larger when using a humectant as a liquid carrier as compared to water alone as a liquid carrier. We note that the water dilution is useful to mimic the change in mechanical properties of the paste when it comes in contact with saliva in the mouth.

Table 11 shows the compositions used.

TABLE 11

|  | TP 75 | TP 75* | TP 75** |
|---|---|---|---|
| Sodium saccharin | 0.3 | 0.3 | 0.3 |
| Sucralose | 0.05 | 0.05 | 0.05 |
| Sodium fluoride | 0.243 | 0.243 | 0.243 |
| Sodium lauryl sulfate (SLS) | 1.0 | 1.0 | 1.0 |
| Peppermint flavor | 0.3 | 0.3 | 0.3 |
| Microfibrillated cellulose (MFC) | 1.75 | 1.75 | 1.75 |
| Microcrystalline cellulose (MCC) | 4.0 | 4.0 | 4.0 |
| Titanium dioxide | 0.22 | 0.22 | 0.22 |
| Hydrated silica abrasive | 5.0 | 5.0 | 5.0 |
| Hydrated silica thickener | 0.0 | 0.0 | 0.0 |
| Glycerin | 35 | 0 | 70.787 |
| Sodium phosphate monobasic | 0.25 | 0.25 | 0.25 |
| Sodium phosphate dibasic | 0.25 | 0.25 | 0.25 |
| Potassium sorbate | 0.10 | 0.10 | 0.10 |
| Water | 51.537 | 86.537 | 15.750 |

Example 12: Rheology Ranges of Composition for Toothpaste, Prophylaxis Paste Etc

|  | TP 46 | TP 75 |
|---|---|---|
| Sodium saccharin | 0.3 | 0.3 |
| Sucralose | 0.05 | 0.05 |
| Sodium fluoride | 0.243 | 0.243 |
| Sodium lauryl sulfate (SLS) | 1.0 | 1.0 |
| Peppermint flavor | 0.3 | 0.3 |
| Microfibrillated cellulose (MFC) | 1.75 | 1.75 |
| Microcrystalline cellulose (MCC) | 2.5 | 4.0 |
| Titanium dioxide | 0.22 | 0.22 |
| Hydrated silica abrasive | 19.0 | 5.0 |
| Hydrated silica thickener | 2.0 | 0.0 |
| Glycerin | 35 | 40 |
| Sodium phosphate monobasic | 0.25 | 0.25 |
| Sodium phosphate dibasic | 0.25 | 0.25 |
| Potassium sorbate | 0.10 | 0.10 |
| Distilled water | 37.037 | 46.537 |

This example shows that embodiment compositions can be made to cover a wide range of rheological properties from a paste resembling a prophylaxis paste (TP46) to a toothpaste formulation (TP75). This Example also shows the effect of water-induced dilution on the rheological properties of the compositions. We used water to mimic the effect of saliva-induced dilution on the mechanical properties of the toothpaste.

Figure 12A:
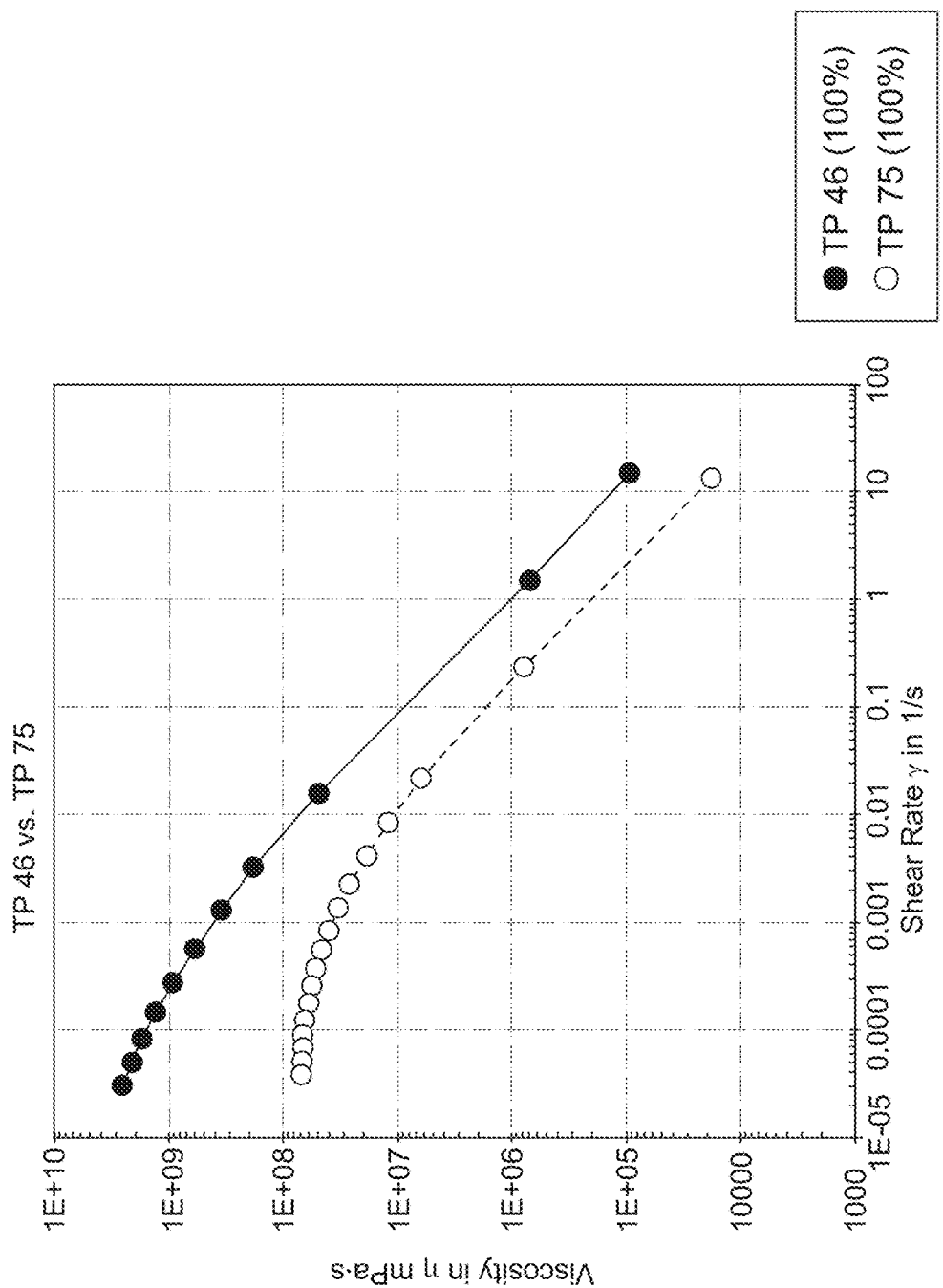
FIG. 12A shows viscosity as a function of shear rate for two embodiments of the invention.

Viscosity as a function of the shear rate for TP46 and TP75 at 100% composition is provided in FIG. 12A. For TP46, the viscosity at the lower shear rates is about 2 orders of magnitude larger than that of TP75, while at the higher shear rates there is about one order of magnitude of difference between the viscosity of the two formulations.

Figure 12B:
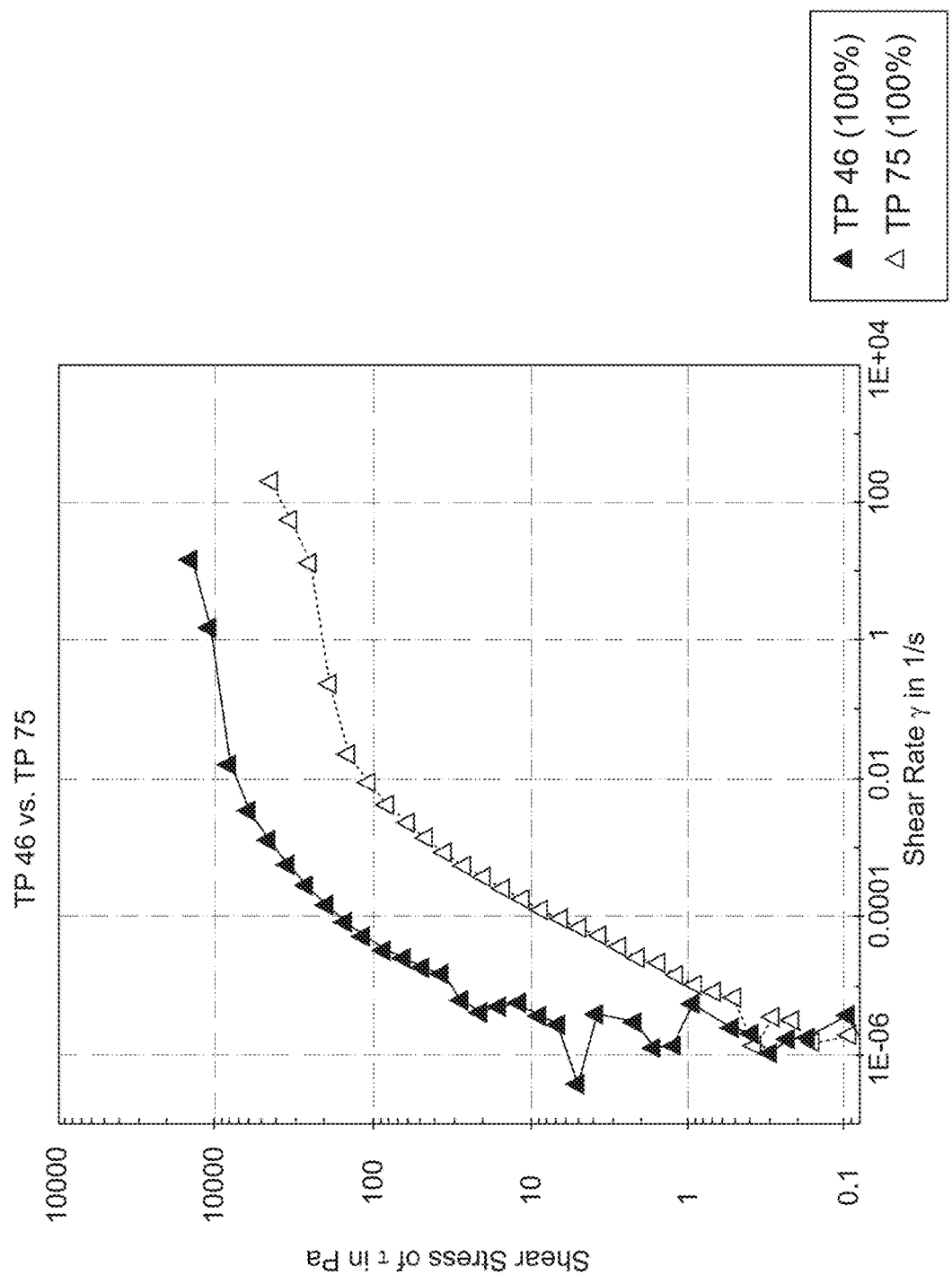
FIG. 12B shows shear stress a function of shear rate for two embodiments of the invention.
Figure 12C:
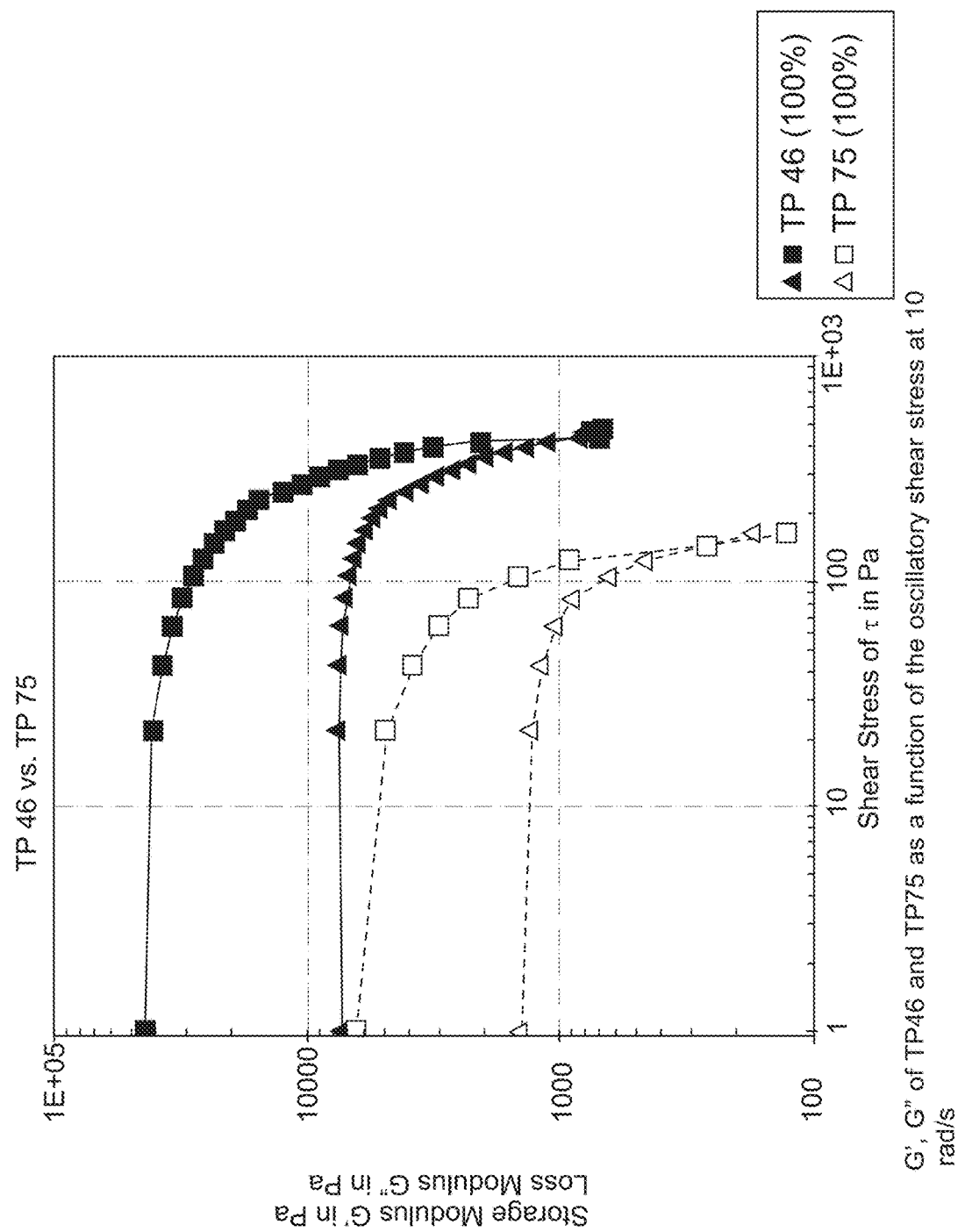
FIG. 12C shows G', G" as a function of the oscillatory shear stress for two embodiments of the invention.
Figure 12D:
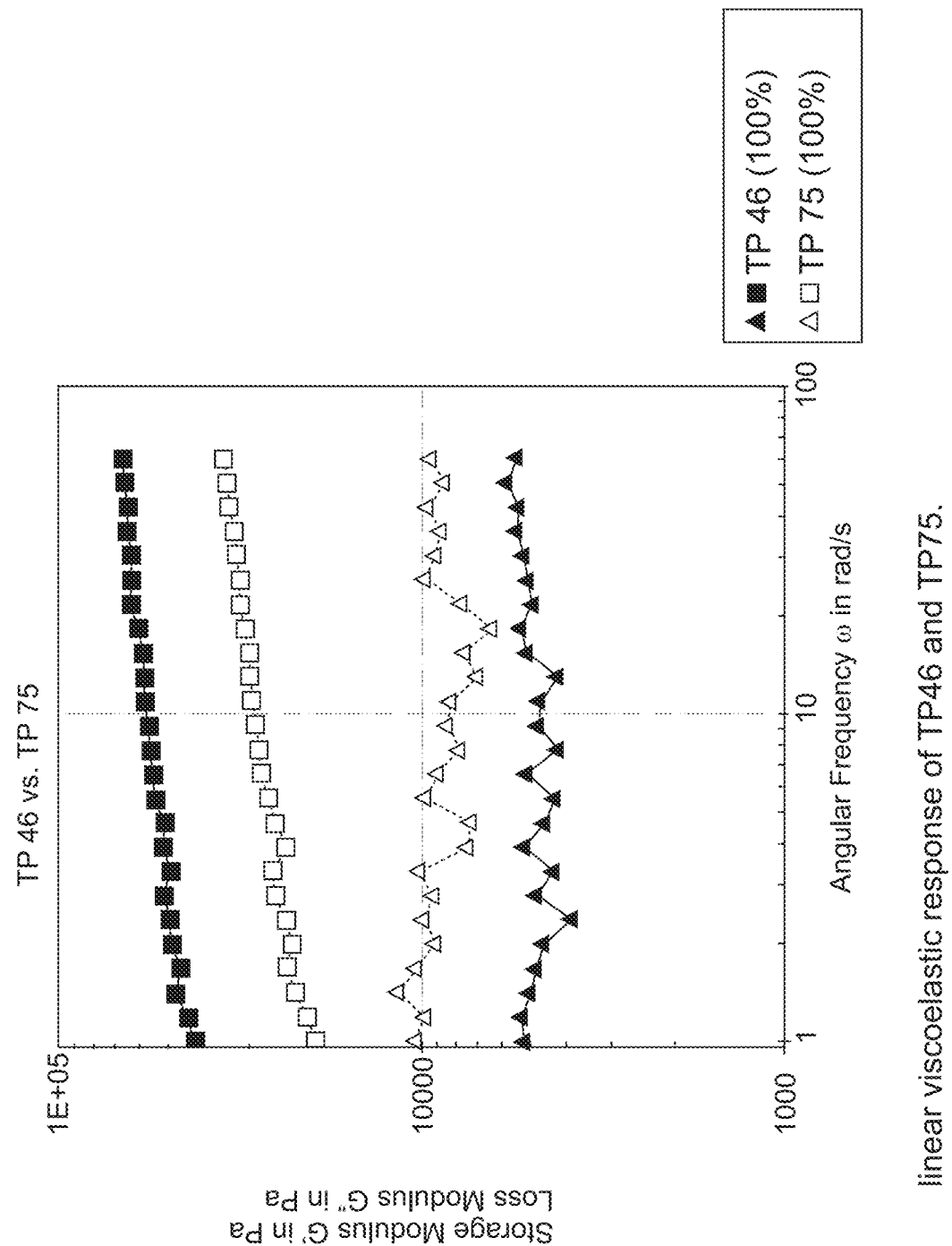
FIG. 12D shows G', G" as a function of angular frequency for two embodiments of the invention.

FIG. 12B displays the shear stress as a function of the shear rate for the two compositions at 100% concentrations. Here, the yield shear stress of TP46 is about 500 Pa while that of TP75 is about 100 Pa. Here, the yield stress is defined as the minimum stress by which the shear rates start to be significantly different from zero. This rheological behavior is a characteristic of the inventive compositions where there is a nearly constant shear stress (between 100 and 1000 Pa) within a shear rate range of 1 to about 100 s$^{-1}$. This suggests that the microstructure of such compositions does not break down in this shear rate range which is relevant to tooth brushing. The yield stress values of the TP46 and TP75 were also confirmed by oscillatory shear tests performed at a fixed angular frequency of deformation of 10 rad/s varying the oscillatory shear stress. In the latter, the stress at which G' crosses G" can be identified as the yield stress (FIG. 12C). FIG. 12D displays the linear viscoelastic response of the two compositions at 100% concentration (no dilution). TP46 has a storage modulus of about 50,000 Pa whereas TP75 has a storage modulus of about 20,000 Pa.

Figure 12E:
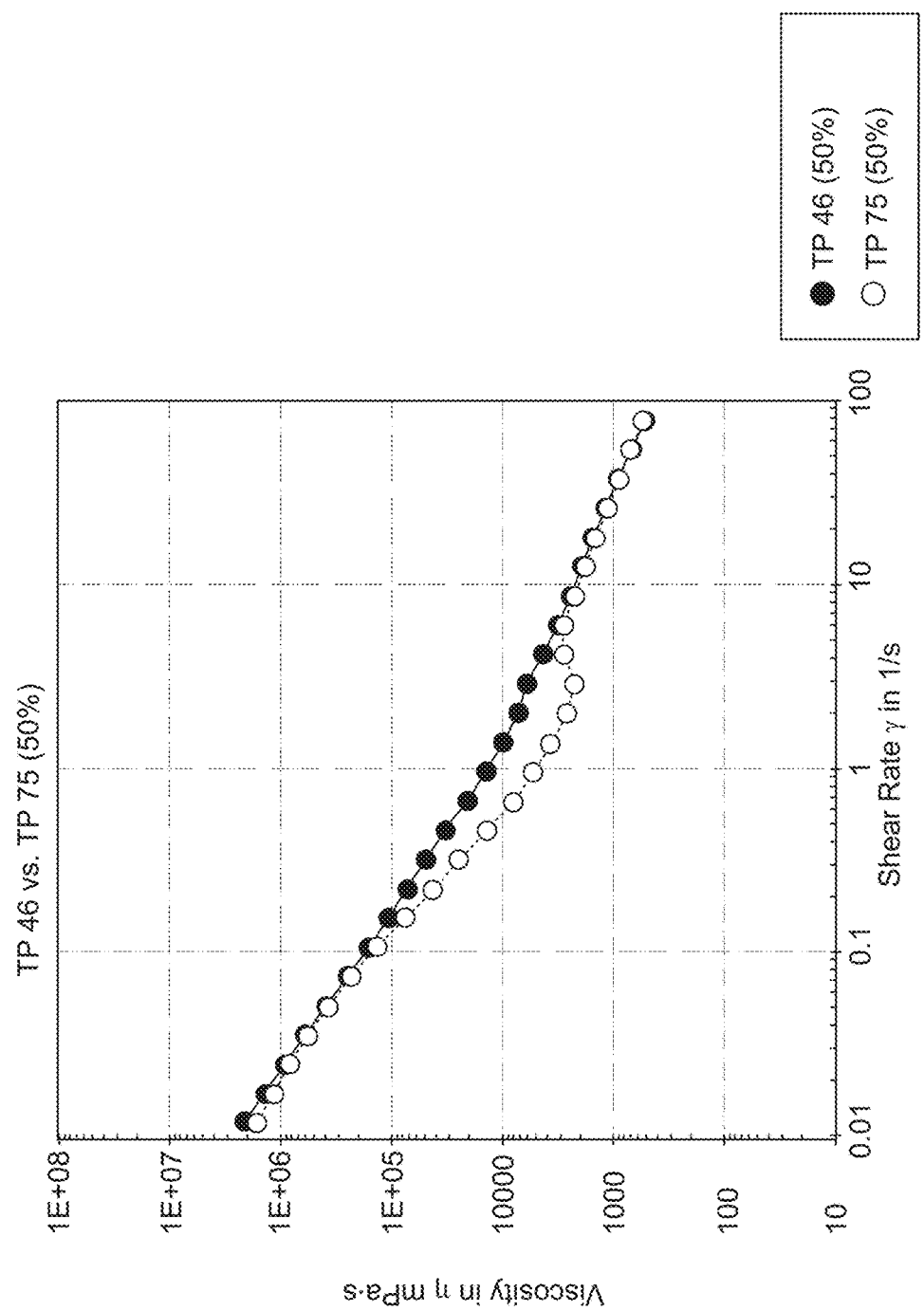
FIG. 12E shows viscosity as a function of shear rate for two embodiments of the invention diluted 50% with water.

FIG. 12E shows the viscosity as a function of the shear rate of the two compositions after dilution with water to 50% concentration. TP46 and TP75 have a comparable viscosity values over all the shear rate range investigated.

Figure 12F:
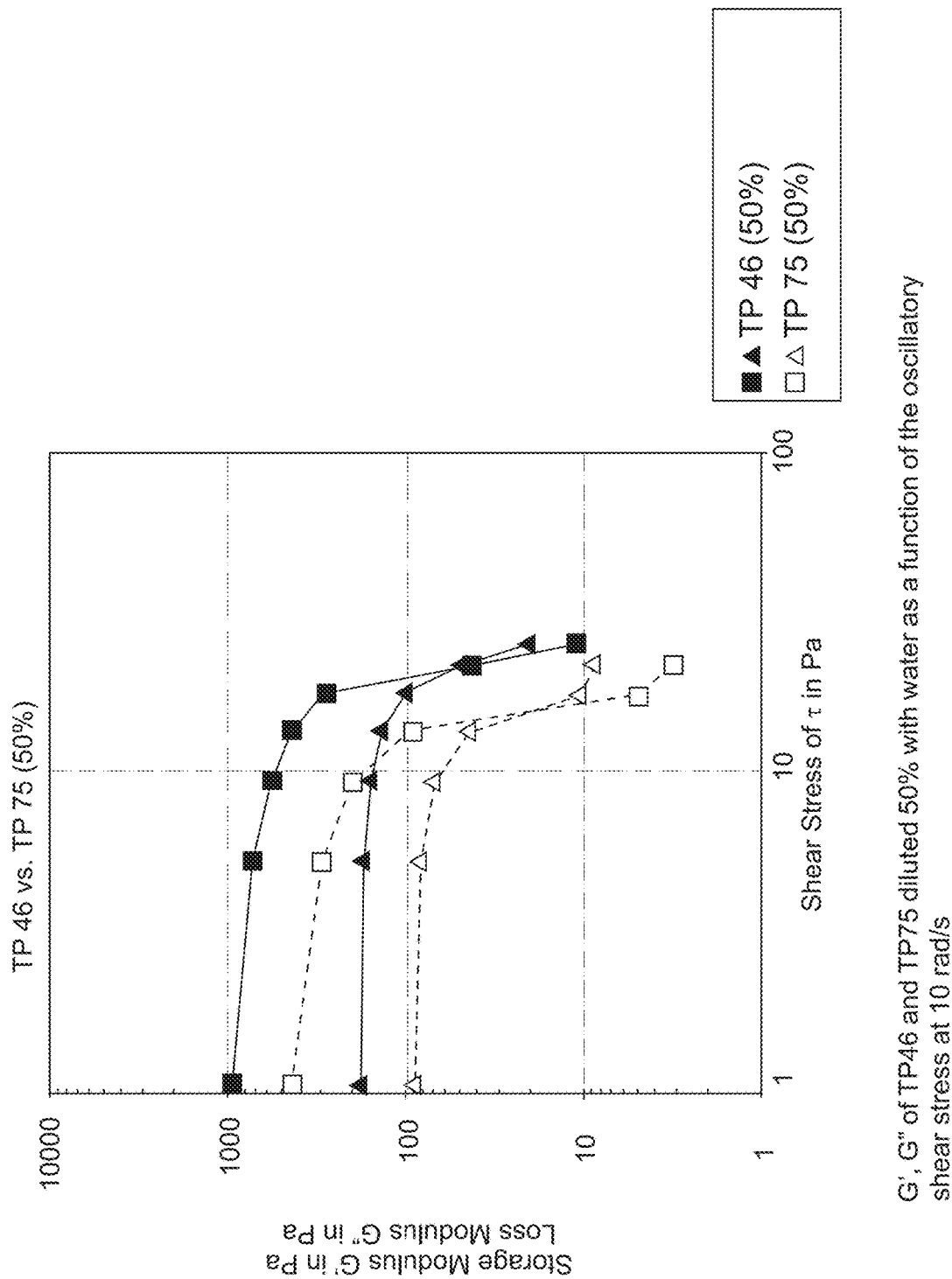
FIG. 12F shows G', G" as a function of the oscillatory shear stress for two embodiments of the invention diluted 50% with water.

FIG. 12F indicates that the yield stress of TP46 diluted at 50% with water is about twice (30 Pa) that of TP75 (15 Pa). We note that the yield stress is determined by the stress at which G' crosses G". These results support that the embodiment compositions preserve a gel-like rheometric response (G'>>G") upon dilution and suggest that even at 50% dilution the MFC network is only weakened but is not broken down. This Example clearly demonstrates that the rheological properties of the inventive compositions can be tailored by adjusting the ingredients concentrations, and in this respect the invention may not be limited to the ranges disclosed herein.

This shows, among other things, that we can formulate a broad range of mechanical parameters of the compositions of embodiments of the invention.

Further Remarks

In the work for this patent application, beyond the work in U.S. Ser. No. 17/062,424 and PCT/US2020/054149, we increased humectant concentration, sometimes to as much as 80% concentration. It is observed that, compared to a water-dominated carrier liquid, a high-humectant carrier liquid produces a fiber morphology that is more favorable to creating entangled networks, without leaving MFC-depleted pockets/voids within the microstructure of the material, which is favorable for removing plaque biofilm and other matter. Improved removal of plaque biofilm is demonstrated. We disclose compositions containing "thirsty" SAP. Embodiment compositions significantly improve removal of plaque biofilm.

It is believed that because of the more effective cleaning provided by embodiments of the invention, the fluoride in toothpastes and related products may more effectively reach the dentin and enamel of teeth, with beneficial effect.

In general, any combination of disclosed features, components, methods and steps described herein, that is physically possible, is intended to be within the scope of the claims.

All cited references are incorporated by reference herein.

Although embodiments have been disclosed, it is not desired to be limited thereby. Rather, the scope should be determined only by the appended claims.

We claim:

1. An oral hygiene composition comprising:
a mixture of: (i) a carrier liquid; and (ii) water-insoluble hydratable polymer fibers forming an entangled three-dimensional network of said water-insoluble hydratable polymer a fibers in said carrier liquid; wherein:
said carrier liquid comprises water and at least one of glycerol, sorbitol, or a mixture of glycerol and sorbitol, wherein the at least one of glycerol, sorbitol, or a mixture of glycerol and sorbitol is present in excess of 20 wt. % based on the weight of the composition;
said composition has an elastic modulus G' and a loss modulus G", and said elastic modulus G' is larger that said loss modulus G"; and
said water-insoluble hydratable polymer fibers have a diameter of about 10 to about 20,000 nm and a length of at least 100 nm.

2. An oral hygiene composition according to claim 1 wherein:
said water-insoluble hydratable polymer fibers comprise polymers having cellulosic groups, saccharide groups, or both cellulosic groups and saccharide groups.

3. An oral hygiene composition according to claim 1 wherein:
said water-insoluble hydratable polymer fibers are formed by fibrillation.

4. An oral hygiene composition according to claim 1 wherein:
said water-insoluble hydratable polymer fibers have an aspect ratio (length to diameter) of at least 10.

5. An oral hygiene composition according to claim 1 wherein:
said composition comprises about 0.1 wt. % to about 8 wt. % of said water-insoluble hydratable polymer fibers.

6. An oral hygiene composition according to claim 1 wherein:
said composition further comprises about 0.2 wt. % to about 5 wt. % surfactant.

7. An oral hygiene composition according to claim 1 wherein:
said composition has an entangled three-dimensional network of water-insoluble hydratable polymer fibers in said carrier liquid, and exhibits a volume percentage of regions devoid of fiber of less than 20%, wherein the regions devoid of fiber have a size of at least about 10 um.

8. An oral hygiene composition according to claim 1 wherein:
said composition has an RDA of less than 200.

9. An oral hygiene composition according to claim 1 wherein:
said water-insoluble hydratable polymer fibers are activated to increase entanglement by shear forces.

10. An oral hygiene composition according to claim 1 wherein:
said water-insoluble hydratable polymer fibers comprise thicker fibrils and thinner fibrils branched from said thicker fibrils, wherein said thicker fibrils have a diameter of about 250 nm to about 20,000 nm.

11. An oral hygiene composition according to claim 1 wherein:
said composition further comprises non-fibrillated particles that are entrapped or surrounded within said network.

12. An oral hygiene composition according to claim 1 wherein:
said composition further comprises non-fibrillated, abrasive particles present at a concentration in a range of 0.05 wt. % to 40 wt. %.

13. An oral hygiene composition according to claim 1 wherein:
said composition comprises microcrystalline cellulose, and a non-fibrillated material comprising particles comprising at least one of hydrated silica, another form of silica, calcium carbonate, or another inorganic substance.

14. An oral hygiene composition according to claim 1 wherein:
said water-insoluble hydratable polymeric fibers are present at a fiber concentration, and further comprising non-fibrillated particles that are present at a particle concentration, and wherein said particle concentration ranges up to 80 times said fiber concentration.

15. An oral hygiene composition according to claim 1 wherein:
said composition further comprises particles of one or more superabsorbent polymers.

16. An oral hygiene composition according to claim 15 wherein:
said one or more superabsorbent polymers comprising cross-linked polyacrylic acid or salts thereof, or other natural substances that are superabsorbent.

17. An oral hygiene composition according to claim 15 wherein:
said particles of one or more superabsorbent polymers are provided at a concentration of 0.1 wt. % to 5 wt. % of said composition.

18. An oral hygiene composition according to claim 15 wherein:
said particles of one or more superabsorbent polymers are surface cross-linked or bulk crosslinked or have a centrifuge retention ratio less than 50 g/g in physiological saline solution.

19. An oral hygiene composition according to claim 15 wherein:
said water is provided in the composition in an amount that is less than a possible amount of water absorption calculated as an amount of said water-insoluble hydratable polymer fibers multiplied by a Water Holding Capacity, plus an amount of said superabsorbent polymer multiplied by a Centrifuge Retention Capacity.

20. An oral hygiene composition according to claim 15 wherein:
said water is provided in an amount less than an amount of said superabsorbent polymer multiplied by a Centrifuge Retention Capacity.

21. An oral hygiene composition according to claim 1 wherein:
said water-insoluble hydratable polymer fibers have a specific surface area of at least 10 m2/g as determined by the Brunauer-Emmett-Teller method.

22. An oral hygiene composition according to claim 1 wherein:
said composition has a storage modulus of 200 Pa or higher, and a yield shear stress of about 1.0 Pa to about 2000 Pa.

23. An oral hygiene composition according to claim 1 wherein:
said composition contains less than 5% concentration of polymeric thickener, if present at all.

24. An oral hygiene composition according to claim 1, further comprising at least one additional component selected from the following:
(i) from about 0.1% to about 10% of a particulate, water-insoluble, micro-crystalline cellulose (MCC) or a particulate silicified micro-crystalline cellulose (SMCC);
(ii) from about 0.1% to about 5% of a synthetic particulate surface cross-linked or non-surface-cross-linked super absorbent polymer (SAP);
(iv) from about 0.1% to about 20% of a natural particulate, non-cross-linked super absorbent polymer (NSAP);
(v) from about 0.1% to about 10% of a water-insoluble, nano-crystalline cellulose polymer (CNC),
(vii) a natural or synthetic water-insoluble powdered cellulose (CP); and
(viii) from about 0.1% to about 8% of chitosan or its derivatives.

25. An oral hygiene composition according to claim 1, further comprising at least one of the following ingredients:
(i) about 5% to about 65% of a dental abrasive;
(ii) about 0.2% to about 2%, of a surfactant, selected from sodium lauryl sulfate, sodium lauroyl sarcosinate, cocamidopropyl betaine, sodium lauryl sulfoacetate, sodium methyl cocoyl taurate, and amine oxide;
(iii) a fluoride source, selected from sodium fluoride, sodium mono-fluorophosphate, stannous fluoride and an amine fluoride in an amount to provide about 0.025% to 1% of fluoride ions; and
(iv) about 0.5% to about 8% of an inorganic thickener.

26. An oral hygiene composition according to claim 1, further comprising at least one of the following ingredients:
(i) about 0.1% to about 2.0% of an essential oil or a flavoring agents selected from peppermint oil, spearmint oil, mixtures of mint oils, oil of wintergreen, clove oil, lime oil, lemon oil, orange oil, grapefruit oil, licorice, methyl salicylate, cinnamon, methyl cinnamate, ethyl cinnamate, butyl cinnamate, ethyl butyrate, ethyl acetate, eugenol, eucalyptol, anethole, carvone, menthone, thymol, cineol, methyl salicylate, vanilla, vanillin, licorice, thymol, and menthol;
(ii) about 0.05 to about 1% of a sweetener, selected from saccharin, sodium saccharin, sucralose, aspartame, *stevia*, potassium acesulfame, neotame, thaumatin, and sodium cyclamate;
(iii) about 0.1% to about 2.0% of a preservative, suitable to prevent bacterial growth during storage;
(iv) about 0.2% to about 2.0 of a buffer suitable to provide a pH of between about 3.5 and 9.5,
(v) a food-safe dye or an opacifier,
(vi) about 0.1% to about 0.25% opacifying titanium dioxide,
(vii) an emulsifier selected from poloxamer 407, polysorbate 20, polysorbate 89, and polysorbate 60, and Polyoxyl 40 Hydrogenated Castor Oil.

27. An oral hygiene composition according to claim 1, further comprising at least one of the following ingredients:
(i) about 0.1% to about 4% of a tartar control agent selected from an alkali metal or ammonium pyrophosphate salt, an alkali metal or ammonium hexametaphosphate salt, zinc acetate, zinc lactate, zinc chloride and zinc citrate,
(ii) a tooth desensitizing agent selected from about 0.1% to 7.0% potassium nitrate, from about 0.1% to about 2.0 stannous chloride, and from about 0.5 to about 2% strontium chloride;

(iii) a tooth whitening agent selected from one of the following whitening agents 0.5 to 2.5% hydrogen peroxide, 1.5% to 7% carbamide peroxide, 1.5 to 7.0% sodium percarbonate and 1.5 to 7.0% sodium perborate; and (iv) an antimicrobial agent comprising 0.1 to 0.5% chlorhexidine gluconate.

28. An oral hygiene composition according to claim 1 wherein:
said composition is a subgingival dentifrice;
said composition is in paste form; and
said composition further comprises from 0.1% to 0.5% of chlorhexidine gluconate or acetate.

29. An oral hygiene composition according to claim 1 wherein:
said composition is in a form of a prophylaxis paste, a prophylaxis gel, a prophylaxis powder, a subgingival plaque removing composition, or a fluoride gel treatment; and
said composition comprises 0.1% to 1% concentration of fluoride ions.

30. An oral hygiene composition according to claim 1 wherein:
said composition has a yield stress of more than 10 Pa and storage modulus greater than 1,000 Pa, both undiluted and also when the composition is diluted to 50%.

31. An oral hygiene composition according to claim 1 wherein;
said composition has a water activity of 0.75 or lower.

32. An oral hygiene composition according to claim 1 wherein;
said composition has a reduced presence of microstructural voids compared to an otherwise identical composition except without said at least one of glycerol, sorbitol, or a mixture of glycerol and sorbitol.

33. An oral hygiene composition according to claim 1 wherein; said composition comprises worm-like surfactant micelles.

34. An oral hygiene composition comprising:
a mixture of: (i) a carrier liquid; and (ii) water-insoluble hydratable polymer fibers forming an entangled three-dimensional network of said water-insoluble hydratable polymer liquid a fibers in said carrier liquid; wherein:
said carrier liquid comprises water and at least one of glycerol, sorbitol, or a mixture of glycerol and sorbitol, wherein the at least one of glycerol, sorbitol, or a mixture of glycerol and sorbitol is present in excess of 20 wt. % based on the weight of the composition;
said composition is effective to dislodge or remove more than 50% of a plaque-biofilm based on experiments based on subjecting the biofilm to a shear rate of 300 1/sec using the composition in an Anton Paar MCR 302 rheometer, and
said water-insoluble hydratable polymer fibers have a diameter of about 10 to about 20,000 nm and a length of at least 100 nm.

* * * * *